United States Patent
Fischbach et al.

(10) Patent No.: US 10,227,290 B2
(45) Date of Patent: Mar. 12, 2019

(54) GLYCOSPHINGOLIPIDS FOR USE IN MODULATING IMMUNE RESPONSES

(71) Applicants: The Regents of the University of California, Oakland, CA (US); President and Fellows of Harvard College, Cambridge, MA (US)

(72) Inventors: Michael A. Fischbach, San Francisco, CA (US); Jeffrey A. Bluestone, San Francisco, CA (US); Cristina Penaranda, Boston, MA (US); Laura Brown, Bloomington, IN (US); Jon Clardy, Jamaica Plain, MA (US)

(73) Assignees: The Regents of the University of California, Oakland, CA (US); President and Fellows of Harvard College, Cambridge, MA (US)

( * ) Notice: Subject to any disclaimer, the term of this patent is extended or adjusted under 35 U.S.C. 154(b) by 270 days.

(21) Appl. No.: 14/376,747

(22) PCT Filed: Feb. 7, 2013

(86) PCT No.: PCT/US2013/025205
§ 371 (c)(1),
(2) Date: Aug. 5, 2014

(87) PCT Pub. No.: WO2013/119857
PCT Pub. Date: Aug. 15, 2013

(65) Prior Publication Data
US 2014/0377291 A1    Dec. 25, 2014

Related U.S. Application Data

(60) Provisional application No. 61/596,039, filed on Feb. 7, 2012.

(51) Int. Cl.
| | | |
|---|---|---|
| *A61K 35/12* | (2015.01) | |
| *A61K 35/26* | (2015.01) | |
| *C07H 15/04* | (2006.01) | |
| *C07H 15/06* | (2006.01) | |
| *C12P 13/02* | (2006.01) | |
| *C12P 19/44* | (2006.01) | |
| *C07C 235/08* | (2006.01) | |
| *C07F 9/141* | (2006.01) | |

(52) U.S. Cl.
CPC ............ *C07C 235/08* (2013.01); *A61K 35/26* (2013.01); *C07F 9/1411* (2013.01); *C07H 15/04* (2013.01); *C07H 15/06* (2013.01); *C12P 13/02* (2013.01); *C12P 19/44* (2013.01); *A61K 2035/122* (2013.01)

(58) Field of Classification Search
None
See application file for complete search history.

(56) References Cited

U.S. PATENT DOCUMENTS

| | | |
|---|---|---|
| 4,981,618 A | 1/1991 | Bruneteau et al. |
| 5,683,684 A | 11/1997 | Montastier et al. |
| 5,869,034 A | 2/1999 | Montastier et al. |
| 5,936,076 A * | 8/1999 | Higa ............... C07H 15/10 424/520 |
| 5,958,426 A | 9/1999 | Moreau et al. |
| 6,071,884 A | 6/2000 | Koezuka et al. |
| 7,906,488 B2 | 3/2011 | Nieuwenhuizen |
| 7,968,529 B2 | 6/2011 | Nieuwenhuizen |
| 2006/0052316 A1 | 3/2006 | Porcelli |
| 2006/0116331 A1 | 6/2006 | Jiang et al. |
| 2009/0239813 A1 | 9/2009 | Cerundolo et al. |
| 2010/0104590 A1* | 4/2010 | Kang ............... C07H 15/00 424/184.1 |
| 2010/0304467 A1 | 12/2010 | Kodama et al. |

OTHER PUBLICATIONS

Brown, L. et al., PLoS Biology, "Production of alpha-Galactosylceramide by a Prominent Member of the Human Gut Microbiota", 2013, vol. 11, No. 7, pp. e1001610.*
Wollenweber, H.-W. et al., Journal of Bacteriology, "Nature, Type of Linkage, Quantitiy, and Absolute Configuration of (3-Hydroxy) Fatty Acids in Lipopolysaccharides from Bacteroides fragilis NCTC 9343 and Related Strains", 1980, vol. 144, No. 3, pp. 898-903.*
An et al., "Membrane sphingolipids as essential molecular signals for *Bacteroides* survival in the intestine," *PNAS* 108(Suppl. 1): 4666-4671, 2011.
Banchet-Cadeddu., "The stimulating adventure of KRN 7000," *Organic & Biomolecular Chemistry* 9: 3080-3104, 2011.
Bezbradica et al., "Distinct Roles of Dendritic Cells and B Cells in Va14Ja18 Natural T Cell Activation In Vivo," *The Journal of Immunology* 174: 4696-4705, 2012.
Borrow et al., "Innate immunity against HIV: a priority target for HIV prevention research," *Retrovirology* 7(84), 2010, 17 pages.
Brigl et al., "Innate iNKT cell activation during infection, Supplemental Material," *The Journal of Experimental Medicine* 208(6): S1-S10, 2008.

(Continued)

*Primary Examiner* — Shaojia A Jiang
*Assistant Examiner* — Bahar Craigo
(74) *Attorney, Agent, or Firm* — Seed IP Law Group LLP

(57) ABSTRACT

Provided herein are sphingolipid compounds that are useful for activating natural killer T cells. Also provided are methods for treating or preventing a disease or disorder that is treatable by activating the immune system by stimulating natural killer T cells. The compounds are therefore useful for treating or reducing the likelihood of occurrence of an immune diseases and disorders, such as autoimmune diseases or disorders. The compounds may also be used for treating or reducing the likelihood of occurrence of a microbial infection or for treating or reducing the likelihood of occurrence of a cancer in a subject by administering the sphingolipid compounds described herein.

12 Claims, 18 Drawing Sheets

Specification includes a Sequence Listing.

(56) References Cited

OTHER PUBLICATIONS

Brigl et al., "Innate and cytokine-driven signals, rather than microbial antigens, dominate in natural killer T cell activation during microbial infection," *The Journal of Experimental Medicine* 208(6) 1163-1177, 2011.

Brossay et al., "Cutting Edge: Structural Requirements for Galactosylceramide Recognition by CD1-Restricted NK T Cells," *The Journal of Immunology* 161: 5124-5128, 1998.

Burrows et al., "NKT cells turn ten," *Nature Immunology* 10(7): 669-671, 2009.

Fernandez et al., "Activation of invariant Natural Killer T lymphocytes in response to the α-galactosylceramide analogue KRN7000 encapsulated in PLGA-based nanoparticles and microparticles," *International Journal of Pharmaceutics* 423: 45-54, 2012.

Godfrey et al., "New ways to turn on NKT cells," *The Journal of Experimental Medicine* 208(6): 1121-1125, 2011.

Haak et al., "Hydroxylation of *Saccharomyces cerevisiae* Ceramides Requires Sur2p and Scs7p," *The Journal of Biological Chemistry* 272(47): 29704-29710, 1997.

Hancock et al., "Designer enzymes for glycosphingolipid synthesis by directed evolution," *Nature Chemical Biology* 5(7): 508-514, 2009.

Kawano et al., "CD1d-Restricted and TCR-Mediated Activation of $V_\alpha 14$ NKT Cells by Glycosylceramides," *Science* 278: 1626-1629, 1997.

Kinjo et al., "Natural killer T cells recognize diacylglycerol antigens from pathogenic bacteria," *Nature Immunology* 7(9): 978-986, 2006.

Kinjo et al., "Recognition of bacterial glycosphingolipids by natural killer T cells," *Nature* 434: 520-524, Mar. 2008.

Liu et al., "Total Synthesis of α-1C-Galactosylceramicle, an Immunostimulatory C-Glycosphingolipid, and Confirmation of the Stereochemistry in the First-Generation Synthesis," *J Org Chem.* 76(21): 8588-8598, 2011.

Mattner et al., "Exogenous and endogenous glycolipid antigens activate NKT cells during microbial infections," *Nature* 434: 525-529, 2005.

Nichols et al., "Unique Lipids from a Common Human Bacterium Represent a New Class of Toll-Like Receptor 2 Ligands Capable of Enhancing Autoimminity," *The American Journal of Pathology* 175(6): 2430-2438, 2009.

Paget et al., "Activation of Invariant NKT Cells by Toll-like Receptor 9-Stimulated Dendritic Cells Requires Type I Interferon and Charged Glycosphingolipids," *Immunity* 27: 597-609, 2007.

Raghuraman et al., "IFN-β-Mediated Up-Regulation of CD1d in Bacteria-Infected APCs," *The Journal of Immunology* 177: 7841-7848, 2012.

Salio et al., "Modulation of human natural killer T cell ligands on TRL-mediated anitigen-presenting cell activation," *PNAS* 104(51): 20490-20495, 2007.

Schmieg et al., "Glycolipid presentation to natural killer T cells differs in an organ-dependent fashion," *PNAS* 102(4): 1127-1132, Jan. 25, 2005.

Sidobre et al., "The Vα14 NKT Cell TCR Exhibits High-Affinity Binding to a Glycolipid/Cd1d Complex," *The Journal of Immunology* 169: 1340-1348, 2011.

Sidobre et al., "The T cell antigen receptor expressed by Va14i NKT cells has a unique mode of glycosphingolipid antigen recognition," *PNAS* 101(33): 12254-12259, 2004.

Sköld et al., "Interplay of Cytokines and Microbial Signals in Regulation of CD1d Expression and NKT Cell Activation," *The Journal of Immunology* 175: 3584-3593, 2005.

\* cited by examiner

A

*Bacteroides fragilis* ceramide phosphorylethanolamine
(CPE)

*Bacteroides fragilis* ceramide

Human plasma sphingomyelin

*Bacteroides fragilis* α-galactosylceramide
(α-GalCer_Bf)

*Agelas mauritianus* α-galactosylceramide
(agelasphin-9b)

agelasphin-9b derivative
(α-GalCer, KRN7000)

SEQUENCE LISTING

<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: Primer

<400> SEQUENCE: 1
ccttgagctc cagttcgata ttacggatca cctt          34

<210> SEQ ID NO 2
<211> LENGTH: 34
<212> TYPE: DNA
<213> ORGANISM: Artificial Sequence
<220> FEATURE:
<223> OTHER INFORMATION: Primer

```
<400> SEQUENCE: 2
ctgcacgcgt tatacgcctt tagcctttat ctgc                              34

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
ggcaacgcgt aagttagtga aatgtttcaa ggca                              34

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
tttggagctc ttcaatagtg taggaagcgt tttg                              34
```

GLYCOSPHINGOLIPIDS FOR USE IN MODULATING IMMUNE RESPONSES

CROSS-REFERENCE TO RELATED APPLICATION

This application is a U.S. national stage application filed under 35 U.S.C. § 371 of International Patent Application No. PCT/US2013/025205, accorded an international filing date of Feb. 7, 2013, which claims benefit under 35 U.S.C. § 119(e) of U.S. Provisional Patent Application No. 61/596,039 filed Feb. 7, 2012, which is incorporated herein by reference in its entirety.

STATEMENT OF GOVERNMENT INTEREST

This invention was made with government support under Grant No. DP2 OD007290, R37 AI46643, and R01 GM086258 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing 920085_416WO_SEQUENCE_LISTING.txt. The text file is 1 KB, was created on Feb. 7, 2013, and is being submitted electronically via EFS-Web.

BACKGROUND

Technical Field

Molecules are needed that modulate the immune response, such as for enhancing the immune response specific to a pathogen or to a tumor cell and for suppressing an autoimmune response, and that have minimal or no associated toxic effects. A class of signaling molecules that modulates the immune response and uses of these molecules are described herein.

Description of the Related Art

The innate immune response (or antigen non-specific or antigen independent immune response) is the first immune defense mechanism marshaled by a host in response to an infectious microorganism or other antigens recognized as non-self. Natural killer T (NKT) cells are a conserved T lymphocyte subpopulation that regulates multiple types of immune responses. Invariant natural killer T (iNKT) cells are a subset of these lymphocytes involved in the innate immune response. The iNKT cells recognize lipid antigens bound to the MHC class I-related molecule CD1d that is expressed by antigen presenting cells (APCs) (such as dendritic cells). In response to glycolipids, the iNKT cells produce large amounts of cytokines that leads to downstream activation of dendritic cells, natural killer (NK) cells, B cells, and T cells. Therefore, the iNKT cells modulate autoimmune diseases, inflammation, tumor resistance, and anti-microbial responses.

A non-mammalian glycosphingolipid, α-galactosylceramide (α-GalCer) such as KRN 7000, a glycosphingolipid derived from the sponge, *Agelas mauritianus*, has been studied and investigated in clinical trials (see, e.g., International Patent Application Publication No. WO 98/29534; Morita et al., *Biosci. Biotechnol. Biochem.* 60:288-92 (1996)). KRN 7000 has not achieved success, at least in part, because the cytokines produced by activated NKT cells cause an antagonistic effect, limiting its usefulness (see, e.g., Bancet-Cadeddu et al., *Org. Biomol. Chem.* 9:3080-104 (2011)).

Accordingly, identifying and developing other glycosphingolipid molecules is desirable for use as immunotherapeutic agents. The molecules and uses described herein address this unmet medical need.

BRIEF SUMMARY

Provided herein are glycosphingolipid compounds that are useful for modulating the immune response in a subject. In certain embodiments, the compounds and compositions comprising these compounds described herein may be used for suppressing an immune response, such as suppressing an autoimmune response. In other certain embodiments, these glycosphingolipid compounds and compositions may be useful for inducing or enhancing the immune response, such as the innate immune response, which is beneficial for treating and/or for reducing the risk of occurrence or reducing the severity and symptomatology of a microbial infection. The immune response induced or enhanced by these compounds and compositions may also be useful for preventing or treating a cancer. Compositions comprising these glycosphingolipid compounds and methods of using these compounds are also provided. Exemplary embodiments of the compounds, compositions, methods of using, and uses for these compounds are provided below and herein.

Embodiment 1. An isolated compound having the following structure I:

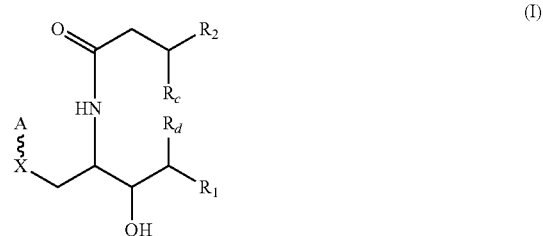

or a single stereoisomer, a mixture of stereoisomers, tautomer or pharmaceutically acceptable salt thereof, wherein A is a sugar moiety;

X is —O—, —S—, —NH—, or —CH$_2$—;

∼∼∼ is a glycosidic bond;

$R_1$ is $C_{5-28}$ fatty acid chain optionally substituted with one or more substituents selected from the group consisting of hydroxy, halo, —NR$_a$R$_b$, oxo, and $C_{1-3}$ lower alkyl, or -L$_1$-Q$_1$-R$_3$;

$R_2$ is $C_{5-28}$ fatty acid chain optionally substituted with one or more substituents selected from the group consisting of hydroxy, halo, —NR$_a$R$_b$, oxo, and $C_{1-3}$ lower alkyl; or -L$_2$-Q$_2$-R$_4$, provided that if $R_1$ is not hydroxy, $R_2$ is substituted with at least one hydroxy;

$R_a$ and $R_b$ are the same or different and independently hydrogen, acyl, or alkyl;

$R_c$ and $R_d$ are the same or different and independently hydrogen, hydroxy or alkyl;

$L_1$ and $L_2$ are the same or different and independently $C_{1-26}$ alkylene or $C_{2-26}$ alkenylene chain optionally substituted with one or more substituents selected from the group consisting of hydroxy, halo, —$NR_aR_b$, oxo, and $C_{1-3}$ lower alkyl;

$Q_1$ and $Q_2$ are the same or different and independently carbocycle or heterocycle; and $R_3$ and $R_4$ are the same or different and independently hydrogen or $C_{1-28}$ fatty acid chain optionally substituted with one or more substituents selected from the group consisting of hydroxy, halo, —$NR_aR_b$, oxo, and $C_{1-3}$ lower alkyl.

Embodiment 2. The compound of Embodiment 1, wherein the compound has the following structure (Ia):

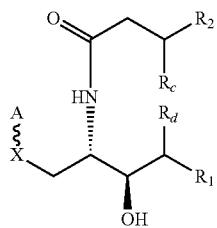

(Ia)

Embodiment 3. The compound of Embodiment 1, wherein $R_c$ is hydroxy and the compound has the following structure (II):

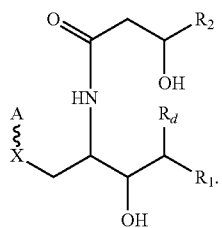

(II)

Embodiment 4. The compound of Embodiment 3 wherein the compound has the following structure (IIa):

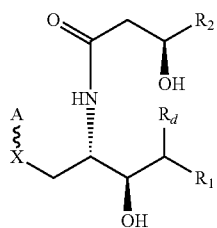

(IIa)

Embodiment 5. The compound of Embodiment 3, wherein the compound has the following structure (IIb):

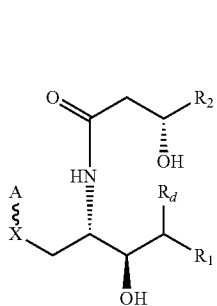

(IIb)

Embodiment 6. The compound of any one of Embodiments 1-5 wherein

X is —O—.

Embodiment 7. The compound of any one of Embodiments 1-6, wherein (a) A is a monosaccharide selected from glucose, galactose, mannose, talose, iodose, altrose, gulose, allose, ribose, arabinose, xylose, and lyxose or a derivative thereof or (b) A is a disaccharide selected from sucrose, lactulose, lactose, maltose, trehalose, and cellobiose or a derivative thereof.

Embodiment 8. The compound of any one of Embodiments 1-7 wherein the glycosidic bond is in a configuration.

Embodiment 9. The compound of any one of Embodiments 1-8 wherein A is

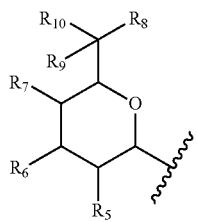

wherein, $R_5$, $R_6$, $R_7$, and $R_8$ are the same or different and independently hydrogen, —$OR_e$, —$NR_aR_b$, halo, or $C_{1-3}$ lower alkyl;

$R_9$ and $R_{10}$ are the same or different and independently hydrogen or $C_{1-3}$ lower alkyl, or $R_9$ and $R_{10}$ together form =O, =S or =NH;

$R_a$ and $R_b$ are the same or different and independently hydrogen, acyl, or alkyl; and $R_e$ is hydrogen, acyl, alkyl, a monosaccharide or a derivative thereof.

Embodiment 10. The compound of Embodiment 9 wherein A is a galactose derivative represented by

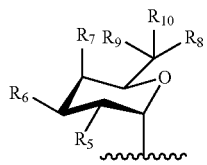

wherein, $R_5$, $R_6$, $R_7$, and $R_8$ are the same or different and independently hydrogen, —$OR_e$, —$NR_aR_b$, halo, or $C_{1-3}$ lower alkyl;

$R_9$ and $R_{10}$ are the same or different and independently hydrogen or $C_{1-3}$ lower alkyl, or $R_9$ and $R_{10}$ together form =O, =S or =NH;

$R_a$ and $R_b$ are the same or different and independently hydrogen, acyl, or alkyl, and $R_e$ is hydrogen, acyl, alkyl, a monosaccharide or a derivative thereof.

Embodiment 11. The compound of any one of Embodiments 1-9, wherein $R_2$ is $C_{5-28}$alkyl or $C_{5-28}$alkenyl.

Embodiment 12. The compound of Embodiment 11 wherein $R_2$ is $C_{5-19}$alkyl, $C_{5-15}$alkyl, $C_{9-19}$alkyl, $C_{9-15}$alkyl, $C_{5-19}$alkenyl, $C_{5-15}$alkenyl, $C_{9-19}$alkenyl or $C_{9-15}$alkenyl, and wherein $R_2$ may be optionally substituted with one or more hydroxy.

Embodiment 13. The compound of any one of Embodiments 1-12, wherein $R_2$ is —$(CH_2)_m CH_3$ or —$(CH_2)_m CH(CH_3)_2$, and wherein m is an integer of between 4 and 21.

Embodiment 14. The compound of Embodiment 13, wherein $R_2$ is —$(CH_2)_{11}CH(CH_3)_2$.

Embodiment 15. The compound of any one of Embodiments 1-14, wherein $R_1$ is $C_{5-28}$alkyl; $C_{5-28}$alkenyl; $C_{9-15}$alkyl; or $C_{9-15}$alkenyl; and wherein $R_1$ may be optionally substituted with one or more hydroxy.

Embodiment 16. The compound of Embodiment 15 wherein $R_d$ is hydroxy or hydrogen.

Embodiment 17. The compound of Embodiment 15 or Embodiment 16 wherein $R_1$ is —$(CH_2)_m CH_3$ or —$(CH_2)_m CH(CH_3)_2$, wherein m is an integer between 4 and 24.

Embodiment 18. The compound of Embodiment 17, wherein $R_1$ is —$(CH_2)_{12}CH_3$ or —$(CH_2)_{10}CH(CH_3)_2$.

Embodiment 19. The compound of any one of Embodiments 1-4, 6-15, 16, and 17-18 having the following structure:

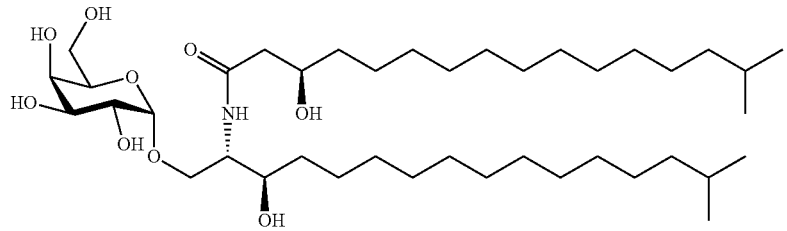

Embodiment 20. The compound of Embodiments 1-3, 5-15, 16, and 17-18 having the following structure:

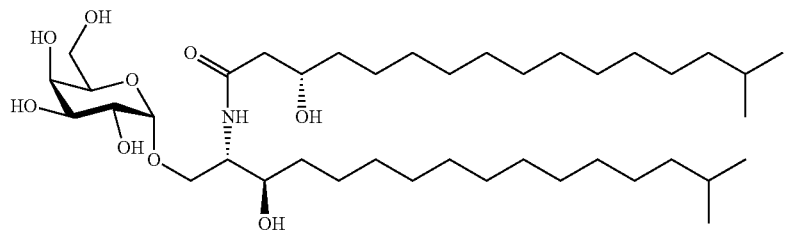

Embodiment 21. A pharmaceutical composition comprising the compound of any one of Embodiments 1-20 and a pharmaceutically acceptable excipient.

Embodiment 22. A method for activating a natural killer T cell (NKT cell) comprising contacting the NKT cell with the compound of any one of Embodiments 1-20.

Embodiment 23. The method of Embodiment 22 wherein the compound is specifically bound to a CD1 protein.

Embodiment 24. A method for treating a cancer in a subject, said method comprising administering the pharmaceutical composition of Embodiment 21 to the subject.

Embodiment 25. A method for treating a microbial infection in a subject, said method comprising administering the pharmaceutical composition of Embodiment 21 to the subject.

Embodiment 26. The method of Embodiment 25, wherein the microbial infection is a viral infection, bacterial infection, fungal infection, or parasitic infection.

Embodiment 27. A method for treating an autoimmune disease or disorder in a subject, said method comprising administering the pharmaceutical composition of Embodiment 21 to the subject.

Embodiment 28. A method for treating an immune disease or disorder in a subject comprising (a) contacting a plurality of NKT cells with the compound of any one of Embodiments 1-20 to provide a plurality of activated NKT cells, and (b) administering the plurality of activated NKT cells to the subject.

Embodiment 29. The method of Embodiment 28, prior to or concurrent with step (a), the compound is permitted to interact with a CD1 protein to form a compound:CD1 protein complex.

Embodiment 30. A method for inducing an immune response in a subject, comprising administering to the subject the pharmaceutical composition of Embodiment 21, wherein the subject has or is suspected of having a microbial infection.

Embodiment 31. The method of Embodiment 30, wherein the microbial infection is a viral infection, bacterial infection, fungal infection, or parasitic infection.

Embodiment 32. A method for inducing an immune response in a subject, comprising administering to the subject the pharmaceutical composition of Embodiment 21, wherein the subject has or is suspected of having a cancer.

Embodiment 33. A method for suppressing an immune response in a subject, comprising administering to the subject the pharmaceutical composition of Embodiment 21, wherein the subject has or is suspected of having an autoimmune disease.

Embodiment 34. The method of Embodiment 27, wherein the autoimmune disease is Type 1 diabetes mellitus.

Embodiment 35. The method of Embodiment 33, wherein the autoimmune disease is Type 1 diabetes mellitus.

Embodiment 36. A method of producing the compound of any one of Embodiments 1-20, comprising (a) culturing bacteria that express the compound in a culture media to provide a bacterial culture; (b) obtaining the bacterial cells from the bacterial culture; and (c) isolating the compound from the bacterial cells.

Embodiment 37. The method of Embodiment 36, wherein the bacteria is *Bacteroides fragilis*.

Embodiment 38. Use of the compound of any one of Embodiments 1-20 for the manufacture of a medicament for treating a cancer.

Embodiment 39. Use of the compound of any one of Embodiments 1-20 for the manufacture of a medicament for treating a microbial infection.

Embodiment 40. Use of the compound of any one of Embodiments 1-20 for the manufacture of a medicament for treating an autoimmune disease or disorder.

Embodiment 41. Use of the compound of any one of Embodiments 1-20 for the manufacture of a medicament for treating an immune disease or disorder.

Embodiment 42. Use of the compound of any one of Embodiments 1-20 for the manufacture of a medicament for inducing an immune response in a subject who has a cancer or a microbial infection.

Embodiment 43. Use of the compound of any one of Embodiments 1-20 for the manufacture of a medicament for suppressing an immune response in a subject who has an autoimmune disease or disorder.

In the following description, certain specific details are set forth in order to provide a thorough understanding of various embodiments. However, one skilled in the art will understand that the embodiments may be practiced without these details. In other instances, well-known structures have not been shown or described in detail to avoid unnecessarily obscuring descriptions of the embodiments. Unless the context requires otherwise, throughout the specification and claims that follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise.

When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise.

BRIEF DESCRIPTION OF THE DRAWINGS

FIG. 1A: *B. fragilis* produces the phosphosphingolipid ceramide phosphoryl-ethanolamine (CPE, top) and the corresponding free ceramide (middle), which are similar in structure to the most abundant (4,5-dehydro) and third-most abundant (4,5-dihydro) forms of sphingomyelin in human plasma (bottom). FIG. 1B: *B. fragilis* produces the glycosphingolipid α-galactosylceramide (α-GalCer$_{Bf}$, top); sponge-derived α-galactosylceramide agelasphin-9b (middle); and KRN7000, which is a derivative of agelasphin-9b (bottom).

FIG. 4A: NKT cell hybridomas (see Example 4) were stained with anti-CD3 antibodies, and empty mCD1d tetramers or CD1d tetramers were loaded with α-GalCer$_{Bf}$ or KRN7000. Flow cytometry plots representative of three independent experiments are shown. FIG. 4B: Hybridomas were cultured with BMDCs (bone marrow-derived dendritic cells) pre-pulsed with LPS or LPS+α-GalCer$_{Bf}$ in the presence of control Ig or anti-CD1d blocking antibodies. IL-2 secretion was measured in supernatants 16 hr later. Data are representative of three independent experiments. FIG. 4C: Liver mononuclear cells were cultured with splenocytes plus increasing amounts of α-GalCer$_{Bf}$ in the presence or absence of anti-CD1d blocking antibodies. IFN-γ secretion was measured in supernatants on day 5. Data are representative of three independent experiments.

FIG. 6A: PBMCs were cultured for 13 days with 0.1 µg/mlKRN7000, 1 µg/ml α-GalCer$_{Bf}$, or 1 µg/ml ceramide$_{Bf}$. Dot plots show CD3$^+$Vα24$^+$NKT cells pre- and post-expansion. The data shown are representative of at least two individual experiments performed with six individual donors. FIG. 6B: Human NKT cells were purified after two rounds of expansion with 1 µg/ml α-GalCer$_{Bf}$ and restimulated with 10 µg/ml α-GalCer$_{Bf}$ in the presence or absence of control Ig or anti-Cd1d blocking antibodies. IFN-γ secretion was measured in supernatants 40-48 hours later. Data are representative of two independent experiments.

FIGS. 7A-7C: Expression of CD25 and CD69 on gated CD3$^+$tetramer$^+$ cells. Representative flow cytometry plots and pooled data showing fold change of CD25 and CD69 surface expression compared to NKT cells isolated from mice transferred with LPS-pulsed BMDCs. FIGS. 7D and 7E provide representative flow cytometry plots and pooled data, respectively, of intracellular IFN-γ expression on gated CD3$^+$ tetramer$^+$ cells. FIG. 7F presents serum IFN-γ levels.

DETAILED DESCRIPTION

Figure 1A:
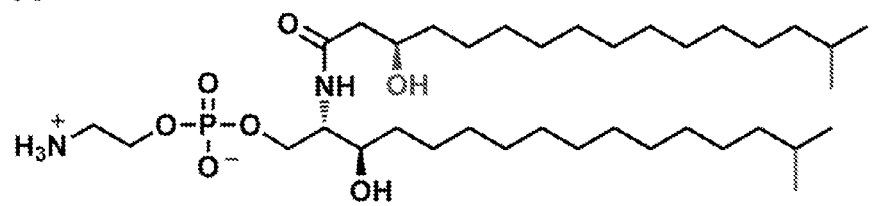
FIGS. 1A and 1B illustrate chemical structures of the *B. fragilis* sphingolipids and related molecules.
Figure 1A:
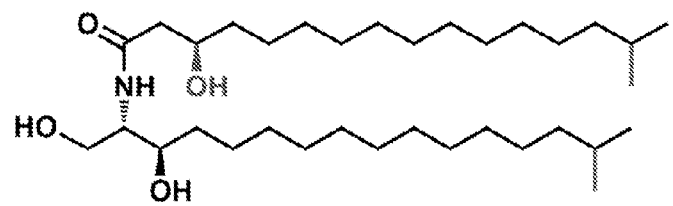
Figure 1A:
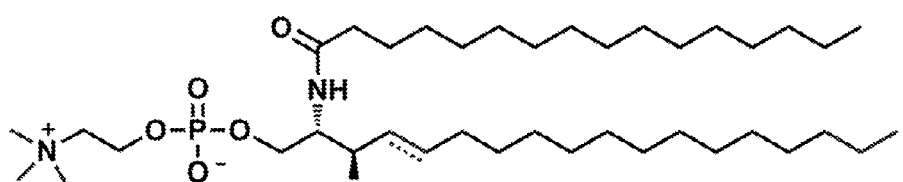

Glycolipid compounds, including glycosphingolipid compounds, are described herein that are useful for modulating the immune response in a host or subject. These compounds bind to CD1d and stimulate immune cells, including natural killer T (NKT) cells, to produce cytokines (e.g., interleukin-2 (IL-2) and interferon-gamma (IFN-γ)). The previously unidentified glycosphingolipid compounds also stimulate NKT cells to produce activation markers, such as CD25 and CD69. These compounds may be useful for inducing an immune response, such as an innate immune response against pathogens and tumor cells, and may also be useful for suppressing an immune response, such as an autoimmune response.

The glycosphingolipid compounds described herein provide an improvement over the art. A glycosphingolipid, α-galactosylceramide (α-GalCer) such as KRN 7000, previously known in the art, is a synthetic analogue of a glycosphingolipid from the sponge, *Agelas mauritianus*, and has been studied and investigated in clinical trials (see, e.g., International Patent Application Publication No. WO 98/29534; Morita et al., *Biosci. Biotechnol. Biochem.* 60:288-92 (1996); Kobayashi et al., *Oncol. Res.* 7:529-34 (1995)). KRN 7000 has not achieved success, however, at least in part, because the cytokines produced by activated NKT cells cause an antagonistic effect, limiting its usefulness (see, e.g., Bancet-Cadeddu et al., *Org. Biomol. Chem.* 9:3080-104 (2011)).

Sphingolipids and their breakdown products modulate a variety of eukaryotic signaling pathways involved in proliferation, apoptosis, differentiation, and migration. Sphingolipids are ubiquitous among eukaryotes, but production is less prevalent in prokaryotes (see, e.g., Olsen et al., *Anaerobe* 7:103-12 (2001)). More recently, studies have shown that different pathogenic microorganisms produce different lipid molecules that activate NKT cells (see, e.g., Kinjo et al., *Nat. Immunol.* 7:978-86 (2006); Kinjo et al., *Nature* 434:520-25 (2005); Mattner et al., *Nature* 434:525-29 (2005); Brigl et al., *J. Exp. Med.* 208:1163-77 (2011)). NKT cells are also activated by certain environmental antigens (see, e.g., Wingender et al., *J. Exp. Med.* 208:1151-62 (2011)). See also Godfrey et al., *J. Exp. Med.* 208:1121-25 (2011). However, while a variety of NKT cell ligands have been described, most are either much lower-affinity host-derived self-ligands (see, e.g., Zhou et al., *Science* 306: 1786-89 (2004)) or ligands from bacterial species that are not common mutualists or pathogens of mammals (see, e.g., Kinjo et al., Nature, supra; Kinjo et al., *Nat. Immunol.*, supra) and are therefore unlikely to be natural antigens for NKT cells.

The genus *Bacteroides* and its relatives, which may comprise as much as 50% of normal human gut microbiota (see, e.g., Turnbaugh et al., *Nature* 457:480-84 (2009)), are unusual among bacteria in that 40-70% of the membrane phospholipids of these prominent symbionts are sphingolipids (see, e.g., Rizza et al., *J Bacteriol* 101:84-91 (1970); Kunsman et al., *Appl Microbiol* 28:1088-89 (1974)). While the structures of several *Bacteroides* sphingolipids have been solved, the full repertoire of these molecules has not yet been defined (see, e.g., LaBach et al., *J. Lipid Res.* 10:528-34 (1969); White et al., *Biochim. Biophys. Acta— Lipids and Lipid Metabolism* 187:527-32 (1969); Rizza et al., supra; White et al., *Lipids* 5:56-62 (1970); Kemp et al., *Biochem. J.* 130:221-7 (1972); Lev et al., *J. Lipid Res.* 13:364-70 (1972); Kunsman, *J. Bacteriol.* 113:1121-26 (1973); Miyagawa, *J. Gen. Appl. Microbiol.* 24:341-48 (1978); Lev, *Am. J. Clin. Nutr.* 32:179-86 (1979); Miyagawa et al., *J. Biochem* 86:311-20 (1979); Olsen, *Acta Odontol. Scand.* 52:354-67 (1994); Kato et al., *Anaerobe* 1:135-39 (1995); Kato et al., *Anaerobe* 8:23-28 (2002); Ikushiro et al., supra; An et al., *Proc. Natl. Acad. Sci.* 108:4666-71 (2011)). An exemplary glycosphingolipid compound described herein (called α-GalCer$_{Bf}$ herein) has been isolated from *Bacteroides fragilis*, which is present as a bacterial species of human normal gut microbiota. Because the α-GalCer$_{Bf}$ compound and other compounds of structure I and structure II, as described, are normal gut flora in humans, administration of the compounds may be well-tolerated by a subject and not produce any toxic effect, particularly in a human subject. The glycosphingolipid compounds described herein may be chemically synthesized or isolated from a natural or engineered source, such as bacteria, according to methods described herein and using techniques routinely practiced in the art.

Glycosphingolipid Compounds

The following glycosphingolipid compounds and pharmaceutical compositions comprising these compounds are useful for activating NKT cells and are thereby useful for treating diseases and disorders treatable by activating NKT cells.

In one embodiment is provided herein an isolated compound having the following structure (I):

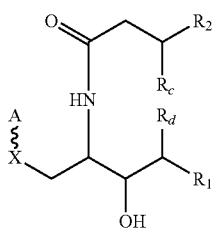

(I)

or a single stereoisomer, a mixture of stereoisomers, tautomer or pharmaceutically acceptable salt thereof, wherein A is a sugar moiety;

X is —O—, —S—, —NH—, or —CH$_2$—;

∼∼∼ is a glycosidic bond;

$R_1$ is C$_{5-28}$ fatty acid chain optionally substituted with one or more substituents selected from the group consisting of hydroxy, halo, —NR$_a$R$_b$, oxo, and C$_{1-3}$ lower alkyl, or -L$_1$-Q$_1$-R$_3$;

$R_2$ is C$_{5-28}$ fatty acid chain optionally substituted with one or more substituents selected from the group consisting of hydroxy, halo, —NR$_a$R$_b$, oxo, and C$_{1-3}$ lower alkyl; or -L$_2$-Q$_2$-R$_4$, provided that if R$_c$ is not hydroxy, R$_2$ is substituted with at least one hydroxy;

$R_a$ and $R_b$ are the same or different and independently hydrogen, acyl, or alkyl;

$R_c$ and $R_d$ are the same or different and independently hydrogen, hydroxy or alkyl;

$L_1$ and $L_2$ are the same or different and independently C$_{1-26}$ alkylene or C$_{2-26}$ alkenylene chain optionally substituted with one or more substituents selected from the group consisting of hydroxy, halo, —NR$_a$R$_b$, oxo, and C$_{1-3}$ lower alkyl;

$Q_1$ and $Q_2$ are the same or different and independently carbocycle or heterocycle; and $R_3$ and $R_4$ are the same or different and independently hydrogen or C$_{1-28}$ fatty acid chain optionally substituted with one or more substituents selected from the group consisting of hydroxy, halo, —NR$_a$R$_b$, oxo, and C$_{1-3}$ lower alkyl.

A further embodiment provides a compound of the following structure (Ia):

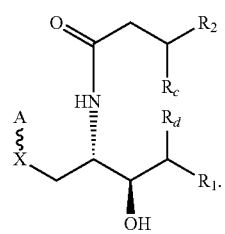

(Ia)

When R$_c$ of structure (Ia) is hydroxy, a further embodiment provides a compound of structure (II):

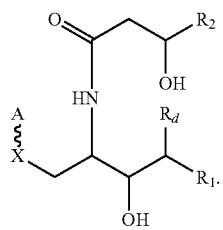

(II)

A further embodiment provides a compound of the following structure (IIa), in which the asymmetric carbons are shown with their respective stereochemistry:

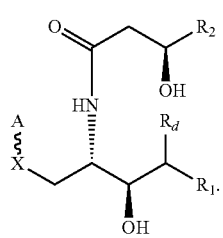

(IIa)

A further embodiment provides a compound of the following structure (IIb), in which the asymmetric carbons are shown with their respective stereochemistry:

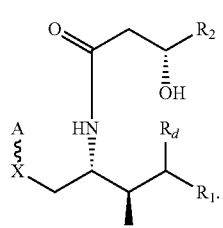

(IIb)

In various other embodiments, X may be —O— in a compound of Formulae (I), (Ia), (II), (IIa) or (IIb).

In various other embodiments, in a compound of Formulae (I), (Ia), (II), (IIa) or (IIb), A may be a monosaccharide selected from glucose, galactose, mannose, talose, iodose, altrose, gulose, allose, ribose, arabinose, xylose, and lyxose or a derivative thereof or A may be a disaccharide selected from sucrose, lactulose, lactose, maltose, trehalose, and cellobiose or a derivative thereof.

In further embodiments, the glycosidic bond is in a configuration in a compound of Formulae (I), (Ia), (II), (IIa) or (IIb).

In a specific embodiment, of a compound of Formulae (I), (Ia), (II), (IIa) or (IIb), A is

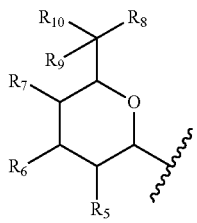

wherein, $R_5$, $R_6$, $R_7$, and $R_8$ are the same or different and independently hydrogen, —$OR_e$, —$NR_aR_b$, halo, or $C_{1-3}$ lower alkyl;

$R_9$ and $R_{10}$ are the same or different and independently hydrogen or $C_{1-3}$ lower alkyl, or $R_9$ and $R_{10}$ together form =O, =S or =NH;

$R_a$ and $R_b$ are the same or different and independently hydrogen, acyl, or alkyl; and $R_e$ is hydrogen, acyl, alkyl, a monosaccharide or a derivative thereof.

In more specific embodiments, each of $R_5$, $R_6$, $R_7$, and $R_8$ is hydroxy, and each of $R_9$ and $R_{10}$ is hydrogen.

In a further embodiment, the $C_{1-3}$ lower alkyl is methyl.

In a more specific embodiment, A is galactose.

In more specific embodiments, where one of $R_5$, $R_6$, $R_7$, or $R_8$ is —$OR_e$ and $R_e$ is a monosaccharide, A is a disaccharide.

In a specific embodiment, of a compound of Formulae (I), (Ia), (II), (IIa) or (IIb), A is

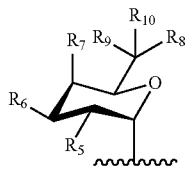

wherein, $R_5$, $R_6$, $R_7$, and $R_8$ are the same or different and independently hydrogen, —$OR_e$, —$NR_aR_b$, halo, or $C_{1-3}$ lower alkyl;

$R_9$ and $R_{10}$ are the same or different and independently hydrogen or $C_{1-3}$ lower alkyl, or $R_9$ and $R_{10}$ together form =O, =S or =NH;

$R_a$ and $R_b$ are the same or different and independently hydrogen, acyl, or alkyl, and $R_e$ is hydrogen, acyl, alkyl, a monosaccharide or a derivative thereof.

In more specific embodiments, each of $R_5$, $R_6$, $R_7$, and $R_8$ is hydroxy, and each of $R_9$ and $R_{10}$ is hydrogen.

In a further embodiment, the $C_{1-3}$ lower alkyl is methyl.

In a more specific embodiment, A is galactose.

In more specific embodiments, where one of $R_5$, $R_6$, $R_7$, or $R_8$ is —$OR_e$ and $R_e$ is a monosaccharide, A is a disaccharide.

In various embodiments, of a compound of Formulae (I), (Ia), (II), (IIa) or (IIb), $R_2$ is $C_{5-28}$alkyl or $C_{5-28}$alkenyl.

In more specific embodiments, $R_2$ is $C_{5-19}$alkyl, $C_{5-15}$alkyl, $C_{9-19}$alkyl, $C_{9-15}$alkyl, $C_{5-19}$alkenyl, $C_{5-15}$alkenyl, $C_{9-19}$alkenyl or $C_{9-15}$alkenyl, and wherein $R_2$ may be optionally substituted with one or more hydroxy.

In another specific embodiment, $R_2$ is a fatty acid substituted with at least one methyl.

In still another specific embodiment, $R_2$ is —$(CH_2)_mCH_3$, or —$(CH_2)_mCH(CH_3)_2$, wherein m is an integer between 4 and 21 (e.g., 4, 5, 6, 7, 8, 9, 10, 11, 12, 13, 14, 15, 16, 17, 18, 19, 20, or 21). In a specific embodiment, $R_2$ is —$(CH_2)_{11}CH(CH_3)_2$.

In various embodiments, of a compound of Formulae (I), (Ia), (II), (IIa) or (IIb), $R_1$ is $C_{5-28}$alkyl; $C_{5-28}$alkenyl; $C_{9-15}$alkyl; or $C_{9-15}$alkenyl; and wherein $R_1$ may be optionally substituted with one or more hydroxy. In other embodiments, $R_d$ is hydroxy. In yet other embodiments, $R_d$ is hydrogen. In more specific embodiments, $R_1$ is a fatty acid substituted with at least one methyl. In various embodiments, $R_1$ is —$(CH_2)_mCH_3$ or —$(CH_2)_mCH(CH_3)_2$, wherein m is an integer between 4 and 24 (e.g., 4, 5, 6, 7, 8, 9, 10, 11, 12, 13, 14, 15, 16, 17, 18, 19, 20, 21, 22, 23, or 24). In more specific embodiments, $R_1$ is —$(CH_2)_{12}CH_3$ or —$(CH_2)_{10}CH(CH_3)_2$.

A specific embodiment provides a compound of the following structure, also called herein, $\alpha$-GalCer$_{Bf}$.

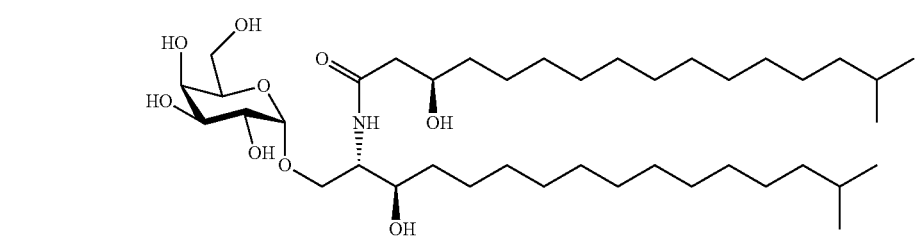

Another specific embodiment provides a compound of the following structure:

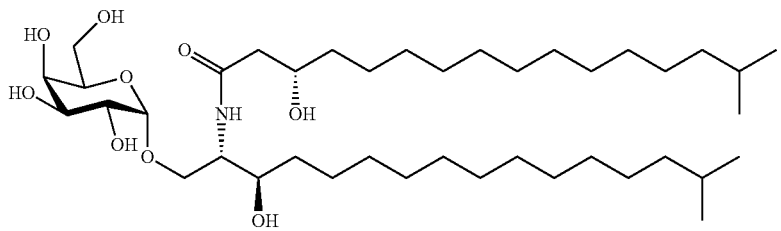

Also provided herein is a pharmaceutical composition comprising a compound of Formulae (I), (Ia), (II), (IIa) or (IIb) including all substructures and specific structures described herein, and a pharmaceutically acceptable excipient.

DEFINITIONS

The terms below, as used herein, have the following meanings, unless indicated otherwise. Certain chemical groups named herein are preceded by a shorthand notation indicating the total number of carbon atoms that are to be found in the indicated chemical group.

"Fatty acid chain" refers to aliphatic hydrocarbon chains or radicals that comprise up to 30 carbons, more typically 5-28, 5-15, 9-15, 9-28, 5-30, 9-30 carbons, for example, and the like. The fatty acid chain can be saturated or unsaturated. Saturated fatty acid chain may be an alkyl radical, defined as comprising solely of carbon and hydrogen and with no double or triple carbon-carbon bonds. Unsaturated fatty acid chain may be an alkenyl radical, defined as comprising solely of carbon and hydrogen and containing at least one and up to 15 double bonds. The fatty acid chain is attached, via a carbon atom, to the rest of the molecule by a single bond. In various embodiments, the fatty acid chain may be unbranched or branched. In other various embodiments, the fatty acid chain may be further substituted with one of more substituents selected from hydroxy, halo, —$NR_aR_b$, oxo, and $C_{1-3}$ lower alkyl, and wherein $R_a$ and $R_b$ are each independently hydrogen, acyl, or alkyl.

"Lower alkyl" refers to an alkyl radical, defined herein, that has 1 to 3 carbon atoms. Examples of the lower alkyl include methyl, ethyl, propyl, and isopropyl.

"Alkylene" and "alkylene chain" refer to a straight or branched divalent hydrocarbon chain consisting solely of carbon and hydrogen, containing no unsaturation and having up to 30 carbon atoms, preferably having from 1-28 carbons, e.g., methylene, ethylene, propylene, n-butylene, and the like. The alkylene chain links two moieties, e.g., the remainder of the molecule and another radical. The alkylene chain may be attached to the remainder of the molecule and to the radical group through any two carbons, typically, the two terminal carbon atoms, within the chain.

"Alkenylene" and "alkenylene chain" refer to a straight or branched divalent hydrocarbon chain consisting solely of carbon and hydrogen, containing at least one double bond and having up to 30 carbon atoms, preferably having from 2-28 carbons, e.g., ethenylene, propenylene, n-butenylene, and the like. The alkylene chain links two moieties, e.g., the remainder of the molecule and another radical. The alkenylene chain may be attached to the remainder of the molecule and to the radical group through any two carbons, typically, the two terminal carbon atoms, within the chain.

Acyl refers to a radical —C(O)—R, wherein R is alkyl, aralkyl, carbocyclyl, aryl, heteroaryl or heterocyclyl, as defined herein. When R is methyl, the acyl group is also referred to as acetyl.

Halo refers to fluoro, chloro, bromo or iodo radical.

"Carbocyclyl" or "carbocycle" refers to a stable monocyclic or bicyclic hydrocarbon radical consisting solely of carbon and hydrogen atoms, having from three to fifteen ring carbon atoms, preferably having from three to ten ring carbon atoms, and which is saturated (no double bond) or unsaturated (having at least one double bond). Carbocyclyl may also be non-aromatic or aromatic. Non-aromatic carbocyclyl includes, e.g., cyclopropyl, cyclobutyl, cyclopentyl, cyclohexyl, decalinyl and the like. Aromatic carbocyclyl is also referred to as aryl, as further defined herein. In certain embodiments, the carbocycle may be a monovalent radical that is attached to the remainder of the molecule via a single or double bond at any one of the ring carbon atom. In other embodiments, the carbocycle may be a bivalent radical that is attached to two radicals (e.g., an alkylene chain and an alkyl) via single or double bonds at any two of the ring carbon atoms. Unless otherwise stated specifically in the specification, the term "carbocyclyl" is meant to include radicals which are optionally substituted by one or more substituents independently selected from the group consisting of alkyl (e.g., $C_{1-3}$ lower alkyl), halo, hydroxy, —$NR_aR_b$, oxo, and $C_{1-3}$ lower alkyl, and wherein $R_a$ and $R_b$ are each independently hydrogen, acyl, or alkyl.

"Aryl" is a subset of carbocycle and refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl (e.g., $C_{1-3}$ lower alkyl), halo, hydroxy, —$NR_aR_b$, oxo, and $C_{1-3}$ lower alkyl, and wherein $R_a$ and $R_b$ are each independently hydrogen, acyl, or alkyl.

"Aralkyl" refers to a radical of the formula —$R_xR_y$, where $R_x$ is an alkylene radical as defined above and $R_y$ is one or more aryl radicals as defined above. Examples of aralkyl include benzyl, diphenylmethyl and the like. The aryl radical(s) may be optionally substituted as described above.

"Heterocyclyl" refers to a stable 3- to 18-membered non-aromatic ring radical which consists of carbon atoms and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Aromatic heterocycles are also referred to as heteroaryls, as further defined herein. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In certain embodiments, the heterocycle may be a monovalent radical that is attached to the remainder of the molecule via a single or double bond at any one of the ring atom (e.g., carbon or nitrogen). In other embodiments, the heterocycle may be a bivalent radical that is attached to two radicals (e.g., an alkylene chain and an alkyl) via single or double bonds at any two of the ring atoms (e.g., carbon or nitrogen). Unless stated otherwise specifically in the specification, the term "heterocyclyl" is meant to include heterocyclyl radicals as defined above which are optionally substituted by one or more substituents independently selected from the group consisting of alkyl (e.g., $C_{1-3}$ lower alkyl), halo, hydroxy, $-NR_aR_b$, oxo, and $C_{1-3}$ lower alkyl, and wherein $R_a$ and $R_b$ are each independently hydrogen, acyl, or alkyl.

"Heteroaryl" is a subset of heterocycle and refers to a 3- to 18-membered aromatic ring radical which consists of carbon atoms and from one to five heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl (e.g., $C_{1-3}$ lower alkyl), halo, hydroxy, $-NR_aR_b$, oxo, and $C_{1-3}$ lower alkyl, and wherein $R_a$ and $R_b$ are each independently hydrogen, acyl, or alkyl.

Oxo refers to the =O radical.

"Sugar" or "sugar moiety" refers to naturally or unnaturally-occurring cyclic carbohydrate that may be represented by the chemical formula $C_x(H_2O)_y$, wherein x is 5 or 6. The sugar moiety may be enzymatically or chemically added on to a glycosyl residue of the remainder of the molecule. The sugar may be a monosaccharide selected from glucose, galactose, mannose, talose, iodose, altrose, gulose, allose, ribose, arabinose, xylose, and lyxose or a disaccharide selected from sucrose, lactulose, lactose, maltose, trehalose, and cellobiose. Unless specified otherwise, the term "sugar" or "sugar moiety" is meant to include sugar as defined above, as well as a derivative of a sugar. For instance, a derivative of a sugar (a monosaccharide or disaccharide) include compounds in which the hydroxy groups of the sugar moiety may be further derivatized, replaced or substituted by another radical, including for example, alkyl (e.g., $C_{1-3}$ lower alkyl), halo, hydroxy, $-NR_aR_b$ (including amino and N-acetylamino), oxo. In a preferred embodiment, the sugar moiety is a galactose or derivatives thereof.

"Glycosidic bond" refers to a covalent bond that joins a sugar moiety to the remainder of the group. In particular, the glycosidic bond is formed between the hemiacetal group of the sugar moiety to a hydroxy group (or a thiol, amino or methylene group) of the remainder of the molecule. The orientation of the glycosidic bond may be in an a configuration (axial orientation) or in a β configuration (equatorial orientation).

"Optional" or "optionally" means that the subsequently described event or circumstance may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of Structures I and II and substructures thereof, as well as any and all substructures and specific compounds described herein is intended to encompass any and all pharmaceutically suitable salt forms.

Compounds of Structures I and II and substructures thereof may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

With regard to stereoisomers, the compounds of structure (I) and structure (II), as well as any sub-structure herein, may have one or more chiral (or asymmetric) centers, for example, in the fatty acid chain or any of $R^1$-$R^8$, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise specified (e.g., in certain embodiments, a stereocenter is indicated with an "*"), all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor)

"Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Compound Synthesis

The compounds of Formula (I) and subgenus structures represented by Formula (Ia), (II), (IIa) and (IIb) can be prepared by assembling a number of basic building blocks. As shown below, at the dashed lines, bond disconnection of a compound of Formula (I) lead to three building blocks: (1) sphinganine, (2) fatty acid and (3) sugar building blocks.

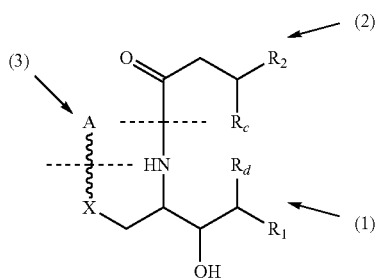

The building block can be obtained from commercial sources (e.g., Continental Chemical USA, FL for fatty acids) or separately prepared according to known methods in the art. See, for example, Muller et al., *Helvetica Chimica Acta* 76:616-630 (1993), Dondoni et al., *Organic Syntheses Coll.* 10:320 (2004), Mun et al., *Org. Biomol. Chem.* 5:3826-33 (2007), Azuma et al., *J. Org. Chem.* 65:3538-41 (2000), Labeeuw et al., *Tetrahedron Letters* 44:6383-86 (2003), Bancet-Cadeddu et al., *Org. Biomol. Chem.* 9:3080-104 (2011).

The following General Reaction Scheme shows the preparation of building block sphinganine (1) and coupling of the same with fatty acid building block (2) to provide a ceramide (G). Ceramide (G) is further coupled to a sugar (an α-galactose derivative) to provide a compound of Formula (Ia). Formula (Ia) is shown as a representative structure in order to show control over stereochemistry.

General Reaction Scheme

Sphinganine Synthesis

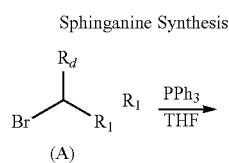

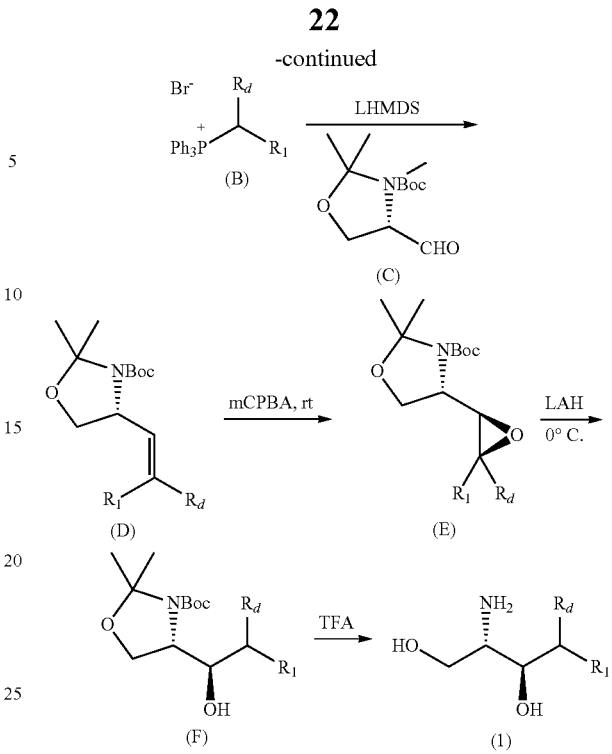

Ceramide Synthesis

Glycosphinolipid Synthesis

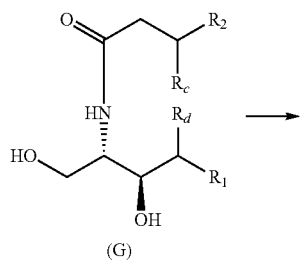

-continued

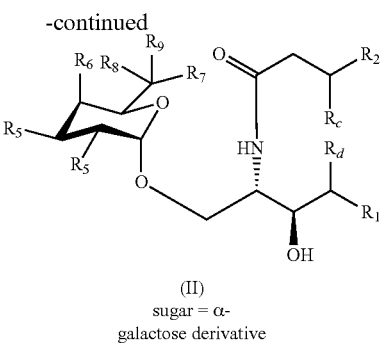

(II)

sugar = α-galactose derivative

Generally speaking, building block sphinganine (1) can be prepared starting from a fatty acid bromine derivative (A). (A) is converted to a Wittig reagent (B) via reaction with triphenylphosphine. (B) subsequently reacts with a protected serine-derived aldehyde (C) in the presence of a strong base (e.g., lithium bis(trimethylsilyl)amide/LHMDS) to provide an olefin derivative (D). The resulting olefin (D) retains the stereochemistry of (C) and is predominantly in the Z form. Epoxidation of olefin (D) can be carried out in the presence of meta-chloroperoxybenzoic acid (mCPBA) to provide epoxide (E), which is subsequently reduced to an N-protected precursor of sphinganine (F). Deprotection of (F) affords sphinganine (1).

Sphinganine (1) can be coupled with fatty acid (2) in the presence of N-ethoxycarbonyl-2-ethoxy-1,2-dihydroquinoline (EEDQ) to provide ceramide (G) without racemization.

Ceramide (G) undergoes glycosylation by coupling with an iodo-substituted sugar (in αconfiguration) to provide a couple of Formula (II).

To prepare a compound of Formula (II) (i.e., where $R_c$ is hydroxy), a β-hydroxy fatty acid is used as building block (2). β-hydroxy fatty acids can be readily prepared according to known methods in the art. See, Labeeuw et al., *Tetrahedron Letters* 44:6383-86 (2003).

Production of Glycosphingolipid Compounds in Host Cells

In certain embodiments, a glycosphingolipid compound is produced by bacteria (e.g., *Bacteroides* sp. including *Bacteroides fragilis*; *E. coli*). A glycosphingolipid compound that is "isolated," includes a compound that has been removed, partially or completely, from its original environment (e.g., the natural environment if it is naturally occurring). In certain embodiments, the compounds described herein may be produced in a host cell, such as a bacterial cell. Host cells (i.e., a plurality of host cells) may be cultured (i.e., grown, expanded) under conditions and for a time sufficient to permit multiple divisions of the host cells so that a host cell culture may be obtained. The host cells are cultured in a cell culture media that comprises nutrients, minerals, vitamins, and other components required for multiplication and growth of the host cell culture. Appropriate conditions include, for example, temperature, atmospheric conditions (e.g., level of oxygen, pressure), in addition to culture media. Culture conditions and media selection for host cells are described herein and in the art and are familiar to a person skilled in the art. Optimization of one or more culture conditions, media components, and optimization of times, times, temperature, and other conditions for culturing can be readily determined by persons skilled in the art who routinely practice cell culture methods.

Culturing of the host cell may be performed in a vessel of suitable size and composition (e.g., glass, metal, ceramic, polymer) for the particular host cell and that provides a suitable yield for the intended use. By way of non-limiting example, the bacteria culture may be grown in a vessel of a size suitable for analytical or research use or may be grown in a vessel of sufficient size that permits sufficient yield for performing animal and human trial studies as well as of sufficient size to provide for persons to be treated with the compound.

Production of a glycosphingolipid compound in a host cell can be monitored throughout the culture process by employing techniques described herein and in the art. When appropriate, typically at maximum yield of a compound, culturing of the host cells is terminated and the compound is isolated from the host cell culture. If the compound is secreted by the host cell, the compound can be isolated from the cell culture supernatant throughout the culturing process or at the end of the culturing process. More typically, the host cells are harvested (or isolated, separated) or in some manner obtained from the host cell culture and separated from the culture media by methods routinely practiced in the art (e.g., centrifugation, filtration). The compounds may be isolated from the host cells immediately or may be stored at an appropriate temperature (e.g., 4° C., −20° C., or −70° C.) and then isolated at a later time. The glycosphingolipid compound may be isolated from the host cells by extraction methods routinely practiced in the art, such as by extraction with one or more organic solvents (e.g., without limitation, a solution of chloroform and methanol). The compound present in the extract (e.g., the organic extract when the host cell culture is extracted with organic solvent(s)) may then be isolated by any one of several methods routinely practiced in the art for isolating lipid and glycosphingolipid compounds, including but not limited to, chromatography (e.g., thin layer chromatography, high pressure chromatography, ion exchange chromatography, and the like). Purity and molecular structure may then be determined by techniques and assays described herein with which a person skilled in the art is familiar. Exemplary analytical methods include NMR and mass spectrophotometry (for example, MALDI-TOF-MS).

In certain embodiments, the host cell is a prokaryotic cell, a yeast cell, or eukaryotic cell. In certain embodiments, the host cell is a prokaryotic cell that is a bacterial cell and in more particular embodiments, the bacterial cell is a species within the genus *Bacteroides*. In a more particular embodiment, the bacteria species is *Bacteroides fragilis*.

In another embodiment, the host cell may be engineered in a manner appropriate that results in an increase the yield of any one of the glycosphingolipid compounds described herein (see, e.g., Hancock et al., *Nat. Chem. Biol.* 5:508-14 (2009)). For example, a host cell may be transfected with a recombinant expression vector that encodes one or more enzymes, or other proteins, involved in the synthesis pathway of the glycosphingolipid compound. When the one or more enzymes or other proteins are expressed, synthesis and production of the compound by the cell is upregulated, resulting in an increased amount of the compound produced and isolated per cell cultured. Enzymes involved in the biosynthesis pathways of glycosphingolipids, such as bacterial glycosphingolipids, include members of the α-oxoamine synthase family (e.g., serine palmitoyltransferase), sphinganine kinase, 3-ketodihydrosphingosine reductase, and dihydroceramide synthase, and which each may be expressed by an expression vector introduced into a host cell. Without wishing to be bound by theory, a pyridoxal-phosphate-dependent α-oxoamine synthase that conjugates serine and a long-chain acyl-CoA to form 3-dehydrosphinganine may be the first committed step in the *Bacteroides* sphingolipid pathway.

Recombinantly expressed enzymes and polypeptides, encoded by nucleotide sequences available in the art, may be readily prepared using any of a variety of expression vectors known to those of ordinary skill in the art. Expression may be achieved in any appropriate host cell as discussed herein that has been transformed, transduced, or transfected with an expression vector containing a polynucleotide that encodes a recombinant enzyme or polypeptide and which polynucleotide also includes one or more regulatory expression sequences (such as promoter, enhancer, and the like) operatively linked to the encoding sequence portion of the polynucleotide. Persons skilled in the art can readily prepare recombinant expression vectors and perform recombinant expression of the polypeptide of interest using methods and techniques commonly and routinely practiced by persons skilled in the molecular biology art. See, e.g., Sambrook et al., Molecular Cloning: A Laboratory Manual, 3d edition, Cold Spring Harbor Laboratory Press, 2001; Ausubel et al., Current Protocols in Molecular Biology, 2003.

Accordingly, in certain embodiments, a method is provided for producing the compound of Formulae (I), (Ia), (II), (IIa) or (IIb) including all substructures and specific structures described herein, comprising (a) culturing bacteria that express the compound in a culture media to provide a bacterial culture; (b) obtaining the bacterial cells from the bacterial culture; and (c) isolating the compound from the bacterial cells. In more specific embodiments, the bacterial genus/species is *Bacteroides fragilis*.

Also provided herein are methods of manufacturing the pharmaceutical compositions described herein that comprise at least one of the glycosphingolipid compounds, as described herein. In one embodiment, the method of manufacture comprises chemical synthesis of the compound. Synthesis of one of more of the compounds described herein may be performed according to methods described herein and practiced in the art. In another embodiment, the compound is produced in a host cell as described above. In another embodiment, method of manufacture may further comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound (or alternatively isolating the compound from a host cell culture as described herein), formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Methods and Uses for Glycosphingolipid Compounds

Further provided herein is a method for activating a natural killer T cell (NKT cell), the method comprising contacting the NKT cell with the compound of Formulae (I), (Ia), (II), (IIa) or (IIb) including all substructures and specific structures described herein. In more specific embodiments, the compound is specifically bound to a CD1 protein. In still another embodiment, the compound of Formulae (I), (Ia), (II), (IIa) or (IIb) including all substructures and specific structures described herein, or a pharmaceutical composition comprising the compound, is for use in activating an NKT cell. In yet another embodiment, a use for the compound of Formulae (I), (Ia), (II), (IIa) or (IIb) including all substructures and specific structures described herein (or a pharmaceutical composition comprising the compound), is provided for the manufacture or preparation of a medicament or composition for activating an NKT cell.

Also provided herein is a method for treating a cancer in a subject, said method comprising administering to the subject a pharmaceutical composition including a compound of Formulae (I), (Ia), (II), (IIa) or (IIb) including all substructures and specific structures described herein. In still another embodiment, the compound of Formulae (I), (Ia), (II), (IIa) or (IIb) including all substructures and specific structures described herein, or a pharmaceutical composition comprising the compound, is for use in treating a cancer. In yet another embodiment, a use for the compound of Formulae (I), (Ia), (II), (IIa) or (IIb) including all substructures and specific structures described herein (or a pharmaceutical composition comprising the compound), is provided for the manufacture or preparation of a medicament or composition for treating a cancer.

In another embodiment, a method is provided for treating a microbial infection in a subject, wherein the method comprises administering to the subject a pharmaceutical composition including a compound of Formulae (I), (Ia), (II), (IIa) or (IIb) including all substructures and specific structures described herein. In more specific embodiments, the microbial infection is a viral infection, bacterial infection, fungal infection, or parasitic infection. In still another embodiment, the compound of Formulae (I), (Ia), (II), (IIa) or (IIb) including all substructures and specific structures described herein, or a pharmaceutical composition comprising the compound, is for use in treating the microbial infection. In yet another embodiment, a use for the compound of Formulae (I), (Ia), (II), (IIa) or (IIb) including all substructures and specific structures described herein (or a pharmaceutical composition comprising the compound), is provided for the manufacture or preparation of a medicament or composition for treating the microbial infection.

In still another embodiment, a method is provided for treating an autoimmune disease or disorder in a subject, wherein the method comprises administering to the subject a pharmaceutical composition including a compound of Formulae (I), (Ia), (II), (IIa) or (IIb) including all substructures and specific structures described herein. In still another embodiment, the compound of Formulae (I), (Ia), (II), (IIa) or (IIb) including all substructures and specific structures described herein, or a pharmaceutical composition comprising the compound, is for use in treating an autoimmune disease or disorder. In yet another embodiment, a use for the compound of Formulae (I), (Ia), (II), (IIa) or (IIb) including all substructures and specific structures described herein (or a pharmaceutical composition comprising the compound), is provided for the manufacture or preparation of a medicament or composition for treating an autoimmune disease or disorder.

In another embodiment, a method is provided for treating an immune disease or disorder in a subject, the method comprising (a) contacting a plurality of NKT cells with a compound of Formulae (I), (Ia), (II), (IIa) or (IIb) including all substructures and specific structures described herein to provide a plurality of activated NKT cells, and (b) administering the plurality of activated NKT cells to the subject. In more specific embodiments, prior to or concurrent with step (a), the compound is permitted to interact with a CD1 protein to form a compound:CD1 protein complex. In still another embodiment, the compound of Formulae (I), (Ia), (II), (IIa) or (IIb) including all substructures and specific structures described herein, or a pharmaceutical composition comprising the compound, is for use in treating an immune disease or disorder. In yet another embodiment, a use for the compound of Formulae (I), (Ia), (II), (IIa) or (IIb) including all substructures and specific structures described herein (or a pharmaceutical composition comprising the compound), is provided for the manufacture or preparation of a medicament or composition for treating an immune disease or disorder.

Also provided herein is a method for inducing an immune response in a subject, comprising administering to the subject a pharmaceutical composition including a compound of Formulae (I), (Ia), (II), (IIa) or (IIb) including all substructures and specific structures described herein, wherein the subject has or is suspected of having a microbial infection. In more specific embodiments, the microbial infection is a viral infection, bacterial infection, fungal infection, or parasitic infection.

Further provided herein is a method for inducing an immune response in a subject, comprising administering to the subject a pharmaceutical composition including a compound of Formulae (I), (Ia), (II), (IIa) or (IIb) including all substructures and specific structures described herein, wherein the subject has or is suspected of having a cancer.

A method is also provided for suppressing an immune response in a subject, comprising administering to the subject a pharmaceutical composition including a compound of Formulae (I), (Ia), (II), (IIa) or (IIb) including all substructures and specific structures described herein, wherein the subject has or is suspected of having an autoimmune disease. In more specific embodiments, the autoimmune disease is Type 1 diabetes mellitus.

As discussed in greater detail herein, also provided are pharmaceutical compositions comprising any one or more of the above-described glycosphingolipid compounds and (i.e., the compounds of structure I and substructures thereof and of structure II and substructures thereof, and specific compounds) and a pharmaceutically (i.e., physiologically) suitable (i.e., acceptable) excipient (such as a diluent, carrier, or adjuvant), which may be used in the methods described herein. These glycosphingolipid compounds having the structures are capable of activating (i.e., enhancing, stimulating) NKT cells (i.e., activating NKT cells in a statistically significant, clinically significant, and/or biologically significant manner) when the cells are contacted with the compound bound to a MHC Class I antigen-presenting protein, CD1. The murine CD1 protein is typically called mCD 1, and the human CD 1 protein is typically called CD1d or hCD1d. The CD1 proteins are located on the cell surface of antigen-presenting cells and when a glycosphingolipid compound described herein is permitted to interact with a CD1 protein (for example, with a CD1 protein present on an antigen-presenting cell), a CD1/glycosphingolipid complex is formed. Contact between the CD1/glycosphingolipid complex and NKT cell activates the NKT cell, which results, for example, in stimulating secretion of cytokines In other embodiments, the glycosphingolipid compounds and compositions comprising these compounds described above and herein may be used in methods for treating a disease, condition, or disorder that is treatable by activating NKT cells. By way of example, activation of NKT cells by these glycosphingolipid compounds may induce an immune response against a tumor cell and/or against a microorganism (e.g., a virus, bacterium, parasite, or fungus). In other embodiments, activation of NKT cells by these glycosphingolipid compounds may suppress the immune system in a manner that suppresses an autoimmune response (such as, but not limited to, diabetes). Each of these methods and uses is described in greater detail herein.

In one embodiment a method is provided for activating a natural killer T cell (NKT cell) by permitting interaction, under suitable conditions and for a time sufficient, between the NKT cell and any one or more of the compounds of Structure I or Structure II (or any substructure or specific structure described herein). The glycosphingolipid compounds having the structures I or II are capable of activating (i.e., enhancing, stimulating) NKT cells (i.e., activating NKT cells in a statistically significant, clinically significant, and/or biologically significant manner). In certain embodiments, methods are provided that comprise contacting a glycosphingolipid compound of Structure I or Structure II with an NKT cell (or plurality of NKT cells) (i.e., combining with, mixing with, exposing to, or in some manner permitting or facilitating interaction between the compound and NKT cell).

The method may further comprise, prior to or concurrent with contact of the compound with an NKT cell, combining the glycosphingolipid compound with (i.e., mixing, contacting, or in some manner permitting interaction with) a CD1 protein. The CD1 protein may be present on the cell surface of an antigen-expressing cell. The methods for activating an NKT cell may therefore comprise prior to or concurrent with contacting the compound and an NKT cell, contacting an antigen-presenting cell that expresses a CD1 protein on its cell surface and the compound. In other embodiments, the CD1 protein is isolated or purified (or partially purified) from the cell that expresses the protein. The CD 1 protein may be isolated from antigen-presenting cells that normally express CD1. Alternatively, the CD1 protein may be recombinantly expressed and isolated from a host cell culture. The CD1 protein may be a human CD1 protein, CD1d, or may be a CD1 protein obtained from another non-human mammal or other animal. Contacting of the CD1 protein and the glycosphingolipid compound permits formation of a CD1: glycosphingolipid compound complex by specific binding of the CD1 protein and the glycosphingolipid compound, which complex then interacts or contacts the NKT cell. When methods for activating NKT cells are performed in vivo in a host upon administration of any one of the glycosphingolipid compounds described herein, the CD1 protein is expressed on the cell surface of an antigen-presenting cell.

As discussed herein, the CD 1 proteins are cell surface glycoproteins and are antigen-presenting proteins that present lipid, glycolipid, or lipopeptide antigens to T cells (see, e.g., Brossay et al., *J. Immunol.* 161:5124-28 (1998)). CD1 proteins, such as the CD protein (i.e., human CD1) and murine CD1 protein are expressed in cells of hemopoietic lineage, including dendritic cells, macrophages, T cells, and B cells (see, e.g., Raghuraman et al., *J. Immunol.* 177:7841-48 (2006) and references cited therein). CD1 proteins present the lipid, glycolipid, or lipopeptide antigens to the set of T cells called natural killer T (NKT) cells. NKT cells are CD1-restricted, lipid antigen-reactive, immunoregulatory T lymphocytes that can promote (i.e., stimulate or enhance) cell-mediated immunity to tumor cells and to infectious disease organisms, including bacteria, viruses, parasites, and fungi. NKT cells can also suppress cell-mediated immunity that is associated with autoimmune disease and allograft rejection. See, for example, Godfrey et al., *Nat. Immunol.* 11:197-206 (2010).

CD1 bearing cells express a limited array of αβ T cell receptors (TCRs). Murine NKT cells are known to express an invariant Vα14-Jα18 TCR variant, and in humans, NKT cells express Vα24-Jα18 TCR. Therefore, these NKT cells are often called invariant NKT cells (iNKT cells). NKT may also be classified as Type 1 or Type 2 NKT cells. Type 1 NKT cells are also characterized by the capability to recognize the marine sponge-derived α-GalCer glycosphingolipid. Type 2 NKT cells express a more diverse αβ TCR repertoire and recognize some CD1-presented lipid antigens, but not α-GalCer. See Godfrey et al., *J. Exp. Med.* 208: 1121-25 (2011). Unless otherwise stated, NKT cells described herein that interact with the glycosphingolipid compounds are Type 1 NKT cells.

In one embodiment, methods for activating an NKT cell comprise administering the glycosphingolipid compound of structure I or structure II (or a substructure thereof or specific compound described herein) to a subject in need thereof. As discussed in greater detail herein, the glycosphingolipid compound is administered in a sufficient amount (i.e., dose) for a sufficient time via a suitable administration route to deliver a therapeutically effective dose of the compound. Formation of a CD1:glycosphingolipid compound complex (e.g., formation of a CD1d: glycosphingolipid compound complex in a human subject), therefore, occurs in vivo in the subject. Upon contact of the CD1:glycosphingolipid compound complex with an NKT cell (e.g., an iNKT cell), the NKT cell is activated. These activated NKT cells then produce cytokines, such as but not limited to, interferon (INF)-γ, interleukin (IL)-4, and/or IL-2. Production of the cytokines in turn activates other immune cells, such as dendritic cells, NK cells, B cells, and other populations of T cells (see, e.g., Bendelac et al., *Annu. Rev. Immunol.* 25:297-336 (2006); Van Kaer et al., *Curr. Biol.* 15:R429-R431 (2005)).

In another embodiment, a method is provided for treating or preventing (i.e., reducing the likelihood of occurrence) of a cancer in a subject, which method comprises administering to the subject in need thereof a therapeutically effective amount of one or more of the glycosphingolipid compounds of structure I or structure II (and substructures thereof and specific compounds). When the glycosphingolipid compound comes into contact with an antigen-presenting cell that expresses a CD1 protein on its cell surface, the compound and CD1 form a complex that is capable of activating NKT cells (e.g., iNKT cells). The activated NKT cells stimulate, induce, or enhance an immune response (e.g., an innate or non-specific, antigen-independent immune response) against the cancer cells (i.e., tumor cells, malignant cells). Accordingly, in other embodiments, methods are provided herein for inducing an innate immune response in a subject which methods comprise administering one or more of the glycosphingolipid compounds described herein to a subject who has or is suspected of having a cancer. Because the immune response induced by the compounds described herein is non-specific (i.e., antigen-independent) rather than an immune response specific for a particular tumor antigen or tumor-associated antigen, the compounds may be used for inducing an immune response that is effective against any cancer or tumor cell.

Cancers that may be treated by the methods described herein include but are not limited to cancers of the colon, breast, lungs, prostate, pancreas, liver, bone, brain, ovaries, testes, uterus, kidney, bladder, skin, throat, salivary glands, stomach, and cervix. In other embodiments, the methods may be used for treating myeloma, melanoma, mesothelioma, lymphomas (e.g., B cell lymphoma, Hodgkin's and non-Hodgkin's lymphoma), and leukemias.

Induction of an innate immune response (or non-specific, antigen-independent immune response) in a host by administering a glycosphingolipid compound described herein may delay onset of a cancer in a subject; decrease or attenuate (i.e., retard, slow, inhibit) rate of growth of a tumor; decrease (i.e., retard, slow, inhibit) metastasis of a tumor; or decrease the severity of one or more symptoms of the disease. Induction of an innate immune response and activation of immune cells and expression of immune modulators can also contribute to induction and optimization of an adaptive (i.e., specific) immune response against one or more tumor antigens or tumor-associated antigens.

In another embodiment, a method is provided herein for treating or preventing (i.e., decreasing the likelihood of occurrence) of a microbial infection by administering to the subject in need thereof, a therapeutically effective amount of one or more of the glycosphingolipid compounds of structure I or structure II (and substructures thereof and specific compounds). When the glycosphingolipid compound comes into contact with an antigen-presenting cell that expresses a CD1 protein on its cell surface, the compound and CD1 form a complex that is capable of activating NKT cells (e.g., iNKT cells). The activated NKT cells stimulate, induce, or enhance an immune response (i.e., an innate or non-specific, antigen-independent immune response) against the microorganism causing the infection. Accordingly, in other embodiments, methods are provided herein for inducing an innate immune response in a subject which methods comprise administering one or more of the glycosphingolipid compounds described herein to a subject who has or is suspected of having a microbial infection. The microbial infection may be caused by a virus, bacteria, fungus, or parasite. Because the immune response induced by the compounds described herein is non-specific (i.e., antigen-independent) rather than an immune response specific for a particular microbial antigen, the compounds may be used for inducing an immune response that is effective against any microorganism.

Induction of an innate immune response (or non-specific, antigen-independent immune response) in a host by administering a glycosphingolipid compound described herein may delay onset of symptoms of a disease in a subject who has been exposed to a microorganism, decrease the severity of one or more symptoms of the infection, and/or decrease or attenuate the severity of the infection (i.e., decrease the length of time that the host or subject presents symptoms and/or sequelae of the infection; decrease, attenuate, or mitigate one or more sequelae of the infection) (see, e.g., Selin, *J. Immunol.* 166:6784-94 (2001)). Induction of an innate immune response and activation of immune cells and expression of immune modulators can also contribute to induction and optimization of an adaptive (i.e., specific) immune response. See, e.g., Takeuchi et al., *Immunol. Rev.* 227:75-86 (2009); Koyama et al., *Cytokine* 43:336-41 (2008) Epub 2008 Aug. 9; Diacovich et al., *Nature Reviews Microbiology* 8:117-28 (2010).

In certain embodiments, the microorganism is a bacterial species. The bacteria causing the infection or that is likely to cause the infection may be a pathogen or an opportunistic pathogen. The methods described herein may be used for treating or preventing an infection caused by either Gram-negative bacteria or Gram-positive bacteria. Gram-negative bacteria that may cause an infection treatable by administering the compounds described herein include, but are not limited to, the following genera: *Acinetobacter, Actinobacillus, Bordetella, Brucella, Campylobacter, Cyanobacteria, Enterobacter, Erwinia, Escherichia* (e.g., *E. coli*), *Franciscella, Helicobacter, Hemophilus* (e.g., *H. influenzae*), *Klebsiella, Legionella, Moraxella, Neisseria, Pasteurella, Proteus, Pseudomonas, Salmonella, Serratia, Shigella, Treponema, Vibrio,* and *Yersinia.* Gram-positive bacteria that may cause an infection treatable by administering the compounds described herein include, but are not limited to, the following genera: *Streptococcus* (e.g., *S. pyogenes* (group A *streptococcus*), *S. agalactiae* (group B *streptococcus*), *S. pneumoniae*), *Staphylococcus, Enterococcus, Listeria, Clostridium,* and *Bacillus* (e.g., *B. anthracis*). Other bacteria called actinobacteria that may cause an infection treatable by administering the compounds described herein include, but are not limited to, the following genera: *Mycobacterium, Corynebacterium,* and *Nocardia*.

The microorganism may be a virus, which includes, but is not limited to, a virus of one of the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. The methods described herein may therefore be useful for inducing innate immunity against infection caused a virus, such as Human Deficiency Virus (HIV) (see, e.g., Borrow et al., *Retrovirology* 7:84 (2010) and Morgenson et al., *Retrovirology* 7:54 (2010) for a discussion of the importance of innate immune to outcome of HIV infection); a vaccinia virus; a varicella virus; an influenza virus; a hepatitis virus; Respiratory Syncytial Virus; a herpes virus. The methods described herein may also be useful for inducing an innate immune response against a microorganism that is a yeast, or fungus (for example, *Candida albicans*). The methods may also be useful for inducing innate immunity that is effective against parasites (e.g., a *Plasmodium* species that causes malaria; *Leishmania* species; trypanosomes) (see, e.g., McGuinness et al., *Trends in Parasitology* 19:312-19 (2003)).

In another embodiment, a method is provided for treating or preventing (i.e., reducing the likelihood of occurrence) of an autoimmune disease. Autoimmune diseases such as diabetes (particularly Type 1 diabetes), inflammatory bowel disease, lupus erythematosus, rheumatoid arthritis, and psoriasis may be treated by administering to a subject in need thereof a glycosphingolipid compound described herein.

The immunomodulatory effect of glycosphingolipids compounds described herein when administered to a subject who has an autoimmune response act to suppress the immune response. Suppression of an immune response that is an autoimmune response in a host by administering a glycosphingolipid compound described herein may delay onset of an autoimmune disease (e.g., diabetes, inflammatory bowel disease, lupus erythematosus, rheumatoid arthritis, psoriasis) in a subject; decrease or attenuate (i.e., retard, slow, inhibit) the severity of the autoimmune disease; or decrease the severity of one or more symptoms of the disease. Without wishing to be bound by theory, aberrant regulation of the innate immune system may contribute to development of an autoimmune disease (see, e.g., Kim et al., *Curr. Mol. Med.* 9:30-44 (2009)). Accordingly, by administering to a subject in need thereof a glycosphingolipid compound described herein that suppresses an autoimmune response may be useful for treating or slowing or preventing the onset of the autoimmune disease (e.g., diabetes), the severity of symptomatology of the disease, and/or the sequelae of the disease.

In certain particular embodiments, methods are provided herein for treating diabetes mellitus type 1 (Type 1 diabetes, which is also called T1DM, IDDM) by administered a glycosphingolipid compound described herein. Type 1 diabetes is a form of diabetes mellitus that results from autoimmune destruction of insulin-producing beta cells of the pancreas. Type 1 diabetes is typically treated by daily insulin injections, which can be burdensome for subjects. The methods described herein may therefore provide an alternative or adjunct therapy for managing the disease. The effect of a treatment can be monitored by determining blood glucose and/or insulin levels in the subject. Methods and techniques for monitoring blood glucose and insulin levels in a subject are routinely practiced in a clinical laboratory by persons skilled in medical and/or clinical arts.

In another embodiment, a method is provided for treating an immune disease or disorder (e.g., an autoimmune disease or disorder) in a subject who has or who is at risk of developing the immune disease or disorder comprising first contacting a glycosphingolipid compound described herein (or a pharmaceutical composition comprising the compound) and the plurality of NKT cells. Prior to or concurrent with combining the NKT cells and the compound, the compound is contacted with an antigen-presenting cell that expresses a CD1 protein (e.g., human CD1, CD1d) on its cell surface, which permits formation of a CD1:compound complex. Recognition and specific binding of the CD1:compound complex by the NKT cells results in activation of the NKT cells. The method further comprises administering the activated NKT cells to the subject. Techniques for administering immune cells to a subject have been long practiced in the art.

A plurality of NKT cells may be obtained from the subject (autologous donor) or from another person (allogenic donor). The non-self or allogenic donor is selected by determining the histocompatibility of the donor and subject NKT cells. Sufficient histocompatibility matching of the donor NKT cells is typically determined by human leukocyte antigen (HLA) typing, which is routinely performed by persons skilled in the transplant art.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide at least one glycosphingolipid compound in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of a glycosphingolipid compound in treating or preventing a disease or disorder or condition described herein, and determining and adjusting an appropriate dosing regimen (e.g., adjusting the amount of compound per dose and/o number of doses and frequency of dosing), can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject.

The immunological status, including the presence, level, or extent of the innate immune response, of a subject before, during, and after treatment with a glycosphingolipid compound (or composition comprising the compound) described herein may be monitored. Induction and production of cytokines and other immune modulators can be determined by methods and techniques routinely practiced in the art for determining the level of immune modulators and cytokines in a biological sample obtained from the subject before, during, and after treatment. An immune response, including activation and proliferation of immune cells, particularly NKT cells, in a subject may be determined by any number of well-known immunological techniques and methods with which those having ordinary skill in the art will be readily familiar. Such assays include, but need not be limited to, in vivo or in vitro determination of the presence or level of one or more cytokines (e.g., IFN-γ, IL-2, IL-4, and IL-12, and also IL-6, IL-1β, leukemia inhibitory factor, TNF-α, IL-10), lymphokines, chemokines, hormones, growth factors, and the like. By way of example, the exemplary glycosphingolipid α-GalCer$_{Bf}$ described herein stimulates production of IL-2 and IFN-γ by NKT cells. Stimulation of NKT cells may also, in turn, induce production of activation markers, CD25 and CD69, the levels of which can also be determined by immunodetection methods routinely practiced in the art. Cellular activation state changes may also be determined, for example, by determining altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays may be found, for example, in Lefkovits (*Immunology Methods Manual: The Comprehensive Sourcebook of Techniques*, 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998)) and references cited therein.

A "biological sample" may include a sample from a subject, and may be a blood sample (from which serum or plasma may be prepared), a biopsy specimen, one or more body fluids (e.g., lung lavage, ascites, mucosal washings, synovial fluid), bone marrow, lymph nodes, tissue explant, organ culture, or any other tissue or cell preparation from the subject or a biological source. A biological sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

In another embodiment, a method is provided for activating NKT cells in vitro, which method comprises contacting the NKT cells and a glycosphingolipid compound (I.e., mixing, combining or in some manner permitting the NKT cells and the compound to interact). Prior to or concurrent with the step of contacting the NKT cells and the compound, the compound is contacted with a CD1 protein (i.e., mixed, combined with, or by some manner permitting the CD1 protein and the compound to interact) to form a CD1: glycosphingolipid compound complex. Such assays and techniques may be used to determine the capability of a glycosphingolipid compound to activate NKT cells. The in vitro methods for activating an NKT cell comprise contacting one or more glycosphingolipid compounds with an isolated CD1 protein or with antigen-presenting cells that express a CD1 protein on the cell surface (i.e., a source of a CD1 protein, including a biological sample) under conditions and for a time sufficient to permit the glycosphingolipid compound and the CD1 protein to interact and form a glycosphingolipid compound:CD1 complex. As described herein, upon contact and interaction of the glycosphingolipid compound:CD1 complex with NKT cells, the NKT cells are activated. These assay methods may be employed for characterizing the glycosphingolipid compounds described herein, or for identifying and characterizing glycosphingolipid compound derivatives, for monitoring pharmacokinetics of a glycosphingolipid compound administered to a subject in pre-clinical (such as animal studies) or clinical studies in humans, as well as quality assurance and quality control assays performed during manufacturing and production of the compound.

For in vitro and certain embodiments of in vivo methods described herein, the source of the CD1 protein may be a biological sample that comprises immune cells, including antigen presenting cells, for example, a dendritic cell or a macrophage, that express CD1 on the cell surface. Alternatively, the CD1 protein, such as CD1d or mCD1, may be purified or isolated from a cell, such as an antigen presenting cell, or may be recombinantly expressed in a host cell using recombinant expression methods described herein and routinely practiced in the art. The host cells may be cultured and the CD1 protein isolated from the host cell culture using any one of a number of protein purification methods routinely practiced by a person skilled in the art (e.g., ion exchange chromatograph, affinity chromatography, high pressure liquid chromatography, size exclusion chromatography, or other methods). When an isolated CD1 protein is permitted to contact a glycosphingolipid compound described herein, the CD 1 protein, such as human CD1d, may be in the form of a tetramer.

These methods may further comprise adding or including immune cells that can be induced to produce cytokines when NKT cells are activated. Exemplary techniques for determining the level of activity of a glycosphingolipid compound include techniques described herein and practiced in the art, such as NKT hybridoma cell stimulation. NKT hybridoma cells can be cultured with immune cells, such as bone marrow derived dendritic cells, and then contacted with a glycosphingolipid compound. The level of a cytokine (e.g., IL-2, IL-4, IFN-γ) can then be determined and compared with the level of cytokine production in appropriate negative controls. Cytokines can be measured by any number of methods routinely practiced in the art, such as immunoassays that detect the presence of a particular cytokine using an antibody that specifically binds to the cytokine of interest. Characterizing the activity of a glycosphingolipid compound may also be determined in art-accepted animal models (see, e.g., as Example 7 herein). The capability of a glycosphingolipid compound to effectively treat a subject can also be assessed in an animal model for the particular disease, disorder, or condition. Numerous animal models are available in the art for determining the anti-tumor activity of compounds. Other animal models are available for determining the capability of the compound to protect animals against infection by an infectious disease microorganism. Still different animal models have been developed for determining the effectiveness of a compound for treating autoimmune diseases (e.g., a cyclophosphamide-induced diabetes mouse model).

Conditions for a particular assay include temperature, buffers (including salts, cations, media), and other components that maintain the integrity of any cell used in the assay and the compound, which a person skilled in the art will be familiar and/or which can be readily determined. A person skilled in the art also readily appreciates that appropriate controls can be designed and included when performing the in vitro methods and in vivo methods described herein.

Pharmaceutical Compositions and Methods of Using Pharmaceutical Compositions

Also provided herein are pharmaceutical compositions that comprise any one or more of the glycosphingolipid compounds of structure I and structure II (and substructures and specific structures thereof). The compounds described herein may be formulated in a pharmaceutical composition for use in activating NKT cells and in treatment or preventive (or prophylactic) treatment (e.g., reducing the likelihood of occurrence or of exacerbation of a disease, disorder, or condition or of one or more symptoms of the disease). The diseases, disorders, and conditions treatable by administering a glycosphingolipid compound described herein include those diseases, disorders, and conditions for which activation of NKT cells and subsequent immune response resulting from activation of NKT cells provides a beneficial effect.

In pharmaceutical dosage forms, any one or more of the compounds of structure I and structure II, substructures, and specific structures described herein may be administered in the form of a pharmaceutically acceptable derivative, such as a salt, or they may also be used alone or in appropriate association, as well as in combination, with other pharmaceutically active compounds. The methods and excipients described herein are exemplary and are in no way limiting. An effective amount or therapeutically effective amount refers to an amount of a compound or a composition comprising one or more compounds that when administered to a subject, either as a single dose or as part of a series of doses, is effective to produce a desired therapeutic effect.

Optimal doses may generally be determined using experimental models and/or clinical trials. The optimal dose may depend upon the body mass, weight, or blood volume of the subject. In general, the amount of a compound described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a compound or of a composition comprising at least one of the compounds described herein for treating a disease or condition may depend upon the subject's condition, that is, stage of the disease, severity of symptoms caused by the disease, general health status, as well as age, gender, and weight, and other factors apparent to a person skilled in the medical art. Similarly, the dose of the compound for treating a disease or disorder treatable by activating NKT cells, as described herein, may be determined according to parameters understood by a person skilled in the medical art.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least one compound as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein that comprise at least one of the glycosphingolipid compounds of structure I and structure II (and substructures and specific structures thereof) may be administered to a subject in need by any one of several routes that effectively deliver an effective amount of the compound. Such administrative routes include, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. Compositions administered by these routes of administration and others are described in greater detail herein.

A pharmaceutical composition comprising a glycosphingolipid compound described herein may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, $21^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, at least one of the compounds described herein can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

A composition comprising any one of the compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The glycosphingolipid compounds described herein can be formulated in pharmaceutical compositions as suppositories by mixing with a variety of bases such as emulsifying bases or water-soluble bases. These compounds may be administered rectally via a suppository. The suppository can include vehicles such as cocoa butter, carbowaxes and polyethylene glycols, which melt at body temperature, yet are solidified at room temperature.

The glycosphingolipid compounds described herein may be used in aerosol formulation to be administered via inhalation. The compounds may be formulated into pressurized acceptable propellants such as dichlorodifluoromethane, propane, nitrogen and the like.

Any one or more of the glycosphingolipid compounds described herein may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a glycosphingolipid compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5):655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., *Urology* 2001; 57(2):301-5; Kiijavainen et al., *Eur. J. Pharm. Sci.* 2000; 10(2):97-102; and Tenjarla et al., *Int. J. Pharm.* 1999; 192(2):147-58.

When a glycosphingolipid compound is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. A glycosphingolipid compound may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Other embodiments and uses will be apparent to one skilled in the art in light of the present disclosures. The following examples are provided merely as illustrative of various embodiments and shall not be construed to be limiting in any way.

EXAMPLES

The following materials and methods were used in the examples described herein.

Example 1

Construction of a Sphingolipid-Deficient *B. fragilis* Mutant

A sphingolipid-deficient mutant of *B. fragilis* was prepared so that sphingolipids produced by a *B. fragilis* wild-type strain and mutant strains could be compared.

A sphingolipid-deficient mutant of *B. fragilis* strain NCTC 9343 (see, e.g., Cerdeño-Tárraga et al., *Science* 307:1463-65 (2005)) was prepared. *B. fragilis* NCTC 9343 is a human gut isolate, and the genome of this strain has been sequenced. However, the genes in the *Bacteroides* sphingolipid pathway had not been identified. Based on an hypothesis that the *Bacteroides* pathway would harbor homologs of the eukaryotic pathway (see, e.g., Ikushiro et al., *J Bacteriol* 189:5749-61 (2007)), BLAST searches of the *B. fragilis* genome using the *Saccharomyces cerevisiae* sphingolipid biosynthetic enzymes as queries yielded two hits encoded by adjacent genes: BF2461, a putative serine palmitoyltransferase, and BF2462, a putative sphinganine kinase.

A mutant was constructed that harbored a clean deletion of BF2461 (Δ2461). *Bacteroides* strains (either the parental strain or deletion mutant strains) were grown anaerobically in basal medium or on brain-heart infusion plates supplemented with hemin (50 μg/ml) and vitamin $K_1$ (0.5 μg/ml) (BHIS plates), with gentamicin (200 μg/ml) and erythromycin (5 μg/ml) added when appropriate. *E. coli* DH5α that contained recombinant plasmids was grown in L broth or on L agar plates containing kanamycin (50 μg/ml).

Creation of the deletion mutant involved PCR amplification of DNA flanking each side of the region to be deleted, digestion of these products with restriction enzymes using sites engineered into the primers (called LF_5'; LF_3'; RF_5'; RF_3'; see Table 1), and three-way ligation into SstI or BamHI site of the *Bacteroides* conjugal suicide vector pNJR6. The resulting plasmid in *E. coli* DH5α was conjugally transferred into *B. fragilis*, and co-integrates were selected by Em$^r$. Co-integrates were passaged, plated on nonselective medium, and then replica plated to medium containing erythromycin. Em$^s$ colonies were screened by PCR to detect those that acquired the mutant genotype. The BF2461 deletion mutant was constructed so that 1,078 by of the 1,185-bp gene was deleted.

TABLE 1

Primers

| Primer | Sequence$^a$ | Comments |
|---|---|---|
| 2461_LF_5' | 5'-CCTT<u>GAGCTC</u>CAGTTCG ATATTACGGATCACCTT-3' (SEQ ID NO: 1) | ΔBF2461- left flanking region-5' |
| 2461_LF_3' | 5'-CTGC<u>ACGCGT</u>TATACGC CTTTAGCCTTTATCTGC-3' (SEQ ID NO: 2) | ΔBF2461- left flanking region-3' |
| 2461_RF_5' | 5'-GGCA<u>ACGCGT</u>AAGTTAG TGAAATGTTTCAAGGCA-3' (SEQ ID NO: 3) | ΔBF2461- right flanking region-5' |
| 2461_RF_3' | 5'-TTTG<u>GAGCTC</u>TTCAATA GTGTAGGAAGCGTTTTG-3' (SEQ ID NO: 4) | ΔBF2461- right flanking region-3' |

$^a$Restriction sites are indicated by underlining.

Figure 2:
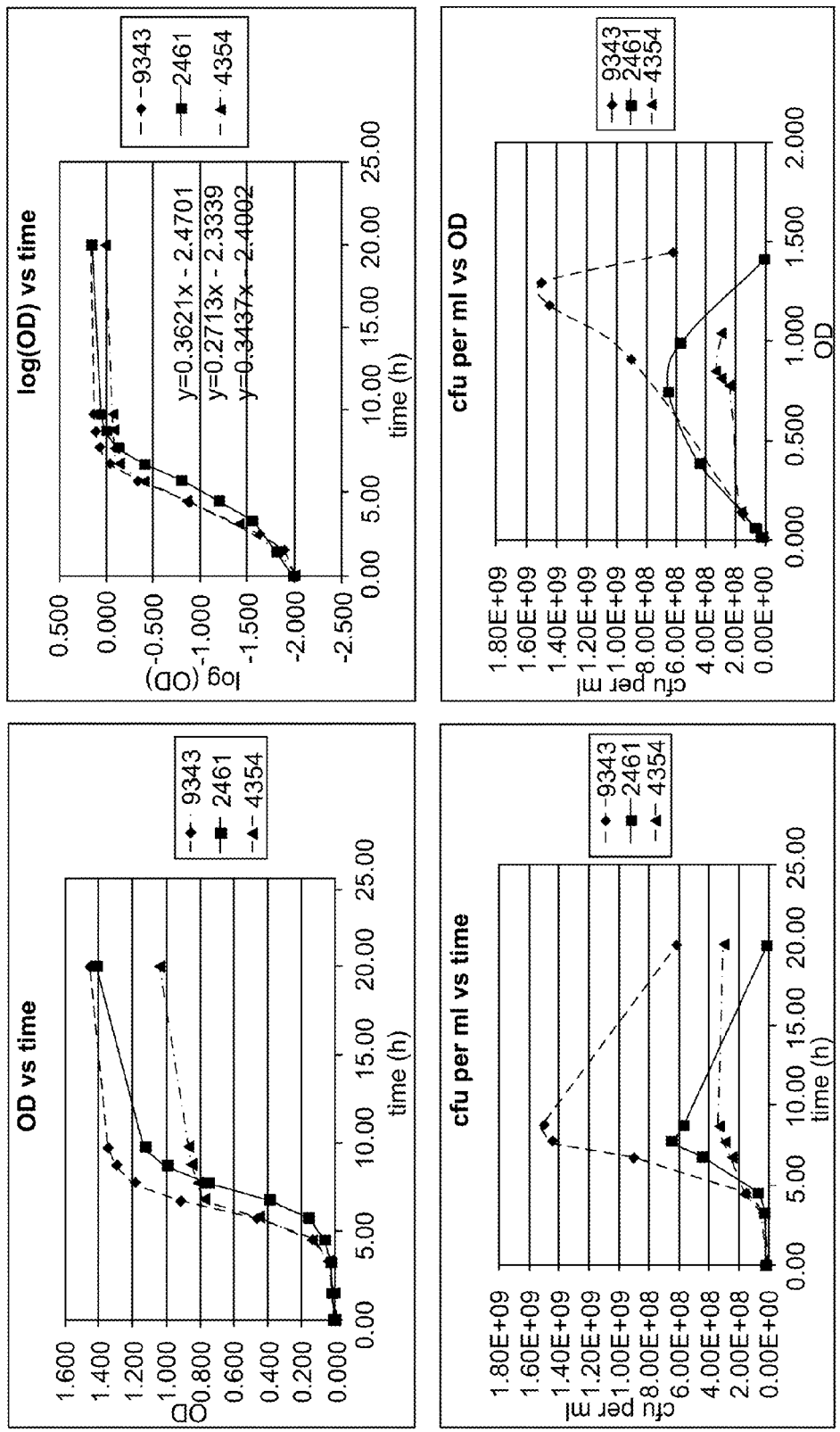
FIG. 2 illustrates growth measurements for *B. fragilis* strain NCTC 9343 and mutant strains, ΔBF2461 and ΔBF4354.

Growth measurements of the ΔBF2461 mutant and another mutant called 4354 were compared with *B. fragilis* NCTC 9343 wild-type strain. The three strains were cultured by inoculating 100 mL basal medium with growth from a freshly inoculated BHIS plate to an $OD_{600}$ of 0.01. The optical density at 600 nm ($OD_{600}$) was recorded at regular intervals, and CFU/mL was determined at each time point. The data are shown in FIG. 2.

Because the yeast homolog of BF2461 constitutes the entry point to the sphingolipid pathway, the Δ2461 mutant provided an ideal starting point for enumerating the *B. fragilis* sphingolipids. Bioinformatics analysis suggested that BF2461, like its yeast homolog, is a pyridoxal-phosphate-dependent α-oxoamine synthase that conjugates serine and a long-chain acyl-CoA to form 3-dehydrosphinganine as the first committed step in the *Bacteroides* sphingolipid pathway. Therefore, the Δ2461 mutant was expected to be completely deficient in the production of sphingolipids.

Example 2

Isolation and Characterization of *B. fragilis* Sphingolipids

To identify and characterize sphingolipids produced by *B. fragilis*, a chromatographic comparison of lipid extracts from wild-type and mutant strains was performed. Briefly, *B. fragilis* NCTC9343 was cultured under standard conditions, and harvested cells were extracted with $CHCl_3$:MeOH (2:1). The organic extract was subjected to alkaline hydrolysis, neutralized, and extracted with $CHCl_3$:MeOH (2:1). The crude extract was purified by preparative TLC($CHCl_3$:MeOH:H2O, 65:25:4) to give α-GalCer$_{Bf}$ (Rf=0.6). These procedures are described in greater detail below.

Materials, General Methods, and Instrumentation Used in Sphingolipid Isolation and Purification. All solvents were purchased from Sigma-Aldrich (St. Louis, Mo.) unless otherwise noted. Low-resolution LC-MS analysis was carried out on an Agilent 6130 LC/MS using a Phenomenex Gemini-NX 5 μm C18 110 Å 100×2 mm column at 0.7 ml/min. High-resolution LC-MS data was collected in negative ion mode, on an Agilent 6520 Accurate-Mass Q-TOF Mass Spectrometer fitted with an electrospray ionization (ESI) source. The capillary voltage was set to 3500 kV, and the fragmentor voltage at 125 V. The drying gas temperature was maintained at 320° C. with a flow rate of 12 L/min and a nebulizer pressure of 45 psi. HPLC separation was effected on a Gemini-NX C18 reverse phase column (5 μm, 110 Å, 2.0×50 mm, Phenomonex, Torrance, Calif.). Compounds were eluted at 0.5 ml/min in a gradient of solvents A (0.1% $NH_4OH$ in water) and B (0.1% $NH_4OH$ in methanol): 65% B increasing to 100% B over 30 min., isocratic at 100% B for 1 min before returning to 65% B and re-equilibrating over 3 min. High resolution mass spectrometry (HRMS) was carried out at the WM Keck Foundation Biotechnology Resource Laboratory at Yale University on a Bruker 9.4T FT-ICR MS. Infrared (IR) spectra are recorded on a Perkin Elmer 781 spectrophotometer, $\lambda_{max}$ in $cm^{-1}$. Bands are characterized as broad (br), strong (s), medium (m) or weak (w). $^1$H NMR spectra were recorded on a Varian Unity 600 MHz spectrometer. Chemical shifts are reported in ppm from tetramethylsilane with the solvent resonance resulting from incomplete deuteration as the internal standard ($CDCl_3$: δ 7.26, $CD_3OD$: δ 3.31, DMSO: δ 2.50, pyridine: δ 8.74). Data are reported in table form as follows: chemical shift, multiplicity (s=singlet, d=doublet, t=triplet, q=quartet, br=broad, m=multiplet), coupling constants, and integration. $^{13}$C NMR spectra were recorded on a Varian Unity 400 MHz spectrometer (100 MHz) with complete proton decoupling. Chemical shifts are reported in ppm from tetramethylsilane with the solvent resonance as the internal standard ($CDCl_3$: δ 77.16, $CD_3OD$: δ 49.00, DMSO: δ 39.52). Optical rotations were measured on a Perkin Elmer 241 Polarimeter. Unless otherwise noted, all solvents and reagents were purchased from VWR or Fisher and used without further purification. An anaerobic environment was achieved by three methods, and all were equally effective and used interchangeably: 1) Coy Laboratory Products anaerobic chamber; 2) BD GasPak™ EZ Gas Generating Container System; 3) Mitsubishi Gas Chemical Co. AnaeroPack™ System.

Purification of Sphingolipids and Free Ceramide from *B. fragilis* NCTC 9343. *B. fragilis* NCTC 9343 was allowed to grow under an anaerobic atmosphere in basal medium (4.5 L) supplemented with hemin (50 μg/ml) and vitamin $K_1$ (0.5 μg/ml) at 37° C. for 2 days. The cells were harvested by centrifugation and extracted with $CHCl_3$:MeOH (2:1, 1.5 L). The organic extract was filtered and concentrated, then re-dissolved in $CHCl_3$:MeOH (2:1, 100 ml) and treated with NaOH (0.5 N, 100 ml). The suspension was allowed to stir at 37° C. for 1 h, then brought to pH 2-4 with 10% HCl. The aqueous layer was extracted with $CHCl_3$:MeOH (2:1, 3×500 ml). The organic layers were combined, dried ($Na_2SO_4$), and then concentrated to give 0.5 g crude extract.

Figure 3A:
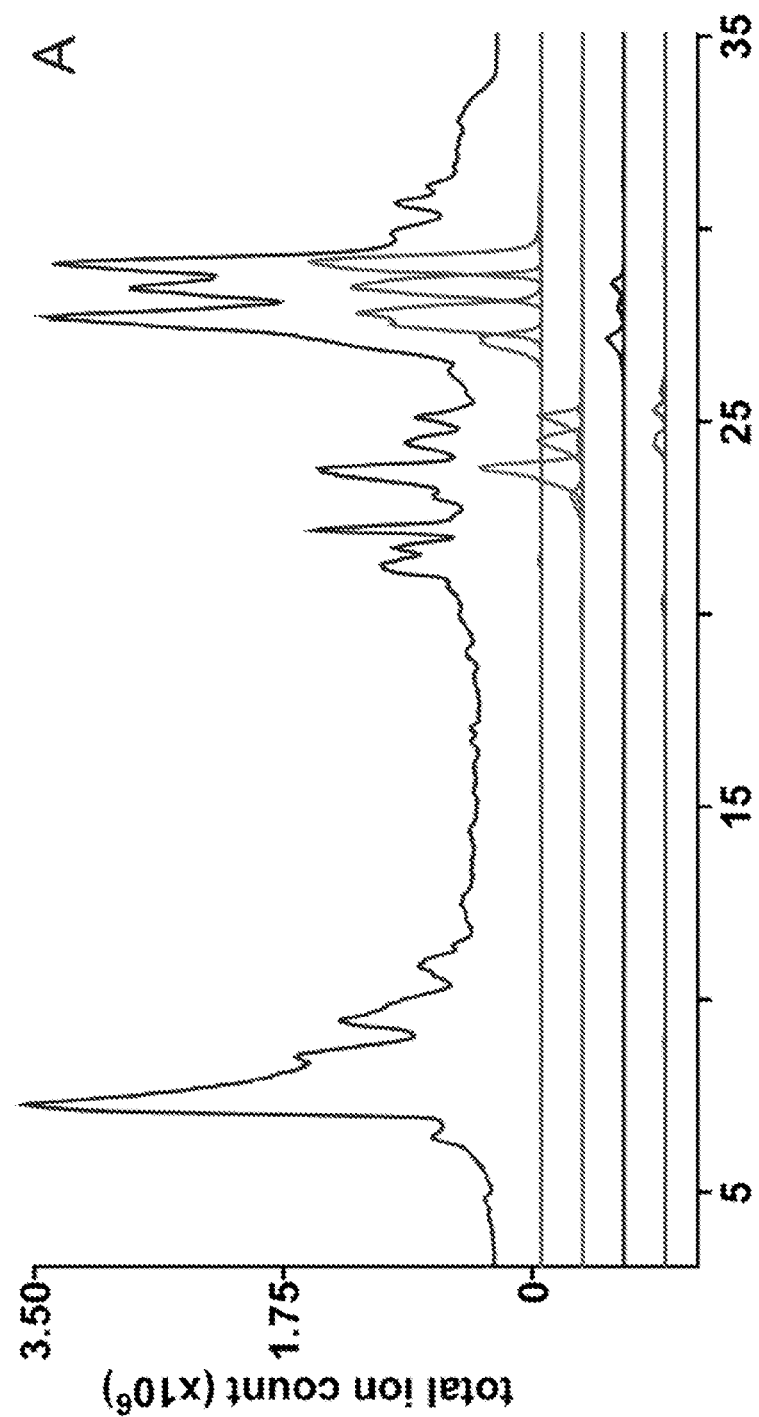
FIGS. 3A and 3B present LC-MS traces of crude lipid extracts of wild-type *B. fragilis* (FIG. 3A) and the sphingolipid-deficient mutant ΔBF2461 (FIG. 3B). The traces shown are the total ion count (uppermost trace) and in descending order from the total ion count toward the x-axis, the extracted ion traces of sphingolipid masses for ceramide (m/z [M−H]: 540.5, 554.5, 568.5, 582.6); CPE (m/z [M−H]: 663.5, 677.5, 691.5, 705.5); α-GalCer$_{Bf}$(m/z [M−H]: 702.6, 716.6, 730.6, 744.6); and phosphatidylethanolamine (m/z [M−H]: 648.5, 662.5, 676.5, 690.5).
Figure 3B:
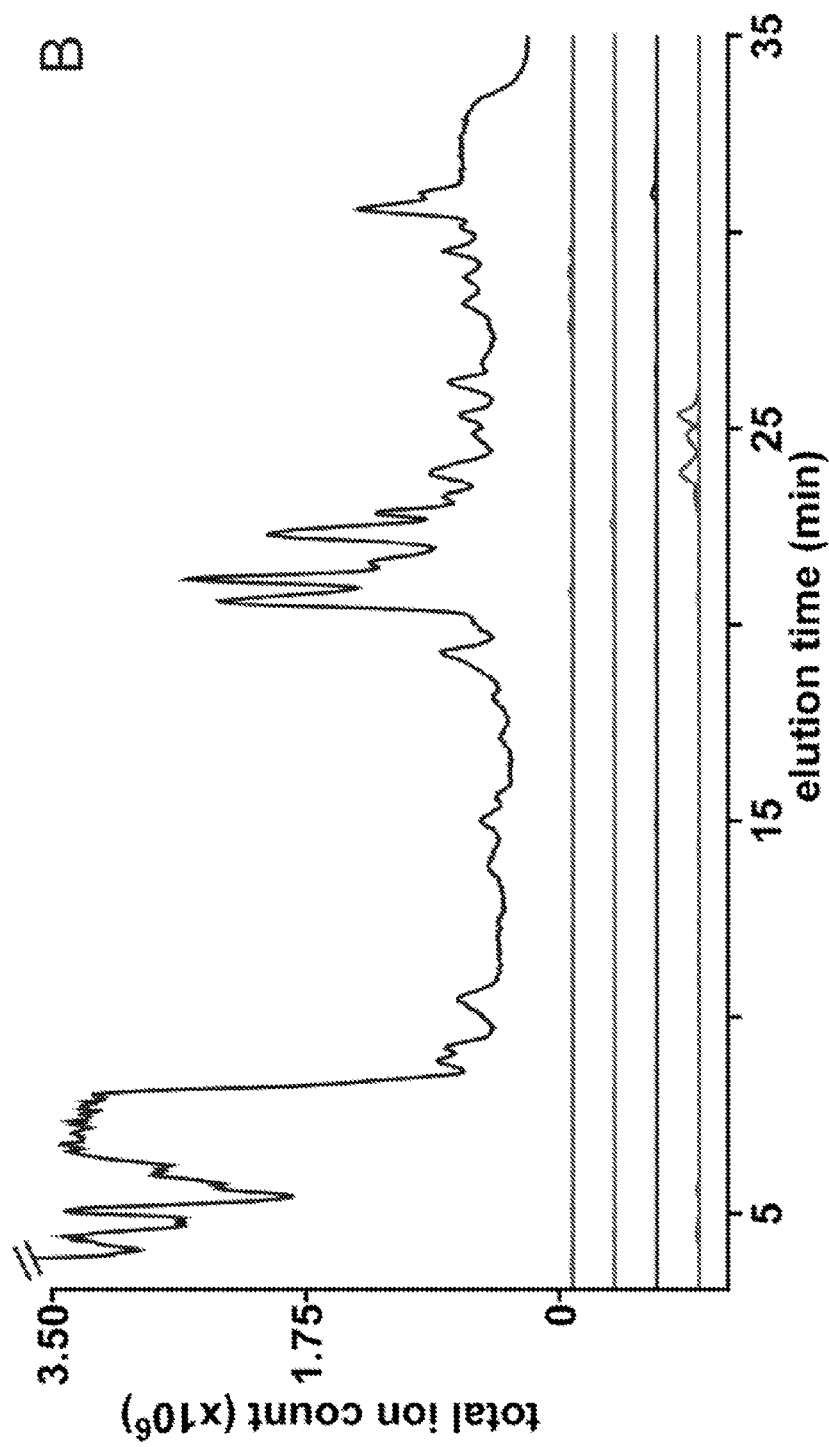

Comparative HPLC-ELSD analysis of alkaline-stable lipid extracts from the wild-type (WT) and Δ2461 strains revealed three primary peaks that were present in the WT but not the Δ2461 extract as shown in FIG. 3. The traces shown are the total ion count (uppermost trace) and in descending order from the total ion count toward the x-axis, the extracted ion traces of sphingolipid masses for ceramide (m/z [M−H]: 540.5, 554.5, 568.5, 582.6); CPE (m/z [M−H]: 663.5, 677.5, 691.5, 705.5); α-GalCer$_{Bf}$(m/z [M−H]: 702.6, 716.6, 730.6, 744.6); and phosphatidylethanolamine (m/z [M−H]: 648.5, 662.5, 676.5, 690.5). Peaks corresponding to the three sphingolipids, but not the phospholipid phosphatidylethanolamine, are absent in *B. fragilis* Δ2461.

The crude extract was dissolved in a minimum amount of $CHCl_3$:MeOH (2:1), applied to a 2 mm preparative TLC plate, and eluted with $CHCl_3$:MeOH:AcOH:$H_2O$ (100:20:12:5). The plate was divided into three section based on polarity (top, middle, and bottom). Each section was scraped off the plate and extracted with $CHCl_3$:MeOH (5:1). The resulting solution was concentrated and further purified by preparative TLC (0.5 mm): the top section was eluted in $CHCl_3$:MeOH:$NH_4OH$ (95:5:0.8) to give purified ceramide (see, e.g., Miyagawa et al., *J. Gen. Appl. Microbiol.* 24:341-48 (1978)) (11.4 mg, white solid, Rf=0.3). The middle section was eluted in $CHCl_3$:MeOH:$H_2O$ (first in 88:12:0.5, then in 65:25:4) to give α-galactosylceramide (α-GalCer$_{Bf}$; 2.7 mg, glass, Rf=0.6 in 65:24:4). The bottom section was eluted in $CHCl_3$:MeOH:AcOH:$H_2O$ (100:20:12:5) to give purified ceramide phosphorylethanolamine (CPE; 4.2 mg, white solid, Rf=0.2). Each compound was isolated as a mixture of compounds with varying lipid chain lengths and was not further separated.

Preparative TLC was used to purify multi-milligram quantities of these compounds, and HPLC-MS analysis of the purified material revealed that each peak consists of a mixture of co-migrating compounds that vary in mass by 14 Da. Measured in negative mode, the most abundant mass ions for peaks 1, 2, and 3 were 677.5 Da, 554.5 Da, and 716.6 Da, respectively.

To solve the chemical structures of the sphingolipid species, the purified compounds were subjected to high-resolution MS. As expected, the mass of peak 1 was consistent with ceramide phosphorylethanolamine (CPE) ($C_{36}H_{74}N_2O_7P$; [M−H]$^-$ m/z: calculated 677.5234, observed 677.5221), a sphingomyelin isoform previously found to be the principal *B. fragilis* sphingolipid, while the mass of peak 2 was consistent with the corresponding ceramide base ($C_{34}H_{68}NO_4$; [M−H]$^-$ m/z: calculated 554.5148, observed 554.5156) (see FIG. 1A). A set of 1D and 2D NMR experiments on the purified compounds from peaks 1 and 2 yielded resonances and couplings consistent with these assignments (see Table 2 and Table 3).

Figure 1B:
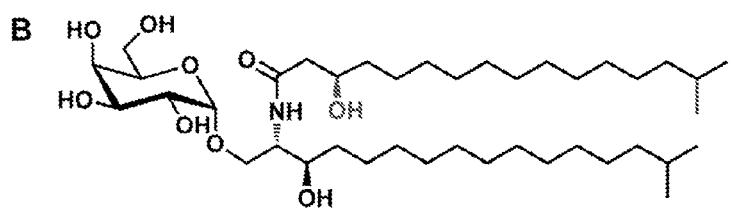
Figure 1B:
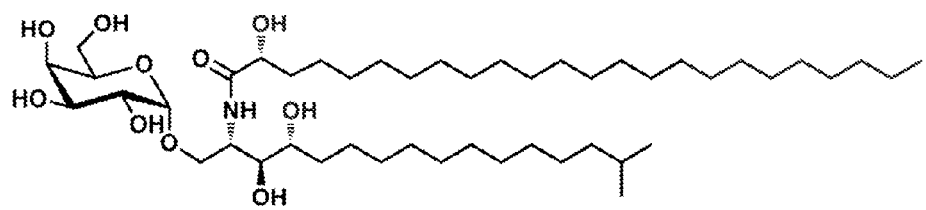
Figure 1B:
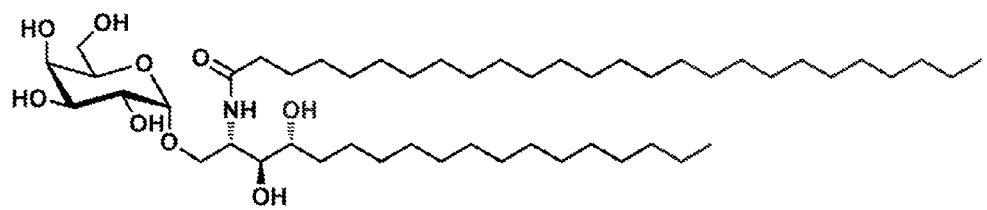

In contrast, peak 3 was not a known compound. High-resolution MS analysis of the purified material from peak 3 was consistent with an empirical formula of $C_{40}H_{79}NO_9$ ([M–H]⁻ m/z: calculated 716.5686, observed 716.5618). 2D NMR analysis indicated that this compound and CPE harbor an identical ceramide base ($C_{34}H_{68}NO_4$), suggesting that the difference ($C_6H_{11}O_5$) corresponded to a distinct head group. Three lines of evidence suggest that this head group is an α-configured galactose: (i) The molecular formula is consistent with a glycosphingolipid bearing a hexose as a head group. (ii) The ¹H NMR spectrum shows an anomeric proton with a chemical shift of 4.64, consistent with an α-linkage. (iii) Chemically synthesized α-galactosylceramide, prepared by selective α-galactosylation of the *B. fragilis* ceramide base, has a ¹H NMR spectrum indistinguishable from that of peak 3 (see Table 4). This glycosphingolipid is referred to as *B. fragilis* α-galactosylceramide (α-GalCer$_{Bf}$) (see structure in FIG. 1B).

Spectral Data

TABLE 2

NMR data and assignments for ceramide.

| position | δ ¹H (multiplicity, J, #H) | δ ¹³C |
|---|---|---|
| NH | 7.37 (d, J = 8.6 Hz, 1H) | |
| 1 | 3.74 (dd, J = 11.5, 5.3 Hz, 1H) | 61.2 |
|   | 3.66 (dd, J = 11.5, 3.7 Hz, 1H) | |
| 2 | 3.81-3.76 (m, 1H) | 54.9 |
| 3 | 3.61-3.56 (m, 1H) | 72.2 |
| 4 | 1.48-1.42 (m, 2H) | 34.1 |
| 5-13 | 1.31-1.19 (m, 18 H) | 31.3-26.0 |
| 14 | 1.14-1.08 (m, 2H) | 39.1 |
| 15 | 1.47 (d, J = 13.2 Hz, 1H) | 28.0 |
| 16 | 0.82 (d, J = 6.6 Hz, 6H) | 22.4 |
| 1' | | 173.0 |
| 2' | 2.35 (dd, J = 14.5, 3.4 Hz, 1H) | 43.5 |
|   | 2.25 (dd, J = 14.6, 8.9 Hz, 1H) | |
| 3' | 3.95-3.89 (m, 1H) | 68.7 |
| 4' | 1.47-1.40 (m, 2H) | 37.3 |
| 5'-13' | 1.31-1.19 (m, 18 H) | 31.3-26.0 |
| 14' | 1.14-1.08 (m, 2H) | 39.1 |
| 15' | 1.47 (d, J = 13.2 Hz, 1H) | 28.0 |
| 16' | 0.82 (d, J = 6.6 Hz, 6H) | 22.4 |

TABLE 3

NMR data and assignments for ceramide phosphorylethanolamine.

| position | δ ¹H (multiplicity, J, #H) | δ ¹³C |
|---|---|---|
| a | 3.09-2.99 (m, 2H) | 40.1 |
| b | 4.04-3.94 (m, 2H) | 61.5 |
| NH | | |

TABLE 3-continued

NMR data and assignments for ceramide phosphorylethanolamine.

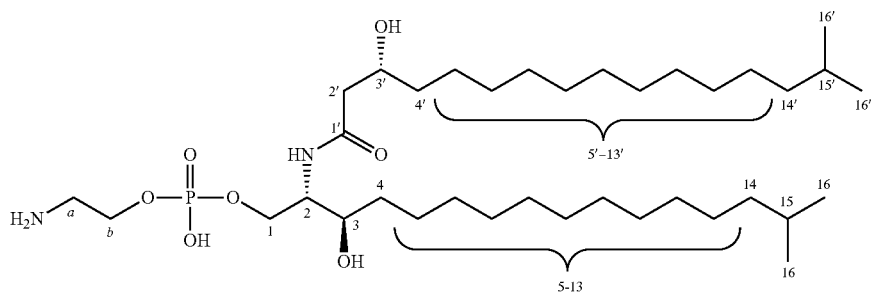

| position | δ $^1$H (multiplicity, J, #H) | δ $^{13}$C |
|---|---|---|
| 1 | 4.11-4.05 (m, 2H) | 64.3 |
|   | 3.94-3.88 (m, 1H) |  |
| 2 | 3.88-3.84 (m, 1H) | 53.9 |
| 3 | 3.56 (t, J = 7.9 Hz, 1H) | 69.7 |
| 4 | 1.38-1.36 (m, 1H) | 33.1 |
|   | 1.52-1.50 (m, 1H) |  |
| 5-13 | 1.33-1.21 (m, 18H) | 31.6-25.3 |
| 14 | 1.14-1.11 (m, 2H) | 38.8 |
| 15 | 1.49-1.47 (m, 1H) | 27.1 |
| 16 | 0.82 (d, J = 6.6 Hz, 6H) | 22.0 |
| 1' |  | 172.6 |
| 2' | 2.34 (dd, J = 14.6, 3.3 Hz, 1H) | 43.2 |
|   | 2.25 (dd, J = 14.6, 9.3 Hz, 1H) |  |
| 3' | 3.93-3.89 (m, 1H) | 68.3 |
| 4' | 1.44-1.38 (m, 2H) | 37.0 |
| 5'-13' | 1.33-1.21 (m, 18H) | 31.6-25.3 |
| 14' | 1.14-1.11 (m, 2H) | 38.8 |
| 15' | 1.49-1.47 (m, 1H) | 27.1 |
| 16' | 0.82 (d, J = 6.6 Hz, 6H) | 22.0 |

TABLE 4

NMR Data and Assignments for α-GalCer$_{Bf}$

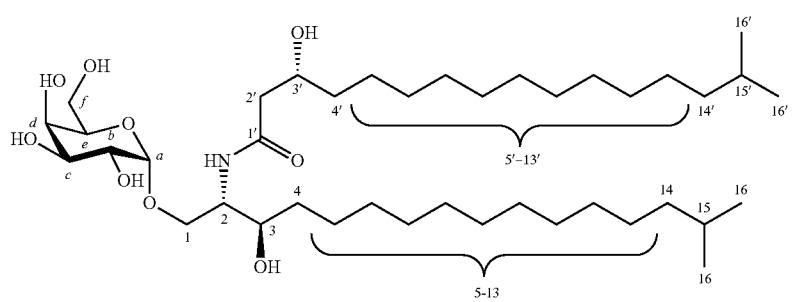

| position | δ $^1$H (multiplicity, J, #H) | δ $^{13}$C |
|---|---|---|
| a | 4.64 (d, J = 3.3 Hz, 1H) | 100.0 |
| b | 3.50 (d, J = 6.9 Hz, 1H) | 69.1 |
| b-OH | 4.15 (d, J = 7.6 Hz, 1H) |  |
| c | 3.68-3.65 (m, 1H) | 69.3 |
| c-OH | 4.33 (d, J = 4.2 Hz, 1H) |  |
| d | 3.53-3.50 (m, 1H) | 70.2 |
| d-OH | 4.47 (d, J = 5.4 Hz, 1H) |  |
| e | 3.59-3.55 (m, 1H) | 71.6 |
| f | 3.48-3.45 (m, 1H) | 61.0 |
| f | 3.42-3.37 (m, 1H) | 61.0 |
| f-OH | 4.48 (d, J = 5.4 Hz, 1H) |  |
| NH | 7.60 (d, J = 9.1 Hz, 1H) |  |
| 1 | 3.56-3.51 (m, 2H) | 67.4 |
| 2 | 3.73-3.69 (m, 1H) | 53.4 |
| 3 | 3.45-3.42 (m, 1H) | 69.6 |

TABLE 4-continued

NMR Data and Assignments for α-GalCer$_{Bf}$

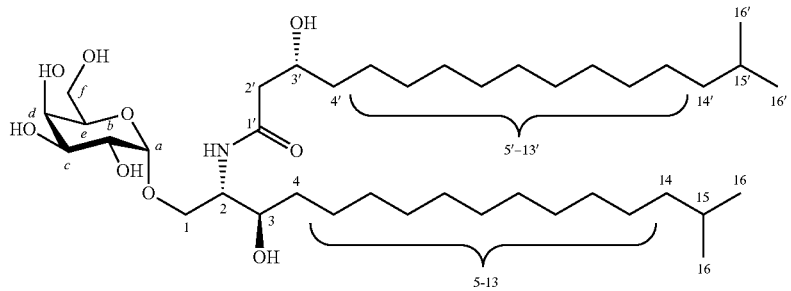

| position | δ $^1$H (multiplicity, J, #H) | δ $^{13}$C |
|---|---|---|
| 3-OH | 4.52 (d, J = 6.4 Hz, 1H) | |
| 4 | 1.47 (ddd, J = 19.9, 13.3, 6.6 Hz, 1H) 1.20-1.18 (m, 1H) | 34.2 |
| 5-13 | 1.24-1.17 (m, 18H) | 31.7-25.6 |
| 14 | 1.14-1.06 (m, 2 H) | 38.9 |
| 15 | 1.47 (td, J = 13.3, 6.6 Hz, 1H) | 27.9 |
| 16 | 0.82 (d, J = 6.6 Hz, 6H) | 22.9 |
| 1' | | 170.8 |
| 2' | 2.17 (ddd, J = 26.3, 13.8, 6.6 Hz, 2H) | 44.5 |
| 3' | 3.79-3.73 (m, 1H) | 67.9 |
| 3'-OH | 4.58 (d, J = 4.9 Hz, 1H) | |
| 4' | 1.33-1.31 (m, 1H) | 37.0 |
| | 1.27-1.25 (m, 1H) | |
| 5'-13' | 1.24-1.17 (m, 18H) | 31.7-25.6 |
| 14' | 1.14-1.06 (m, 2 H) | 38.9 |
| 15' | 1.47 (td, J = 13.3, 6.6 Hz, 1H) | 27.9 |
| 16' | 0.82 (d, J = 6.6 Hz, 6H) | 22.9 |

Results of infrared (IR), NMR, optical rotation (OR), and high resolution mass spectormetry (HRMS) analyses for each of ceramide, α-GalCer$_{Bf}$, and CPE follow.

Ceramide: IR (neat): 3296.1 (br, s), 2917.8 (s), 2849.3 (s), 1639.3 (m), 1547.6 (m), 1467.1 (m), 1420.1 (w), 1383.0 (w), 1365.7 (w), 1249.8 (w), 1108.9 (w), 1021.9 (w). $^1$H NMR (600 MHz, 2:1 CDCl$_3$:CD$_3$OD): δ 7.37 (d, J=8.6 Hz, 1H), 3.94-3.89 (m, 1H), 3.81-3.76 (m, 1H), 3.73 (dd, J=11.5, 5.3 Hz, 1H), 3.66 (dd, J=11.5, 3.7 Hz, 1H), 3.63-3.55 (m, 1H), 2.35 (dd, J=14.5, 3.3 Hz, 1H), 2.25 (dd, J=14.6, 8.9 Hz, 1H), 1.52-1.34 (m, 6H), 1.31-1.18 (m, 36H), 1.14-1.02 (m, 4H), 0.84-0.77 (m, 12H). $^{13}$C NMR (100 MHz, 2:1 CDCl$_3$:CD$_3$OD): δ 173.04, 72.23, 68.57, 61.22, 54.68, 43.34, 38.95, 37.05, 36.52, 34.30, 33.88, 31.80, 29.90, 29.81, 29.59, 29.56, 29.55, 29.52, 29.51, 29.48, 29.36, 29.23, 27.84, 27.29, 26.98, 25.79, 25.40, 22.53, 22.36, 18.94, 13.78, 11.09. Optical rotation: $[α]_D^{22}$ −1.73 (c=0.86, 2:1 CHCl$_3$:MeOH). HRMS m/z calculated for C$_{32}$H$_{64}$NO$_4$ (M-H): 526.4835. Found: 526.4791 (M-H)$^-$. HRMS m/z calcd for C$_{33}$H$_{66}$NO$_4$ (M-H): 540.4992. Found: 540.4947 (M-H)$^-$. HRMS m/z calculated for C$_{34}$H$_{68}$NO$_4$ (M-H): 554.5148. Found: 554.5156 (M-H)$^-$. HRMS m/z calculated for C$_{35}$H$_{70}$NO$_4$ (M-H): 568.5305. Found: 568.5256 (M-H)$^-$. HRMS m/z calculated for C$_{36}$H$_{72}$NO$_4$ (—H): 582.5461. Found: 582.5398 (M-H)$^-$.

α-GalCer$_{Bf}$: IR (neat): 3278.6 (br, s), 2919.4 (s), 2850.5 (s), 1643.8 (m), 1620.8 (m), 1563.1 (m), 1465.5 (m), 1365.4 (w), 1342.3 (w), 1024.8 (s). $^1$H NMR (600 MHz, DMSO): δ 7.60 (d, J=9.1 Hz, 1H), 4.64 (d, J=3.3 Hz, 1H), 4.58 (d, J=4.9 Hz, 1H), 4.52 (d, J=6.4 Hz, 1H), 4.49 (d, J=5.6 Hz, 1H), 4.47 (d, J=5.6 Hz, 1H), 4.33 (d, J=4.2 Hz, 1H), 4.15 (d, J=7.6 Hz, 1H), 3.80-3.74 (m, 1H), 3.74-3.69 (m, 1H), 3.69-3.64 (m, 1H), 3.60-3.36 (m, 7H), 2.17 (ddd, J=26.3, 13.8, 6.6 Hz, 2H), 1.52-1.43 (m, 3H), 1.43-1.26 (m, 2H), 1.21 (br s, 37H), 1.14-1.06 (m, 4H), 0.82 (d, J=6.6 Hz, 12H). $^{13}$C NMR (100 MHz, DMSO): δ 170.79, 99.95, 71.64, 70.15, 69.61, 69.32, 69.13, 67.90, 67.36, 61.02, 53.39, 44.47, 38.92, 36.99, 34.19, 34.07, 31.74, 27.85, 27.24, 26.91, 25.56, 22.91. Optical rotation: $[α]_D^{22}$ +60.47 (c=0.13, 2:1 CHCl$_3$:MeOH). HRMS m/z calculated for C$_{39}$H$_{76}$NO$_9$ (M-H): 702.5520. Found: 702.5463 (M-H)$^-$. HRMS m/z calculated for C$_{40}$H$_{78}$NO$_9$ (M-H): 716.5677. Found: 716.5686 (M-H)$^-$. HRMS m/z calculated for C$_{41}$H$_{80}$NO$_9$ (M-H): 730.5833. Found: 730.5772 (M-H)$^-$. HRMS m/z calculated for C$_{42}$H$_{82}$NO$_9$ (M-H): 744.5990. Found: 744.5931 (M-H)$^-$.

CPE: IR (neat): 3322.0 (br, s), 2918.3 (s), 2849.6 (s), 1649.9 (s), 1559.3 (s), 1466.2 (m), 1466.2 (m), 1410.0 (m), 1221.8 (s), 1080.4 (s), 1021.1 (s). $^1$H NMR (600 MHz, 2:1 CDCl$_3$:CD$_3$OD): δ 4.11-4.05 (m, 1H), 4.04-3.94 (m, 2H), 3.94-3.83 (m, 3H), 3.56 (t, J=7.9 Hz, 1H), 3.09-2.99 (m, 2H), 2.34 (dd, J=14.6, 3.3 Hz, 1H), 2.25 (dd, J=14.6, 9.3 Hz, 1H), 1.54-1.31 (m, 6H), 1.22 (s, 36H), 1.15-1.11 (m, 4H), 0.82 (d, J=6.6 Hz, 12H). $^{13}$C NMR (100 MHz, 2:1 CDCl$_3$:CD$_3$OD) δ 172.65, 69.69, 68.33, 64.26, 61.46, 53.95, 53.89, 43.28, 40.23, 40.16, 38.76, 37.01, 33.31, 31.61, 29.61, 29.38, 29.15, 29.03, 27.64, 27.09, 25.53, 25.28, 22.04. Optical rotation: $[α]_D^{22}$ +13.30 (c=0.28, 2:1 CHCl$_3$:MeOH). HRMS m/z calculated for C$_{35}$H$_{72}$N$_2$O$_7$P (M-H): 663.5077. Found: 663.5025 (M-H)$^-$. HRMS m/z calculated for C$_{36}$H$_{74}$N$_2$O$_7$P (M-H): 677.5234. Found: 677.5221 (M-H)$^-$. HRMS m/z calculated for C$_{37}$H$_{76}$N$_2$O$_7$P (M-H): 691.5390. Found: 691.5334 (M-H)$^-$. HRMS m/z calculated for C$_{38}$H$_{78}$N$_2$O$_7$P (M-H): 705.5547. Found: 705.5494 (M-H)$^-$.

Example 3

Synthesis and characterization of *B. fragilis* α-GalCer$_{Bf}$

This example describes semi-synthetic generation of α-GalCer$_{Bf}$ and analysis of the sphingolipid. A synthesis procedure is illustrated in the following schematic.

Semi-Synthetic Generation of α-GalCer$_{Bf}$.

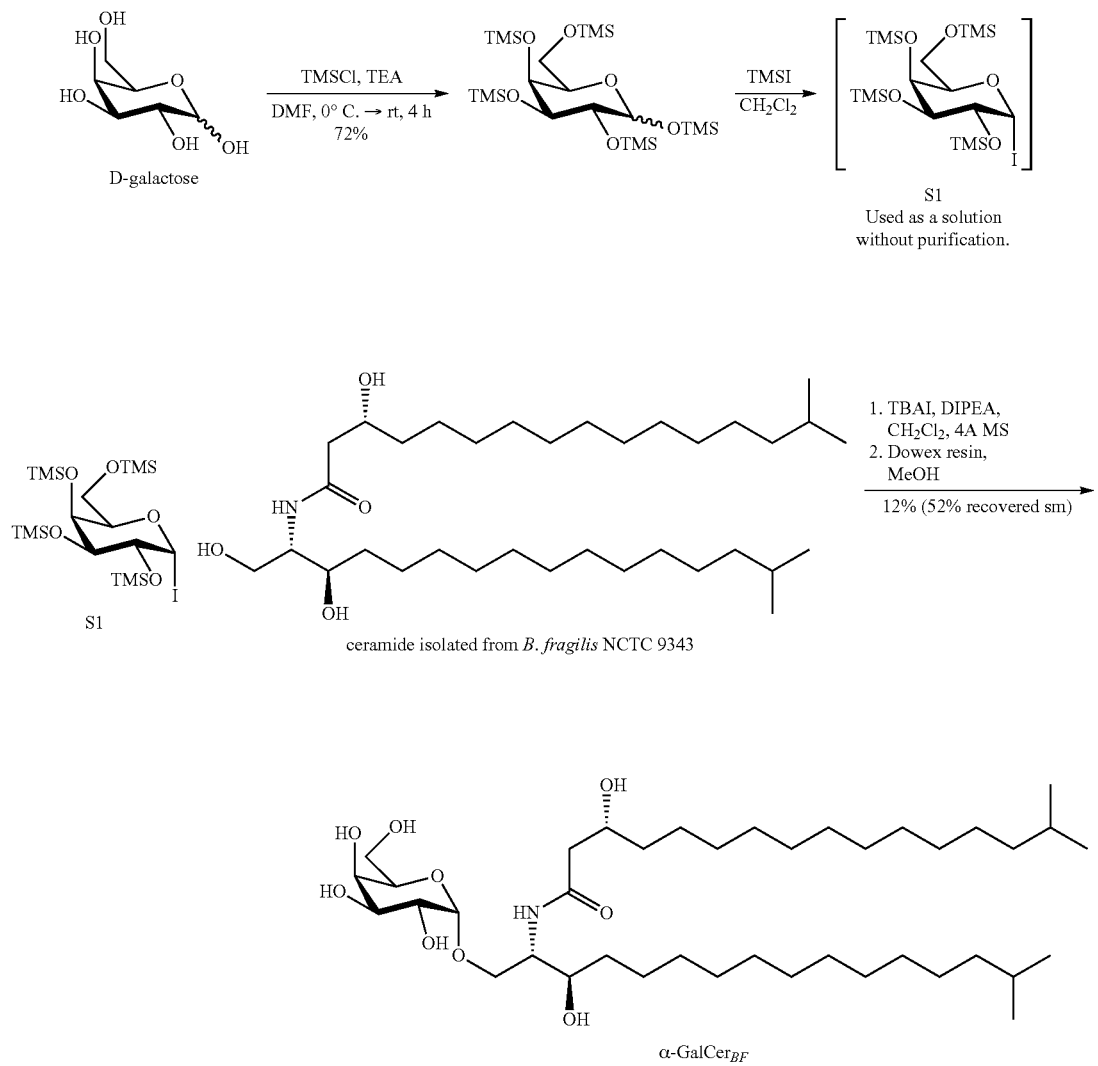

TMS-protected galactose (see, e.g., Bhat et al., *Org. Lett.* 3:2081-84 (2001) and α-iodo-substituted compound S1 (see, e.g., Schombs et al., *J. Org. Chem.* 75:4891-4898 (2010)) were prepared as previously described. Ceramide (5.0 mg, 0.0088 mmol) was isolated from *B. fragilis* NCTC 9343 as described in Example 2. α-Selective glycosylation was carried out as previously described, and α-GalCer$_{Bf}$ was obtained after purification by preparative TLC (see Example 2) in 12% yield (0.74 mg, 0.0010 mmol). Unreacted ceramide was recovered at 52% after purification (2.6 mg, 0.0046 mmol). $^1$H NMR analysis (600 MHz, DMSO) of semisynthetic α-GalCer$_{Bf}$ indicated that it was identical to α-GalCer$_{Bf}$ isolated from *B. fragilis* NCTC 9343.

$^1$H NMR (600 MHz, DMSO) δ 7.60 (d, J=9.4 Hz, 1H), 4.64 (d, J=3.2 Hz, 1H), 4.57 (d, J=4.9 Hz, 1H), 4.52 (d, J=6.5 Hz, 1H), 4.49 (d, J=5.6 Hz, 1H), 4.47 (d, J=5.6 Hz, 1H), 4.32 (d, J=4.4 Hz, 1H), 4.14 (d, J=8.2 Hz, 1H), 3.78-3.74 (m, 1H), 3.74-3.69 (m, 1H), 3.68-3.64 (m, 1H), 3.61-3.36 (m, 7H), 2.17 (ddd, J=20.4, 13.7, 6.9 Hz, 2H), 1.51-1.43 (m, 3H), 1.42-1.26 (m, 2H), 1.21 (s, 37H), 1.13-1.09 (m, 4H), 0.82 (d, J=6.6 Hz, 12H).

Ceramide isolated from *B. fragilis* NCTC 9343 was methanolyzed according to the procedure described in Miyagawa et al. (*J. Biochem.* 86:311-20 (1979)). A schematic of the procedure and a description of the process are provided as follows.

S1.11. Methanolysis of Ceramide and Determination of Absolute Configuration.

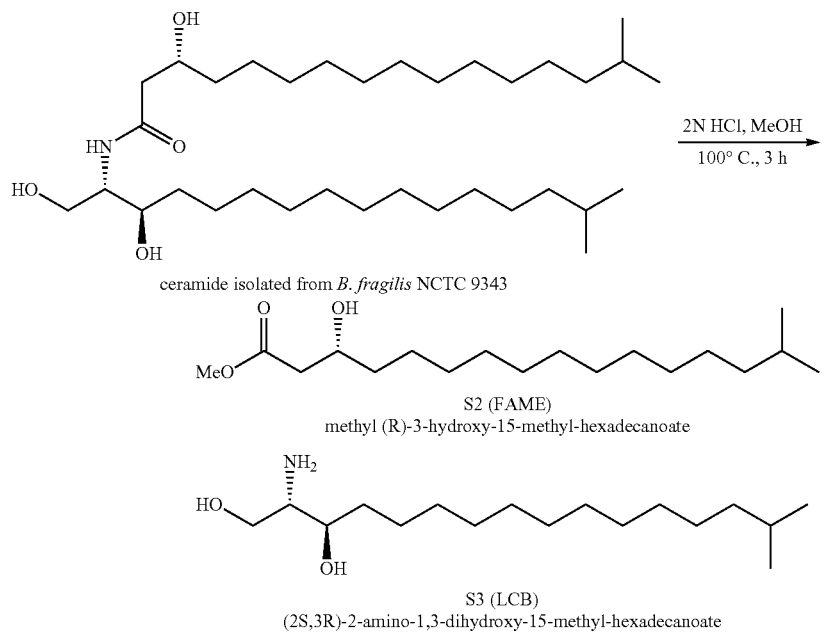

ceramide isolated from *B. fragilis* NCTC 9343

S2 (FAME)
methyl (R)-3-hydroxy-15-methyl-hexadecanoate

S3 (LCB)
(2S,3R)-2-amino-1,3-dihydroxy-15-methyl-hexadecanoate

Ceramide isolated from *B. fragilis* NCTC 9343 (10 mg, 0.018 mmol) was suspended in a solution of HCl in methanol (2 mL, 2N) in a sealed tube. The mixture was kept at 100° C. for 3 h, then allowed to cool to room temperature. Water (1 mL) was added, after which the aqueous layer was washed with hexanes (3×3 mL). The aqueous layer was set aside. The organic layers were combined, dried over $Na_2SO_4$, and the volatiles were removed in vacuo. The resulting residue, which contained fatty acids methyl ester (FAME) S2, was purified by silica gel chromatography (10:1 hexanes:EtOAc) to furnish pure S2 (2.8 mg, 0.0092 mmol, 51%). The aqueous layer was treated with concentrated KOH until a pH of 10-12 was reached, then washed with $Et_2O$ (2×2 mL). The organic layers were combined, dried over $Na_2SO_4$, and the volatiles were removed in vacuo. The resulting residue, which contained long chain base (LCB) S3, was purified by preparative TLC (silica gel, 100:20:12:5 $CHCl_3$:MeOH:AcOH:$H_2O$, $R_f$=0.37) to furnish pure S3 (1.1 mg, 0.0038 mmol, 21%).

S2 (FAME): IR (neat): 2922.17 (s), 2852.1 (s), 1725.3 (s), 1463.6 (w), 1436.8 (m), 1365.1 (w), 1168.5 (m), 1051.9 (m). $^1$H NMR (600 MHz, cdcl$_3$) δ 4.00 (dtd, J=12.2, 4.4, 3.1 Hz, 1H), 3.71 (s, 3H), 2.51 (dd, J=16.4, 3.0 Hz, 1H), 2.41 (dd, J=16.4, 9.1 Hz, 1H), 1.60-1.48 (m, 2H), 1.47-1.38 (m, 2H), 1.38-1.19 (m, 18H), 1.15 (dd, J=14.1, 6.7 Hz, 2H), 0.86 (d, J=6.6 Hz, 6H). HRMS Calcd for $C_{18}H_{37}O_3$ [M+H]: 301.273721. Found [M+H]: 301.27323. Optical rotation: $[\alpha]_D^{25}$–14.8 (c=0.183, $CHCl_3$). The absolute configuration was assigned based on comparison with a reported value. Reported values for the optical rotation of methyl (R)-3-hydroxy-15-methyl-hexadecanoate: (a) $[\alpha]_D^{25}$–14.3 (c=0.51, $CHCl_3$):Labeeuw et al., *Tetrahedron: Asymmetry*, 15:1899-1908 (2004)); (b) $[\alpha]_D^{25}$–12.7 (c=0.518, $CHCl_3$): Kamiyama et al., *J. Antibiot.* 48:929-936 (1995).

S3 (LCB): IR (neat): 3373.2 (br, s), 2921.2 (s), 2851.7 (s), 1631.9 (m), 1588.7 (m), 1548.7 (w), 1510.0 (w), 1464.9 (w), 1367.5 (m), 1144.9 (w), 1050.8 (w). $^1$H NMR (600 MHz, pyridine) δ 4.29 (dd, J=10.4, 4.4 Hz, 1H), 4.11 (dd, J=10.4, 7.3 Hz, 1H), 4.06-3.99 (m, 1H), 3.36-3.26 (m, 1H), 1.92- 1.77 (m, 3H), 1.65-1.52 (m, 1H), 1.53-1.34 (m, 4H), 1.27 (s, 17H), 1.18-1.10 (m, 2H), 0.87 (d, J=6.6 Hz, 6H). HRMS Calcd for $C_{17}H_{38}NO_2$ [M+H]: 288.289706. Found [M+H]: 288.28930. Optical rotation: $[\alpha]_D^{22}$+6.0 (c=0.0050, pyr-d$_5$). The absolute configuration was assigned based on comparison with reported values (see, e.g., So et al., *J. Org. Chem.* 69:3233-35 (2004)).

TABLE 5

High Resolution Mass Spectrometry (HRMS) and LC-MS Analysis

| Compound | source | calculated [M-H] | observed [M-H] | MS data source[a] | ppm difference |
|---|---|---|---|---|---|
| α-GalCer$_{Bf}$ | *B. fragilis* NCTC 9343 | 702.55201 | 702.5463 | LC-MS | 8.1 |
| | | 716.56766 | 716.5624 | LC-MS | 7.3 |
| | | 730.58331 | 730.5777 | LC-MS | 7.7 |
| | | 744.59896 | 744.5933 | LC-MS | 7.6 |
| α-GalCer$_{Bf}$ | *B. fragilis* NCTC 9343 | 716.56766 | 716.56860 | HRMS | -1.3 |
| | | 730.58331 | 730.58393 | HRMS | -0.9 |
| α-GalCer$_{Bf}$ | OMV from *B. fragilis* NCTC 9343 | 716.56766 | 716.57000 | HRMS | -3.3 |
| | | 730.58331 | 730.58457 | HRMS | -1.7 |
| | | 744.59896 | 744.60133 | HRMS | -3.2 |
| α-GalCer$_{Bf}$ | *B. fragilis* 63812 | 744.59896 | 744.60120 | HRMS | -3.0 |
| ceramide | *B. fragilis* NCTC 9343 | 526.48353 | 526.4794 | LC-MS | 7.9 |
| | | 540.49918 | 540.4944 | LC-MS | 8.8 |
| | | 554.51483 | 554.5089 | LC-MS | 10.6 |
| | | 568.53048 | 568.5222 | LC-MS | 14.5 |
| | | 582.54613 | 582.5393 | LC-MS | 11.7 |
| | | 596.56178 | 596.5530 | LC-MS | 14.7 |
| ceramide | *B. fragilis* NCTC 9343 | 554.51483 | 554.51560 | HRMS | -1.4 |
| | | 568.53048 | 568.53117 | HRMS | -1.2 |
| CPE | *B. fragilis* NCTC 9343 | 635.47641 | 635.4732 | LC-MS | 5.1 |
| | | 649.49206 | 649.4888 | LC-MS | 5.0 |
| | | 663.50771 | 663.5034 | LC-MS | 6.5 |
| | | 677.52336 | 677.5186 | LC-MS | 7.1 |

TABLE 5-continued

High Resolution Mass Spectrometry (HRMS) and LC-MS Analysis

| Compound | source | calculated [M-H] | observed [M-H] | MS data source[a] | ppm difference |
|---|---|---|---|---|---|
| | | 691.53901 | 691.5343 | LC-MS | 6.9 |
| | | 705.55466 | 705.5501 | LC-MS | 6.4 |
| CPE | B. fragilis NCTC 9343 | 677.52336 | 677.5221 | HRMS | 1.9 |
| | | 691.53901 | 691.5386 | HRMS | 0.59 |
| | | 705.55466 | 705.55373 | HRMS | 1.3 |
| CPE | OMV from B. fragilis NCTC 9343 | 691.53901 | 691.5418 | HRMS | −4.0 |

TABLE 6

Summary of High Resolution LC-MS data analyzed by XCMS

| compound | exact mass [M-H] | retention time (min) | fold change[a] (ΔBF2461[e]) |
|---|---|---|---|
| ceramide | 649.4874 | 16.92 | ND |
| phosphorylethanolamine (CPE) | 663.5025 | 18.67 | 3474 |
| | 677.5204 | 19.54 | 3801 |
| | 691.5341 | 20.36 | 4390 |
| | 705.5493 | 21.09 | 1338 |
| α-GalCer$_{BF}$ | 702.5472 | 26.04 | 259 |
| | 716.5623 | 26.66 | 898 |
| | 730.5780 | 27.50 | 511 |
| | 744.5930 | 28.13 | 604 |
| ceramide | 526.4795 | 25.70 | 367 |
| | 540.4954 | 26.67 | 334 |
| | 554.5142 | 27.27 | 46 |
| | 568.5291 | 28.08 | 72 |
| | 582.5452 | 28.71 | 55 |
| | 596.5549 | 29.36 | 10 |
| phosphatidylethanolamine[b] | 620.4243 | 17.42 | 16 |
| | 634.4405 | 18.00 | 8 |
| | 648.4554 | 19.66 | 3 |
| | 662.4712 | 20.33 | 7 |
| | 676.4867 | 21.45 | 4 |
| | 690.5021 | 22.13 | 1 |

[a]Determined by XCMS (see, e.g., Smith et al., Anal. Chem. 78:779-87 (2006)).
[b]Phosphatidylethanolamine was analyzed as a control.
[e]Sphingolipid-deficient mutant
[f]Strain carries knockout of a gene in an unrelated pathway - used as a control.

Example 4

Binding of B. fragilis α-GalCer$_{Bf}$ to CD1d

This example describes that α-GalCer$_{Bf}$ is a ligand of CD1d present on NKT cells.

The reagents used in Examples 4 and 5 for the immunology studies were as follows. PBS-57 loaded mCD1d tetramers, which were used for mouse experiments, and unloaded mCD1d monomers were obtained from the NIH Tetramer Core Facility. For loading, monomers were incubated with KRN7000 or α-GalCer$_{Bf}$ diluted in DMSO at 6 fold molar excess at 37° C. for 3 hrs in the presence of pepstatin, leupeptin, EDTA and TWEEN 20. Samples were concentrated using a 30K microconcentrator. Monomers were tetramerized by incubation with streptavidin-conjugated allophycocyanin (APC) (Molecular Probes, Inc., Eugene, Oreg.) at a 1:1 ratio. Staining was performed at room temperature for 1 hr. The antibodies (shown in parentheses) for each of CD4 (RM4-5), CD3 (2C11), CD69 (H1.2F3), CD25 (PC61), NK1.1 (PK136), CD86 (GL1), MHCII (NIMR-4), and IFNγ (XMG1.2) were purchased (BioLegend (San Diego, Calif.), eBiosciences (San Diego, Calif.), Southern Biotechnology Associates (SBA) (Birmingham, Ala.), or Pharmingen (San Diego, Calif.)). For cell surface staining, cells were preincubated with rat hybridoma 2.4G2 culture supernatant (UCSF cell culture facility) (commercially available from various manufacturers), and incubated with antibodies/tetramer for 30 minutes at 4° C. The 2.4G2 antibody is a rat (IgG2b isotype) anti-mouse CD16/CD32 (CD16-2/Fcγ RIIb) antibody. Viability was determined by staining cells with LIVE/DEAD fixable Aqua stain (Invitrogen Life Technologies, Carlsbad, Calif.) per manufacturer's instructions. 200 μg anti-CD1d antibody (1B1 clone, eBiosciences) was administered i.v. 5-30 minutes prior to BMDC transfer. A rat IgG2b antibody (LTF-2, UCSF cell culture facility; commercially available from various manufacturers) was used as isotype control. KRN7000 was purchased from Avanti Polar Lipids (Alabaster, Ala.).

A synthetic derivative of the sponge-derived α-galactosylceramide agelasphin-9b (see FIG. 1B) (see, e.g., Akimoto et al., Tetrahedron Lett. 34:5593-96 (1993)), called KRN7000 (see FIG. 1B), is an agonist of invariant natural killer T cells (NKT) cells. NKT cells express a semi-invariant T cell receptor (TCR) that recognizes glycolipids presented by CD1d (see, e.g., Bendelac et al., Annu. Rev. Immunol. 25:297-336 (2007)). Although KRN7000 is a nonphysiological antigen, it has become an often used reagent for studying NKT cell biology. NKT cells are often identified or isolated by flow cytometry on the basis of their ability to bind a synthetic tetramer of CD loaded with a derivative of KRN7000.

Synthetic CD1d tetramers were loaded with each sphingolipid, KRN7000 and α-GalCer$_{Bf}$), and the capability of the sphingolipid/CD1d-tetramer complex (hereafter called 'tetramer') to stain three NKT-cell-derived hybridomas was determined (see, e.g., Brossay et al., J. Immunol. 161:5124-28 (1998); Burdin et al., J. Immunol. 161:3271-81 (1998)).

Figure 4A:
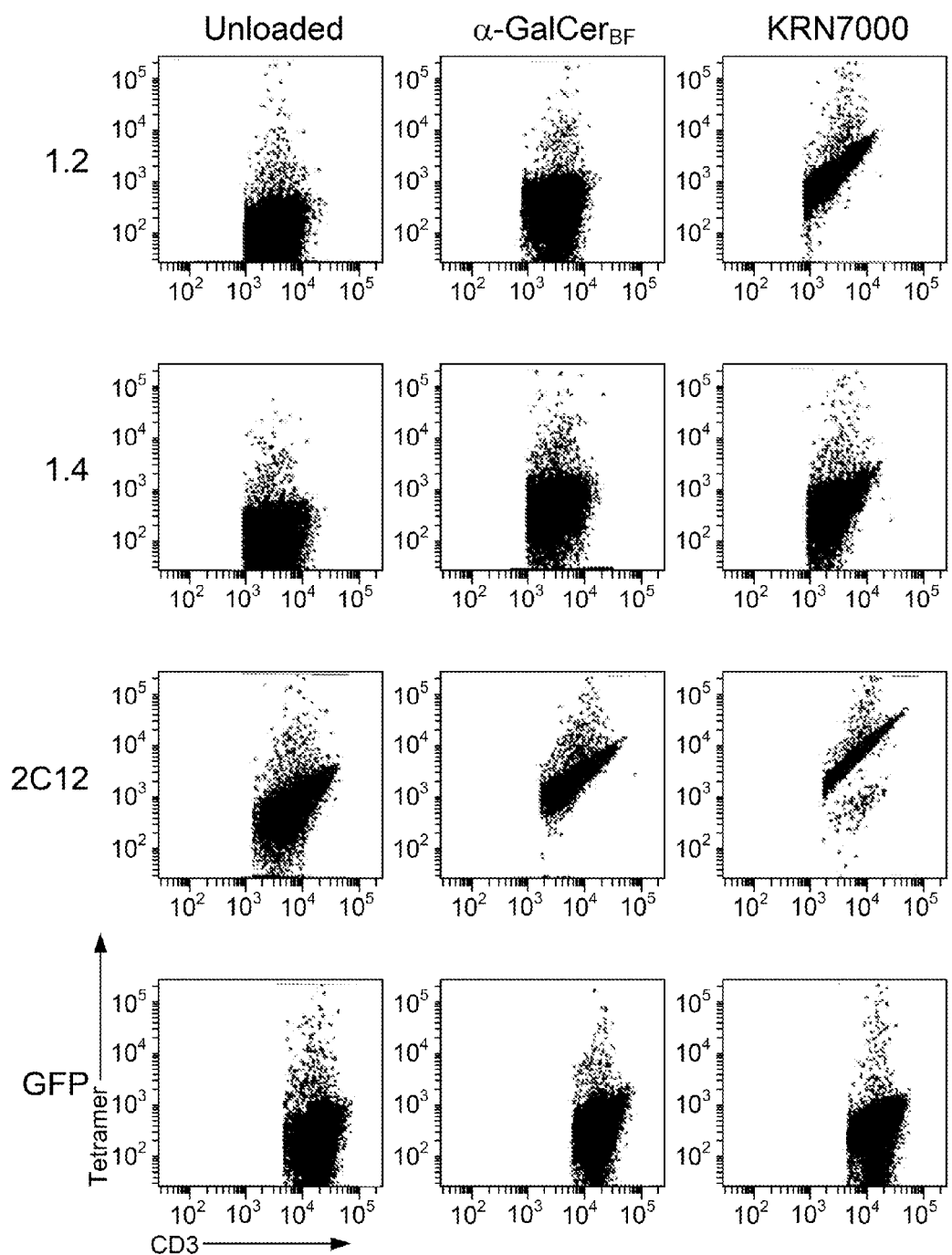
FIGS. 4A-4C illustrate that α-GalCer$_{Bf}$ binds CD1d and activates murine NKT cells in vitro.

The intensity of tetramer staining is known to correlate with the affinity of the TCR for the ligand/CD1d complex (see, e.g., Sidobre et al., J. Immunol. 169:1340-48 (2002)). Mouse CD1d (mCD1d) tetramer loaded with KRN7000 bound the three hybridomas with varying affinity, as previously described (see Sidobre et al., supra) (MFI (Median Fluorescence Intensity): 8932 for N38-2C12 (2C12) compared to 2151 for DN3A4-1.2 (1.2) and 683 for DN3A4-1.4 (1.4)) (see FIG. 4A). The mCD1d tetramer loaded with α-GalCer$_{Bf}$ also bound each hybridoma, with strongest binding to the 2C12 hybridoma (MFI: 2871 compared to 460 for 1.2 and 626 for 1.4) (see FIG. 4A). These data suggest that the TCR expressed by the 2C12 hybridoma has the highest affinity/avidity for the α-GalCer$_{Bf}$/CD1d complex, which is similar to its affinity/avidity for the KRN7000/CD1d complex. Empty CD tetramers did not stain any of the hybridomas (MFI: 836 for 2C12, 114 for 1.2, and 151 for 1.4) and neither tetramer stained a CD4 +MHCII restricted hybridoma reactive to green fluorescent protein (GFP) (GFP-36) (Dr. Bluestone and Dr. Yadav, University of California at San Francisco), indicating that the tetramer staining was ligand- and TCR-specific (see FIG. 4A).

Example 5

Activation of NKT Cell Hybridomas by B. fragilis α-GalCer$_{Bf}$

This example describes the capability of α-GalCer$_{Bf}$ to stimulate cytokine release by NKT hybridoma cells.

Experiments were then performed to determine whether binding of the α-GalCer$_{Bf}$/CD1d complex to the semi-invariant TCR expressed by NKT cell hybridomas stimulates cytokine release from NKT cells in vitro. NKT cell hybridomas were incubated with bone marrow-derived dendritic cells (BMDCs) as antigen presenting cells (APCs) in the presence of increasing amounts of KRN7000 or α-GalCer$_{Bf}$.

Bone marrow progenitors were cultured in IMDM containing 10% FBS with addition of 20 ng/ml GM-CSF (G6 supernatant, a gift from Dr. Abul K. Abbas, University of California at San Francisco, San Francisco, Calif.) starting on day 2 and 1 ng/ml IL-4 (13L$_6$ supernatant, a gift from Dr. Abul K. Abbas) on day 6. For in vivo transfers and in vitro CD1d blocking experiments, BMDCs were pulsed with 1 ng/mL LPS (*Escherichia coli* 026:B6; Sigma-Aldrich)+/−10 μg/mL α-GalCer$_{Bf}$ on day 8. After overnight culture, cells were harvested and washed twice before use.

Figure 5:
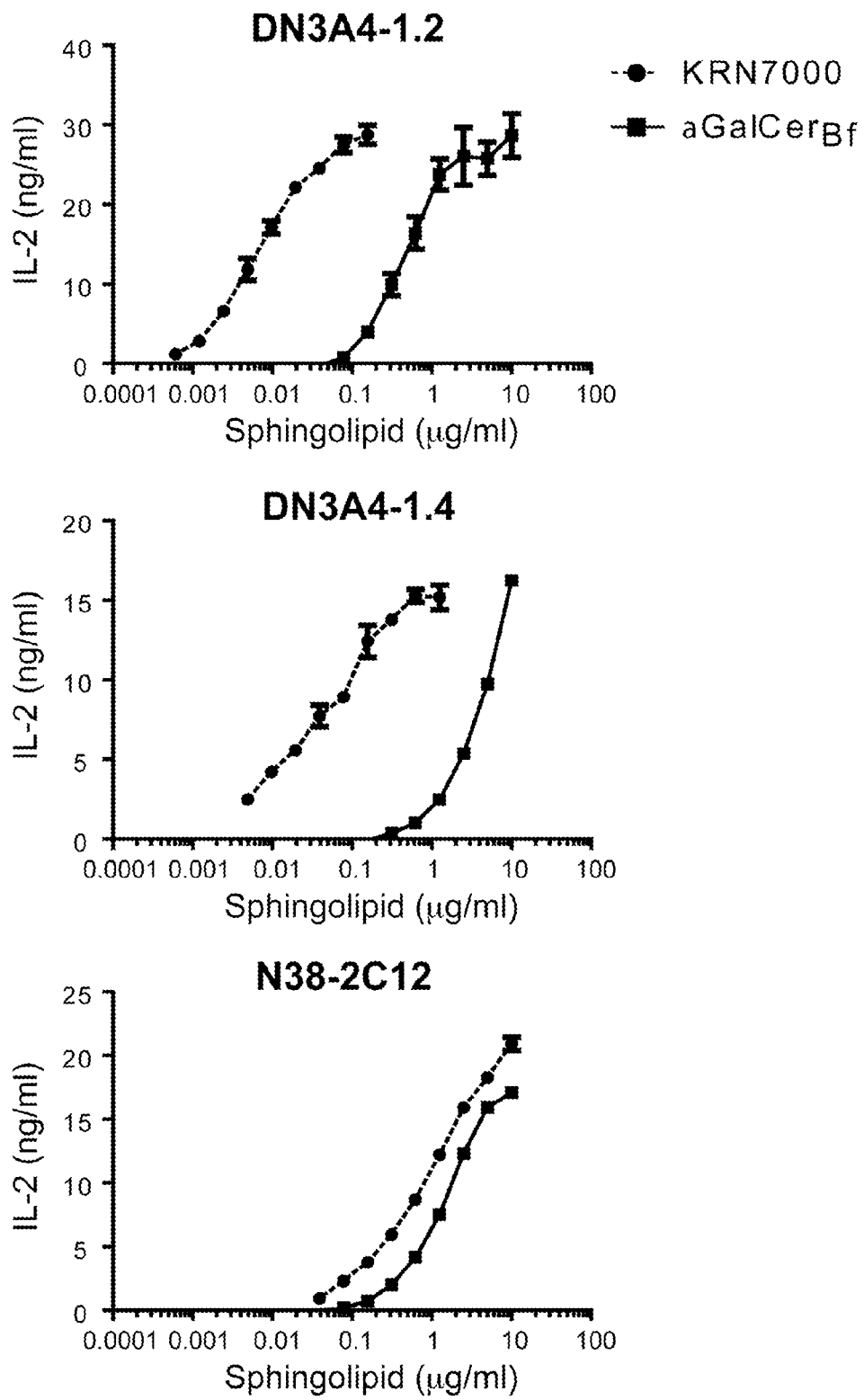
FIG. 5 shows IL-2 production in NKT hybridoma cells exposed to each of KRN7000 and α-GalCer$_{Bf}$. BMDCs and NKT hybridomas were cultured at a 3:1 hybridoma:BMDC ratio and the indicated doses of KRN7000 or α-GalCer$_{Bf}$ in the presence of 1 µg/ml LPS. Supernatants were harvested after 24 hrs, and IL-2 production was measured by ELISA.

NKT hybridomas were stimulated in dose titration experiments. BMDCs and DN3A4-1.2, DN3A4-1.4 and N38-2C12 NKT hybridomas (gift from Dr. Mitchell Kronenberg, La Jolla Institute for Allergy and Immunology, La Jolla, Calif.) and GFP36 CD4 hybridoma were cultured at a 3:1 hybridoma:BMDC ratio with the indicated doses of KRN7000 or α-GalCer$_{Bf}$ as shown in FIG. 5 in the presence of 1 μg/ml LPS. Supernatants were harvested after 24 hr, and IL-2 production was measured by ELISA. For in vitro CD1d blocking experiments, α-GalCer$_{Bf}$ pulsed BMDCs were cultured at a 3:1 hybridoma:BMDC ratio in the presence of 10 μg/mL anti-CD1d antibody. Supernatants were harvested after 16-18 hr and IL-2 production was measured by ELISA.

Figure 4B:
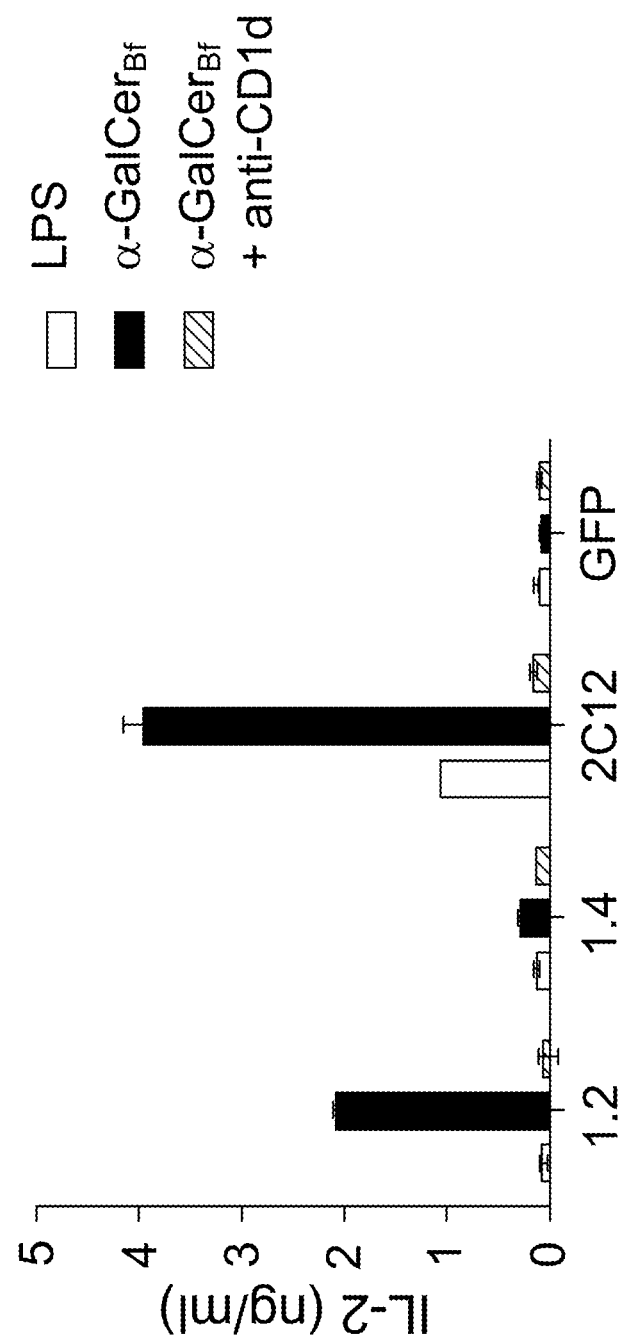

The three NKT cell hybridomas tested produced IL-2 in response to both sphingolipids in a dose-dependent manner, suggesting that α-GalCer$_{Bf}$ is a stimulatory ligand for NKT cells in vitro (see FIG. 4B and FIG. 5). The 2C12 hybridoma showed a similar response to both sphingolipids, while hybridomas 1.2 and 1.4 were 30-fold and 80-fold more sensitive to KRN7000, respectively. The increased sensitivity of hybridomas 1.2 and 1.4 to KRN7000 is not surprising because KRN7000 has been reported to serve as an unusually potent agonist of NKT cells (see, e.g., Sidobre, supra). IL-2 production appeared dependent on CD1d:TCR-dependent activation as illustrated in that the response to α-GalCer$_{Bf}$ was completely inhibited by anti-CD1d antibodies (see FIG. 4B). α-GalCer$_{Bf}$ did not stimulate IL-2 production by a CD4' MHCII restricted hybridoma reactive to GFP (see FIG. 4B).

The statistical significance of differences between groups was determined by the Mann-Whitney test using Prism software.

Example 6

In Vitro Stimulation of Murine NKT Cells by *B. fragilis* α-GalCer$_{Bf}$

This example describes the capability of α-GalCer$_{Bf}$ to stimulate isolated murine NKT cells.

Figure 4C:
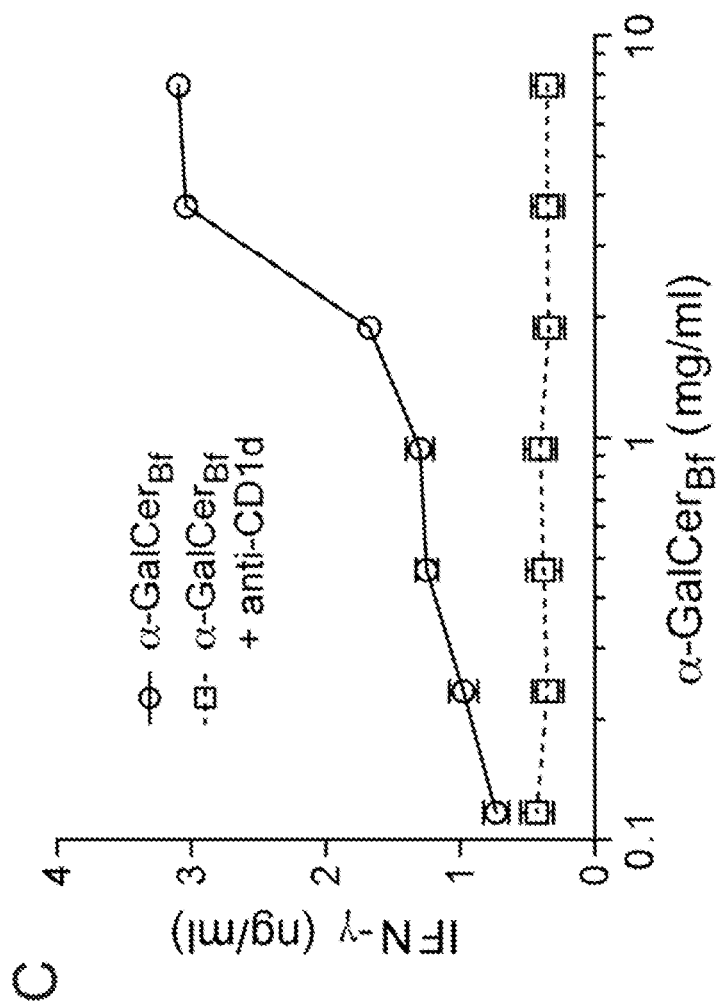

The capability of α-GalCer$_{Bf}$ to stimulate freshly isolated NKT cells was determined. Mouse liver mononuclear cells, 30-50% of which are NKT cells, were incubated with splenocytes as APCs in the presence of increasing doses of α-GalCer$_{Bf}$ and examined for IFN-γ production. As shown in FIG. 4C, α-GalCer$_{Bf}$ induced IFN-γ in a dose-dependent manner, demonstrating that α-GalCer$_{Bf}$ can stimulate cytokine production by authentic NKT cells. This response was inhibited by anti-CD1d antibodies (see FIG. 4C), consistent with the previous result that NKT cell stimulation is dependent on ligand presentation by CD1d (see FIG. 4B).

Example 7

Stimulation of Human NKT Cells by *B. fragilis* α-GalCer$_{Bf}$

This example describes the capability of α-GalCer$_{Bf}$ to stimulate isolated human NKT cells.

The capability of α-GalCer$_{Bf}$ to stimulate freshly isolated NKT cells was determined. A first experiment was performed to determine whether Vα24$^+$ cells could be expanded in vitro with α-GalCer$_{Bf}$ as previously described for KRN7000 (see, e.g., Rogers et al., *J. Immunol. Meth.* 285:197-214 (2004)). Peripheral blood mononuclear cells (PBMCs) were cultured with 0.1 μg/ml KRN7000, 1 μg/ml α-GalCer$_{Bf}$, or 1 μg/ml ceramide$_{Bf}$ for 13 days. The presence of CD3 Vα24$^+$ cells was then assessed by flow cytometry. At least two individual experiments performed with six individual donors. Human NKT cells were purified after two rounds of expansion with 1 μg/ml α-GalCer$_{Bf}$ and restimulated with 10 μg/ml α-GalCer$_{Bf}$ in the presence or absence of control Ig or anti-Cd1d blocking antibodies. IFN-γ secretion was measured in supernatants 40-48 hours later.

Figure 6A:
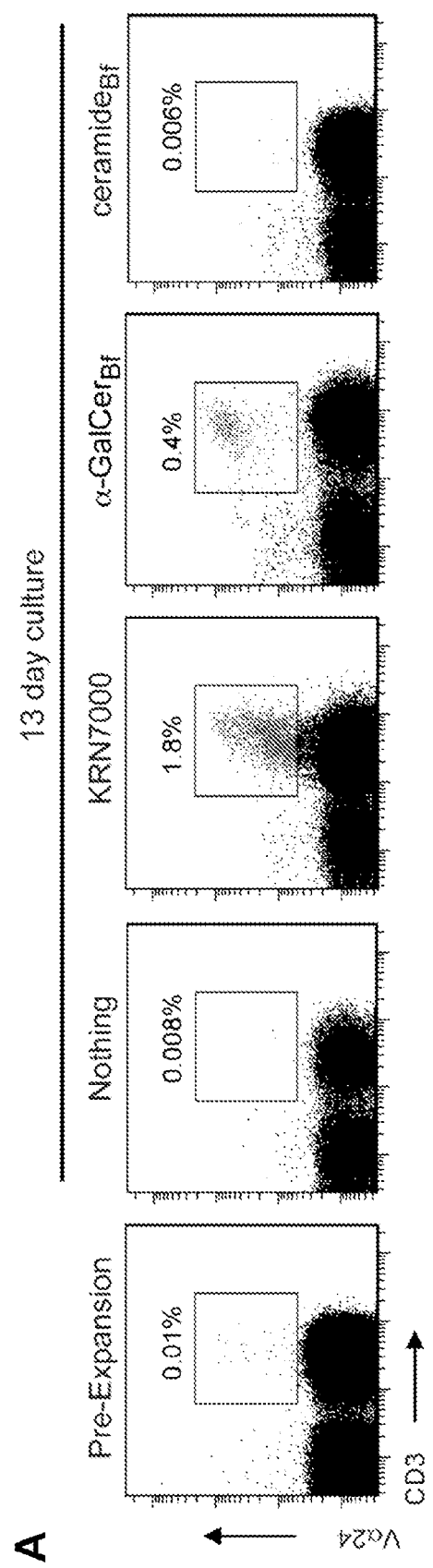
FIGS. 6A and 6B illustrate that α-GalCer$_{Bf}$ binds human CD1d and activates human NKT cells in vitro.

The results are shown in FIG. 6A. PBMCs cultured with KRN7000 or α-GalCer$_{Bf}$ showed an expansion of a population of CD3$^+$Vα24$^+$ cells while PBMCs left untreated or treated with ceramide$_{Bf}$ did not show an expansion of this cell population. The result indicates that the activity of α-GalCer$_{Bf}$ is specific and not due to a contaminant of the lipid purification process because ceramide$_{Bf}$, which was purified in a similar manner, did not exhibit this effect.

Figure 6B:
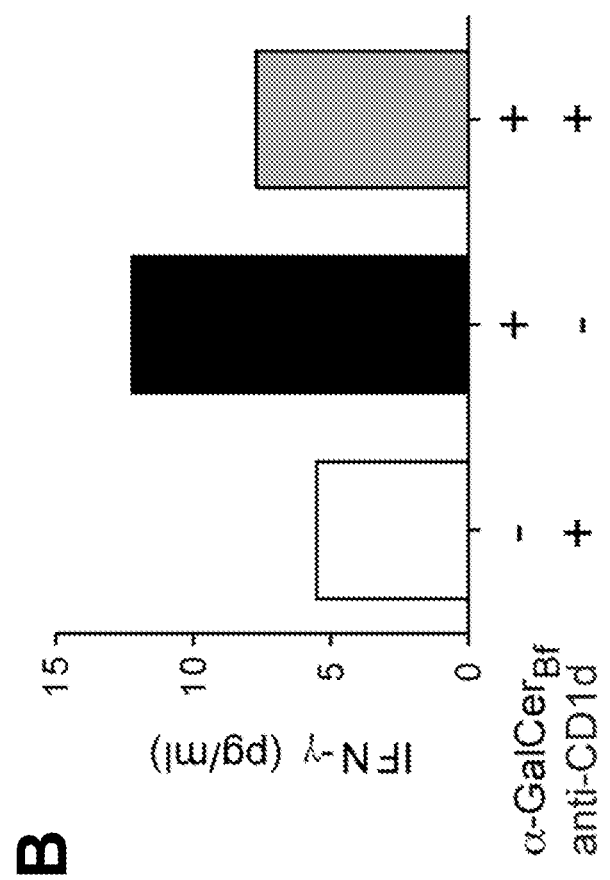

The capability of α-GalCer$_{Bf}$ to induce cytokine production in the Vα24$^+$ cells was also determined. The Vα24$^+$ cells that were expanded with α-GalCer$_{Bf}$ were re-stimulated with additional α-GalCer$_{Bf}$. As observed with murine NKT cells, α-GalCer$_{Bf}$ induced IFN-γ production by these human Vα24$^+$ cell lines in a CD1d-dependent manner because the effect was inhibited by co-culture with anti-CD1d blocking antibodies (see FIG. 6B). These results show that α-GalCer$_{Bf}$ has a similar effect on both murine and human NKT cells and further demonstrates the capability of α-GalCer$_{Bf}$ to bind human CD1d.

Example 8

In Vivo Stimulation of NKT Cells by *B. fragilis* α-GalCer$_{Bf}$

This example describes the capability of α-GalCer$_{Bf}$ to stimulate isolated NKT cells.

For in vivo activation of NKT cells, C57BL/6 female mice aged 6-12 weeks purchased from Jackson Laboratory (Bar Harbor, Me.) were used. Mice were housed under specific pathogen-free conditions at the University of California, San Francisco Animal Barrier Facility and experiments were approved by the Institutional Animal Care and Use Committee of the University of California, San Francisco.

Mice were sacrificed 16-18 hr after transfer of 0.4×10$^6$ mature CD86$^{hi}$MHCII$^{hi}$ BMDCs. Livers were cut into small pieces and passed through a stainless mesh. Cells were resuspended in 40% Percoll solution (GE Healthcare), underlaid with 60% Percoll solution and centrifuged at 2300 rpm for 20 min at room temperature. All isolations were performed in the presence of brefeldin A. After cell surface staining, cells were fixed in Cytofix/Cytoperm (BD Biosciences) according to the manufacturer's instructions and stained for intracellular cytokines Serum IFN-γ was measured by ELISA.

As described in Example 5, bone marrow progenitors were cultured in IMDM containing 10% FBS with addition of 20 ng/ml GM-CSF (G6 supernatant, a gift from Dr. Abul K. Abbas, University of California at San Francisco, San Francisco, Calif.) starting on day 2 and 1 ng/ml IL-4 (13L$_6$ supernatant, a gift from Dr. Abul K. Abbas) on day 6. For in vivo transfers, BMDCs were pulsed with 1 ng/mL LPS (*Escherichia coli* O26:B6; Sigma-Aldrich)+/−10 μg/mL α-GalCer$_{Bf}$ on day 8. After overnight culture, cells were harvested and washed twice before use.

Figure 7A:
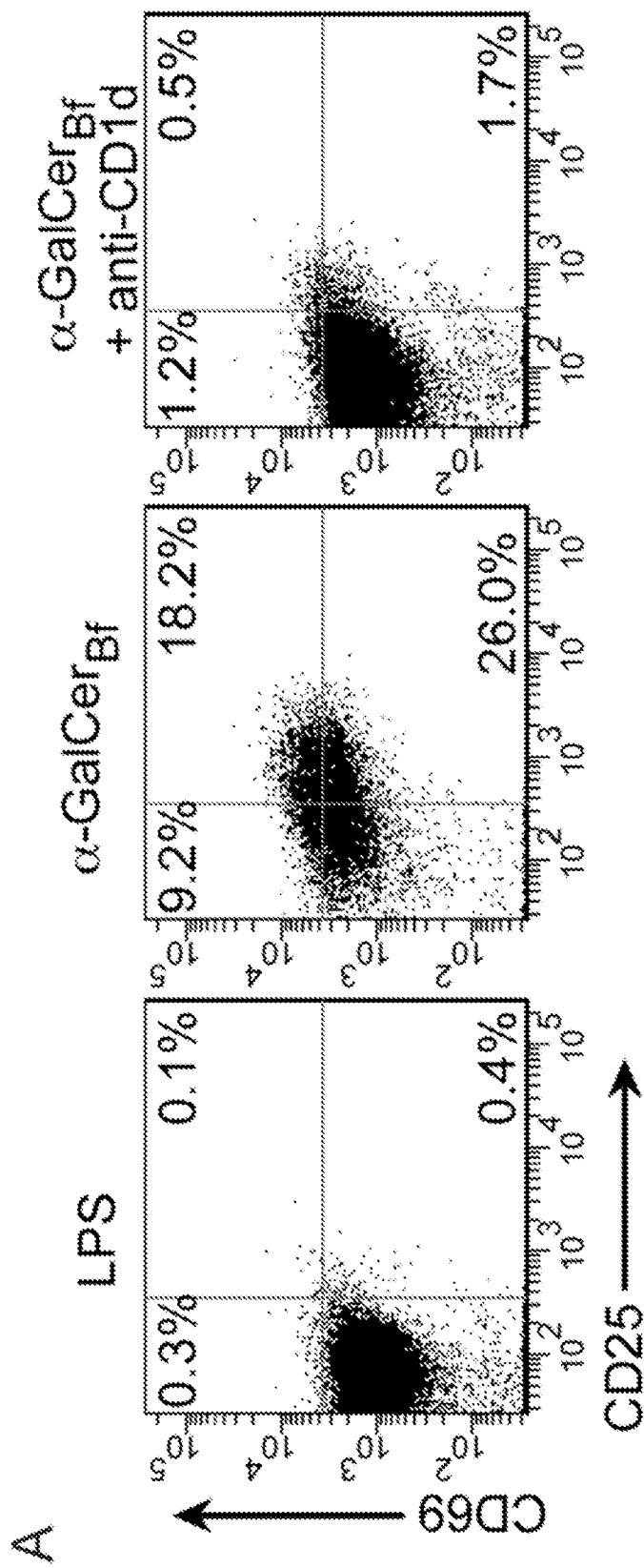
FIGS. 7A-7F illustrate that α-GalCer$_{Bf}$ activates NKT cells in vivo. Bone marrow-derived dendritic cells (BMDCs) were pulsed in vitro with LPS only or LPS+α-GalCer$_{Bf}$ for 24 hr. Then 0.4×10$^6$ cells were treated with control Ig or anti-CD1d blocking antibody and then transferred to WT mice. Liver mononuclear cells were analyzed 16-18 hr later. Data shown were pooled from three independent experiments.
Figure 7B:
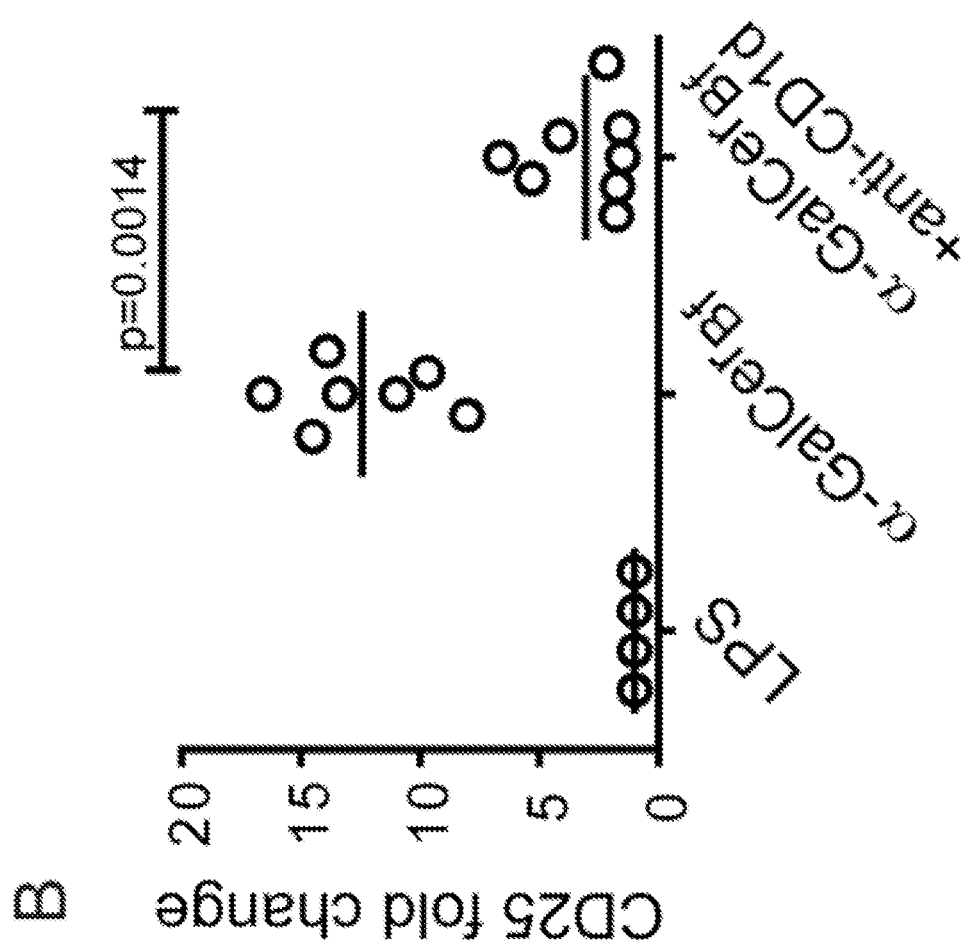
Figure 7C:
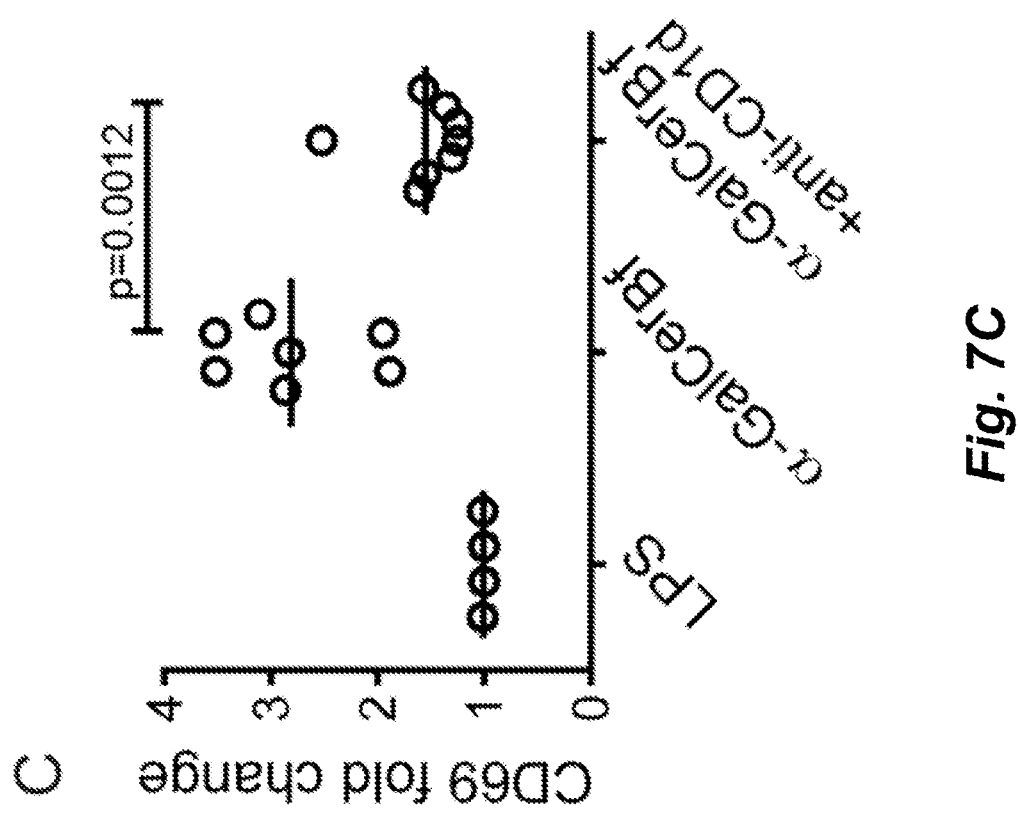
Figure 7D:
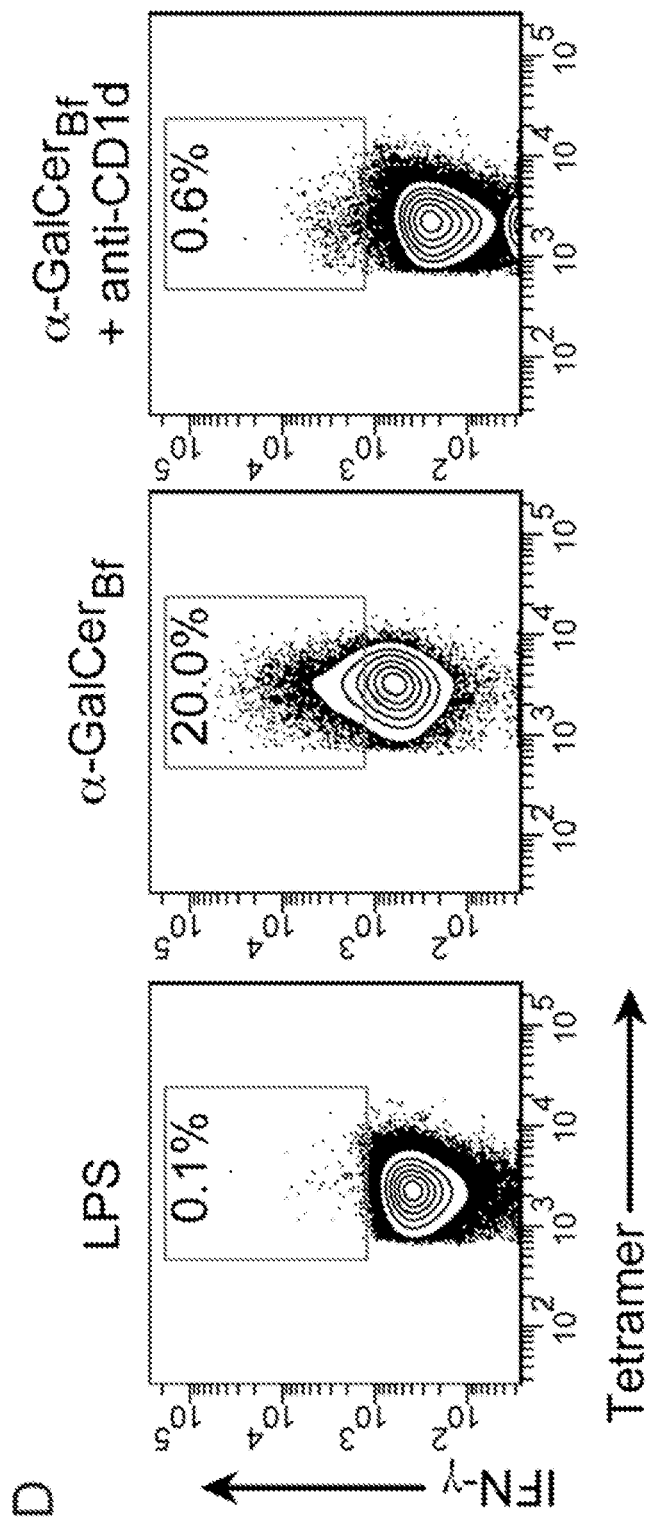
Figure 7E:
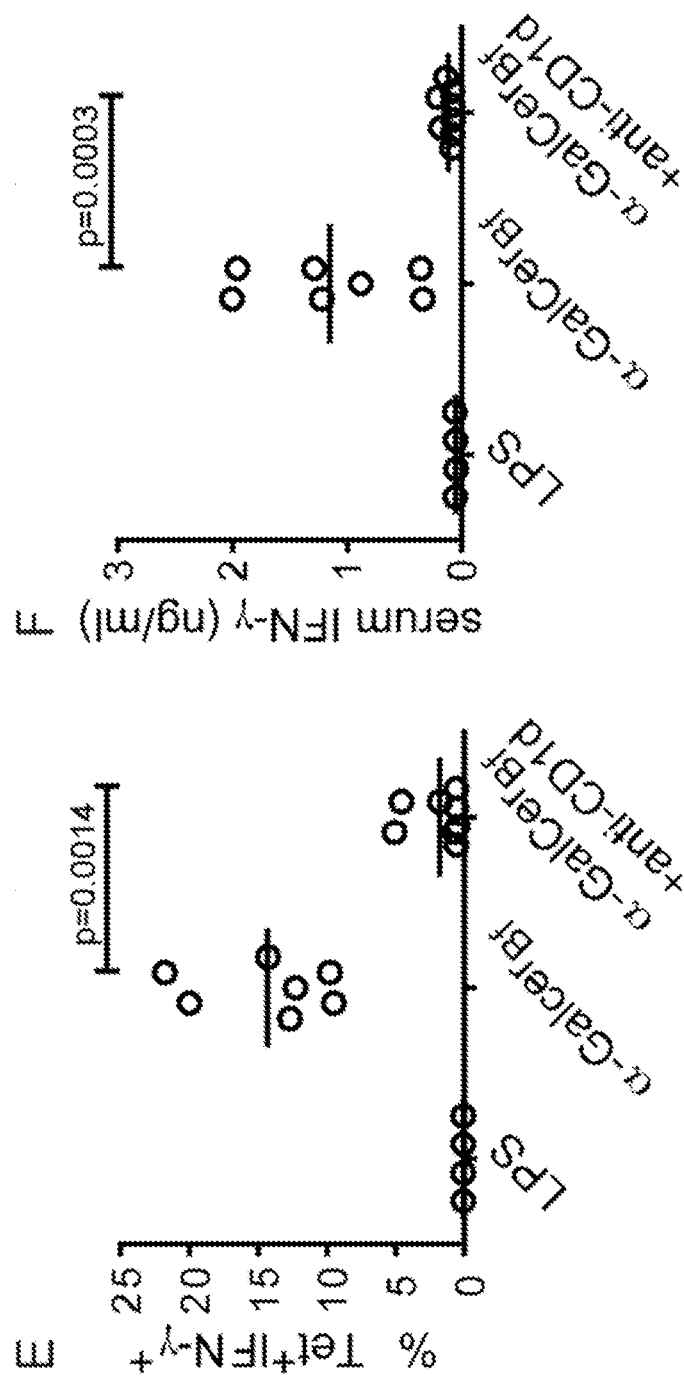
Figure 7F:
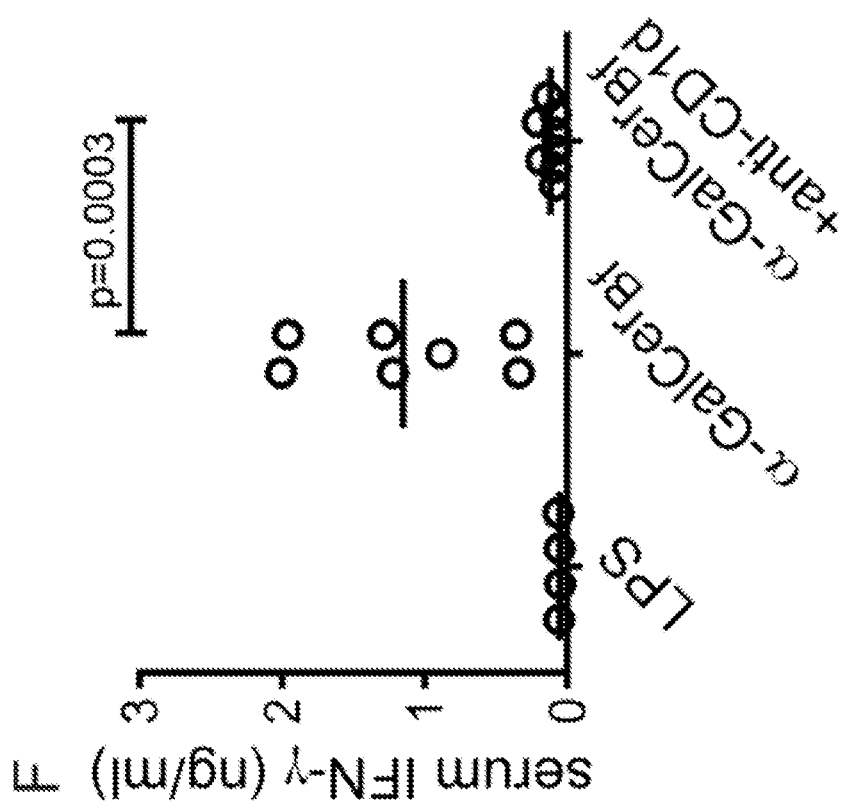

As described herein, because α-GalCer$_{Bf}$ is an agonist of NKT cell hybridomas and freshly isolated NKT cells in culture, the capability of α-GalCer$_{Bf}$ to activate NKT cells in vivo was determined. A previously validated assay was performed in which BMDCs are pulsed with KRN7000 in vitro and then used to immunize mice; this process has been shown to activate NKT cells and preferentially induce IFN-γ production (see, e.g., Fujii et al., *Nat. Immunol.* 3:867-74 (2002)). Mice were immunized with BMDCs pulsed with LPS alone or LPS+α-GalCer$_{Bf}$. NKT cells isolated from the liver, gated as CD3$^+$PBS-57/CD1d$^+$ tetramer reactive cells (PBS-57 is a KRN7000 analogue optimized for tetramer loading (see, e.g., Liu et al. *J. Immunol. Methods* 312:34-39 (2006)), showed upregulation of the cell surface markers CD25 and CD69, indicating that NKT cells had been activated in vivo (see FIGS. 7A-7C). Additionally, 15% of liver NKT cells expressed IFN-γ without re-stimulation in response to BMDCs pulsed with α-GalCer$_{Bf}$ (see FIGS. 7D-7E). Elevated IFN-γ levels could also be measured in the serum of these mice as shown in FIG. 7F. When anti-CD1d blocking antibodies were administered prior to BMDC transfer, liver NKT cell activation and IFN-γ production were both inhibited, demonstrating the specificity of NKT cell activation (see FIGS. 7A-7F).

Example 9

Effect of *B. fragilis* α-GalCer$_{Bf}$ in MURINE Diabetes Model

KRN7000 prevents cyclophosphamide (CY) induced diabetes in a Non-Obese Diabetic (NOD) mouse model (see, e.g., Sharif et al., *Nat. Med.* 7:1057-62 (2001)). Prevention of diabetes in this model is believed to be associated with suppression of T and B cell responses to islet antigens as well as a polarization towards TH2-like responses (see Sharif, supra). This example describes the effect of α-GalCer$_{Bf}$ in the CY induced diabetes mouse model.

Figure 8:
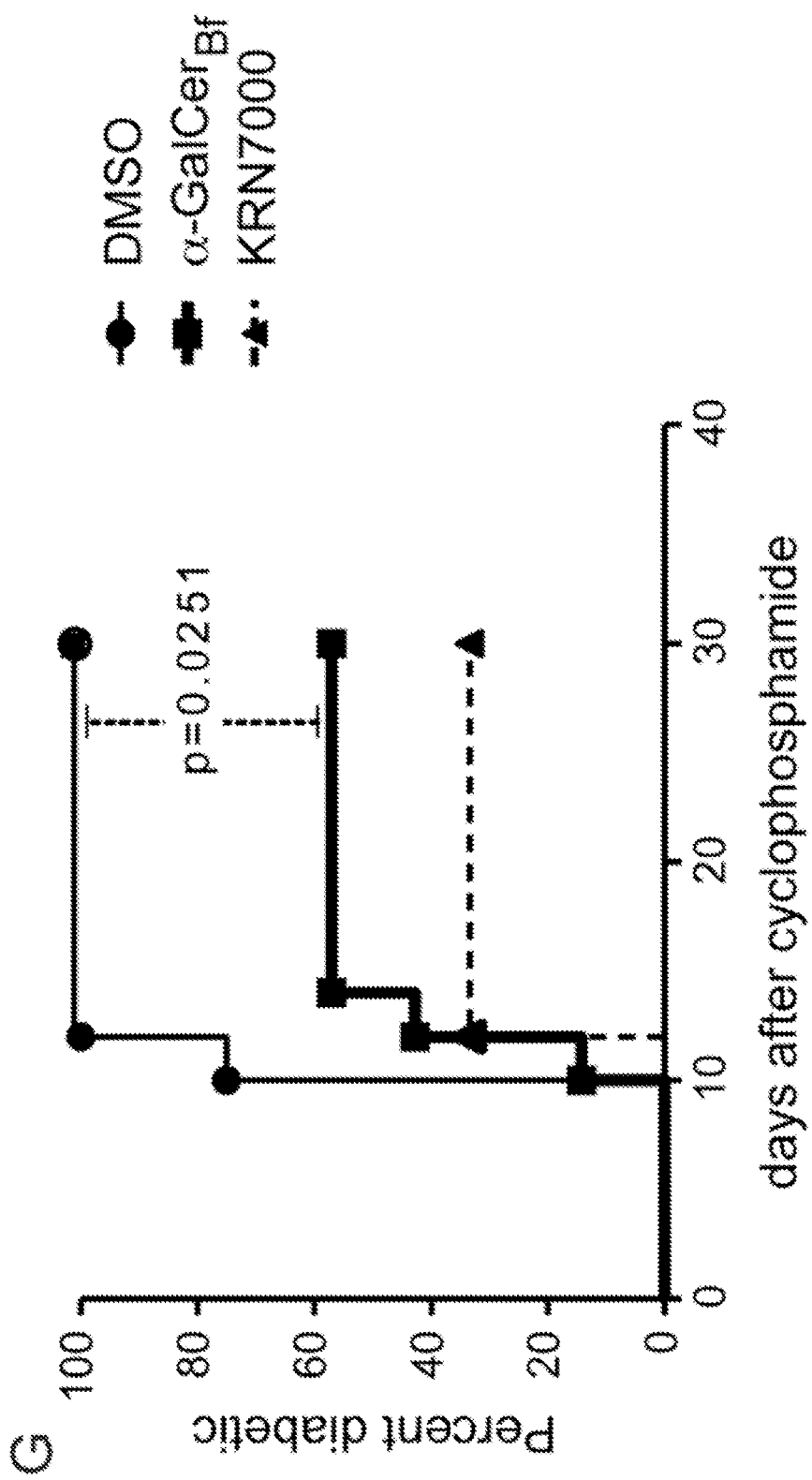
FIG. 8 presents a graph illustrating the percent of animals that developed diabetes in a cyclophosphamide-induced diabetes mouse model. Groups of animals received DMSO only, α-GalCer$_{Bf}$, or KRN7000. Number of animals is represented by n. Mice were considered diabetic when blood glucose was above 250 mg/dL. Blood glucose levels were measured at the time point shown. Data are representative of three independent experiments.

Groups of twelve-week old NOD female mice were given 300 mg/kg cyclophosphamide intraperitoneally on day 0. Groups of mice received DMSO (n=4), or 25 μg α-GalCer$_{Bf}$ (n=7) or 5 μg KRN7000 (n=3) diluted in DMSO intraperitoneally on days 0, 2, 4, 6, and 8. Diabetes progression was monitored by measuring blood glucose at each time point (see FIG. 8). Mice were considered diabetic when their blood blucose was above 250 mg/dL. α-GalCer$_{Bf}$ administration prevented diabetes development in more than 40% of mice while all (100%) of control DMSO-treated mice (vehicle only) developed diabetes (see FIG. 8). The number of animals developing diabetes in the group that received α-GalCer$_{Bf}$ compared with the DMSO group was statistically significant (p=0.0251). Comparable results were obtained from two additional experiments. In a second experiment, 5 mice received DMSO, 6 mice received α-GalCer$_{Bf}$, and 5 mice received KRN7000. In a third experiment, α-GalCer$_{Bf}$ was administered to three mice, and DMSO was administered to two mice. Kaplan-Meier survival curves were determined by a log-rank test using Prism software.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A compound having the following structure (I):

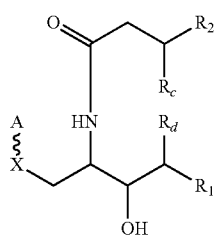

(I)

or a single stereoisomer, a mixture of stereoisomers, tautomer or pharmaceutically acceptable salt thereof, wherein A is a sugar moiety;

X is —O—, —S—, —NH—, or —CH$_2$—;

∼∼∼ is a glycosidic bond;

R$_1$ is C$_{5-28}$ fatty acid chain optionally substituted with one or more substituents selected from the group consisting of hydroxy, halo, —NR$_a$R$_b$, oxo, and C$_{1-3}$ lower alkyl, or -L$_1$-Q$_1$-R$_3$;

R$_2$ is C$_{5-19}$ fatty acid chain optionally substituted with one or more substituents selected from the group consisting of hydroxy, halo, —NR$_a$R$_b$, oxo, and C$_{1-3}$ lower alkyl; or -L$_2$-Q$_2$-R$_4$; ;

R$_a$ and R$_b$ are the same or different and independently hydrogen, acyl, or alkyl;

R$_c$, is hydroxy; and

R$_d$ is hydrogen, or alkyl;

L$_1$ and L$_2$ are the same or different and independently C$_{1-26}$ alkylene or C$_{2-26}$ alkenylene chain optionally substituted with one or more substituents selected from the group consisting of hydroxy, halo, —NR$_a$R$_b$, oxo, and C$_{1-3}$ lower alkyl;

Q$_1$ and Q$_2$ are the same or different and independently carbocycle or heterocycle; and R$_3$ and R$_4$ are the same or different and independently hydrogen or C$_{1-28}$ fatty acid chain optionally substituted with one or more substituents selected from the group consisting of hydroxy, halo, —NR$_a$R$_b$, oxo, and C$_{1-3}$ lower alkyl, provided that the compound is not:

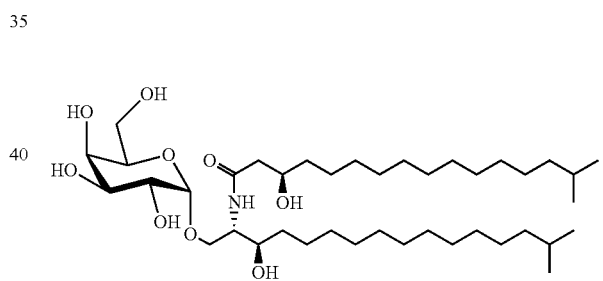

2. The compound of claim 1, wherein the compound has the following structure (Ia):

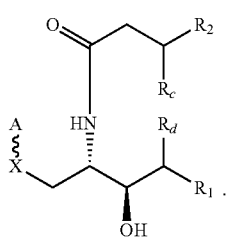

(Ia)

3. The compound of claim 1 wherein the compound has the following structure (IIa):

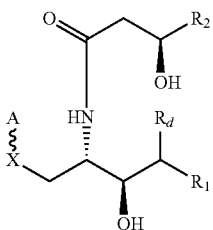

or has the following structure (IIb):

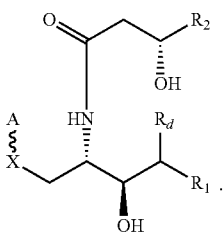

4. The compound of claim 1 wherein X is —O—.

5. The compound of claim 1, wherein (a) A is a monosaccharide selected from glucose, galactose, mannose, talose, iodose, altrose, gulose, allose, ribose, arabinose, xylose, and lyxose or a derivative thereof; or (b) A is a disaccharide selected from sucrose, lactulose, lactose, maltose, trehalose, and cellobiose or a derivative thereof.

6. The compound of claim 1, wherein A is

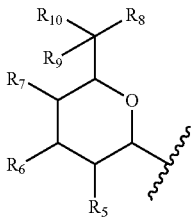

or A is a galactose derivative represented by

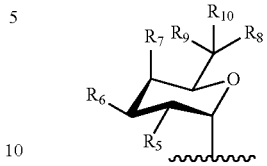

wherein,
$R_5$ is hydrogen, —$OR_e$, —$NR_aR_b$, halo, or $C_{1-3}$ lower alkyl; $R_6$, $R_7$, and $R_8$—$OR_e$;
$R_9$ and $R_{10}$ are the same or different and independently hydrogen or $C_{1-3}$ lower alkyl, or $R_9$ and $R_{10}$ together form =O, =S or =NH;
$R_a$ and $R_b$ are the same or different and independently hydrogen, acyl, or alkyl; and
$R_e$ is hydrogen, acyl, alkyl, a monosaccharide or a derivative thereof.

7. The compound of claim 1, wherein (a) $R_2$ is $C_{5-19}$alkyl, $C_{5-15}$alkyl, $C_{9-19}$alkyl, $C_{9-15}$alkyl, $C_{5-19}$alkenyl, $C_{5-15}$alkenyl, $C_{9-19}$alkenyl or $C_{9-15}$alkenyl, and wherein $R_2$ may be optionally substituted with one or more hydroxy; or (b) $R_2$ is —$(CH_2)_mCH(CH_3)_2$, and wherein m is an integer of between 4 and 12; or (c) $R_2$ is —$(CH_2)_{11}$ $CH(CH_3)_2$.

8. The compound of claim 1, wherein (a) $R_1$ is $C_{9-15}$alkyl; or $C_{9-15}$alkenyl; and wherein $R_1$ may be optionally substituted with one or more hydroxy; or (b) wherein $R_1$ is —$(CH_2)_mCH_3$ or —$(CH_2)_mCH(CH_3)_2$, wherein m is an integer between 4 and 12; or (c) $R_1$ is —$(CH_2)_{12}CH_3$ or —$(CH_2)_{10}CH(CH_3)_2$.

9. The compound of claim 8 wherein $R_d$ is hydrogen.

10. The compound of claim 1 having the following structure:

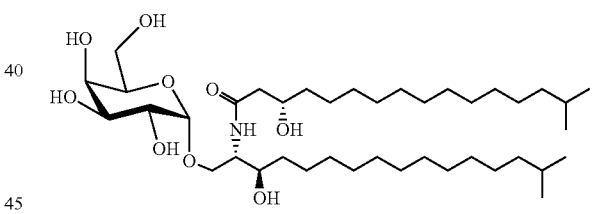

11. A pharmaceutical composition comprising the compound of claim 1 and a pharmaceutically acceptable excipient.

12. A method for activating a natural killer T cell (NKT cell) comprising contacting the NKT cell with the compound of claim 1.

* * * * *